US006358710B1

(12) United States Patent
Graves et al.

(10) Patent No.: US 6,358,710 B1
(45) Date of Patent: Mar. 19, 2002

(54) HUMANIZED ANTIBODIES THAT BIND TO THE ANTIGEN BOUND BY ANTIBODY NR-LU-13

(75) Inventors: Scott S. Graves, Monroe; John M. Reno, Brier; Robert W. Mallett, Everett; Mark D. Hylarides, Stanwood, all of WA (US); Stephen M. J. Searle, Cambridge; Andrew H. Henry, Ely, both of (GB); Jan T. Pedersen, Bronshoj (DK); Anthony R. Rees, St. Chaptes (GB)

(73) Assignee: NeoRx Corporation, Seattle, WA (US)

( * ) Notice: Subject to any disclaimer, the term of this patent is extended or adjusted under 35 U.S.C. 154(b) by 0 days.

(21) Appl. No.: 08/871,488

(22) Filed: Jun. 9, 1997

Related U.S. Application Data

(63) Continuation-in-part of application No. 08/660,362, filed on Jun. 7, 1996, now abandoned.

(51) Int. Cl.[7] ................................ C12P 21/04
(52) U.S. Cl. .................. 435/70.1; 435/325; 435/330; 530/387.1; 424/130.1; 436/547
(58) Field of Search ............. 424/130.1, 133.1, 424/134.1, 138.1, 139.1, 141.1, 142.1, 174.1; 435/4, 325, 358, 330, 70.1; 436/547; 530/387.1, 387.3

(56) References Cited

U.S. PATENT DOCUMENTS

| 4,237,224 A | 12/1980 | Cohen et al. ............... 435/68 |
|---|---|---|
| 4,399,216 A | 8/1983 | Axel et al. ................. 435/6 |
| 4,468,464 A | 8/1984 | Cohen et al. ............... 435/317 |
| 4,634,665 A | 1/1987 | Axel et al. ................. 435/68 |
| 4,656,134 A | 4/1987 | Ringold ..................... 435/91 |
| 4,740,470 A | 4/1988 | Cohen et al. ............... 435/172.3 |
| 4,816,397 A | 3/1989 | Boss et al. .................. 435/68 |
| 4,816,567 A | 3/1989 | Cabilly et al. .............. 530/387 |
| 4,870,023 A | 9/1989 | Fraser et al. ................ 435/320 |
| 4,879,236 A | 11/1989 | Smith et al. ................ 435/235 |
| 4,946,778 A | 8/1990 | Ladner et al. .............. 435/69.6 |
| 4,975,369 A | 12/1990 | Beavers et al. ............. 435/69.1 |
| 5,015,580 A | 5/1991 | Christou et al. ........... 435/172.3 |
| 5,041,379 A | 8/1991 | Fraser et al. ............... 435/235.1 |
| 5,071,748 A | 12/1991 | Miller ........................ 435/69.1 |
| 5,077,214 A | 12/1991 | Guarino et al. ............ 435/240.2 |
| 5,084,396 A | 1/1992 | Morgan, Jr. et al. ........ 436/513 |
| 5,091,513 A | 2/1992 | Huston et al. .............. 530/387 |
| 5,110,729 A | 5/1992 | Maeda et al. ............... 435/69.1 |
| 5,120,657 A | 6/1992 | McCabe et al. ............. 435/287 |
| 5,122,458 A | 6/1992 | Post et al. .................. 435/69.1 |
| 5,132,405 A | 7/1992 | Huston et al. .............. 530/387.3 |
| 5,147,788 A | 9/1992 | Page et al. .................. 435/69.1 |
| 5,149,655 A | 9/1992 | McCabe et al. ............. 435/287 |
| 5,155,037 A | 10/1992 | Summers ................... 435/240.2 |
| 5,162,222 A | 11/1992 | Guarino et al. ............ 435/240.2 |
| 5,169,784 A | 12/1992 | Summers et al. .......... 435/320.1 |
| 5,169,939 A | 12/1992 | Gefter et al. ............... 530/387.3 |
| 5,179,007 A | 1/1993 | Jarvis et al. ................ 435/68.1 |
| 5,179,017 A | 1/1993 | Axel et al. ................. 435/240.2 |
| 5,185,254 A | 2/1993 | Linnenbach .............. 435/172.3 |
| 5,225,539 A | 7/1993 | Winter ....................... 530/387.3 |
| 5,260,203 A | 11/1993 | Ladner et al. .............. 435/172.3 |
| 5,266,314 A | 11/1993 | Maeda ....................... 424/93 A |
| 5,304,489 A | 4/1994 | Rosen ........................ 435/320.1 |
| 5,322,774 A | 6/1994 | Peakman et al. ............ 435/69.1 |
| 5,348,886 A | 9/1994 | Lee et al. ................... 435/320.1 |
| 5,348,887 A | 9/1994 | Bumol et al. |
| 5,349,053 A | 9/1994 | Landolfi ..................... 530/351 |
| 5,385,839 A | 1/1995 | Stinski ....................... 435/240.2 |
| 5,405,779 A | 4/1995 | McCabe et al. ............. 435/287 |
| 5,413,923 A | 5/1995 | Kucherlapti et al. ...... 435/172.3 |
| 5,422,281 A | 6/1995 | Harris et al. ................ 436/501 |
| 5,434,340 A | 7/1995 | Krimpenfort et al. ........... 800/2 |

(List continued on next page.)

FOREIGN PATENT DOCUMENTS

| CA | 1 316 852 C | 4/1993 |
|---|---|---|
| EP | 045 809 B1 | 2/1982 |
| EP | 120 694 B1 | 10/1984 |
| EP | 125 023 B1 | 11/1984 |
| EP | 173 552 A1 | 3/1986 |
| EP | 239 400 B1 | 9/1987 |
| EP | 260 148 A2 | 3/1988 |
| EP | 319 206 A2 | 6/1989 |
| EP | 328 404 B1 | 8/1989 |
| EP | 338 841 A1 | 10/1989 |
| EP | 393 045 B1 | 10/1990 |
| EP | 411 893 A2 | 2/1991 |
| EP | 451 216 B1 | 10/1991 |
| EP | 460 167 B1 | 12/1991 |
| EP | 520 962 A2 | 12/1992 |
| EP | 578 515 A2 | 1/1994 |
| EP | 592 106 A1 | 4/1994 |
| EP | 614 982 A1 | 9/1994 |
| EP | 682 040 A1 | 11/1995 |
| EP | 699 755 A2 | 3/1996 |
| GB | 2 188 638 A | 10/1987 |

(List continued on next page.)

OTHER PUBLICATIONS

Better et al, Science 240: 1041–1043, May 20, 1988.*
Morrison, S. L., Annu. Rev. Immunol. 10: 239–65, Dec. 31, 1992.*
Abraham et al, J. Immunol. Methods 144:77–86, Oct. 15, 1991.*
Verhoeyen et al BioEssays vol. 8(2) 74–78, Mar. 1988.*
Rodwell Nature vol. 342 99–100, Nov. 1989.*
Geysen et al Proc NAtl Acad Sci USA vol. 81 3998–4002, Jul. 1984.*

(List continued on next page.)

Primary Examiner—Susan Ungar
Assistant Examiner—Minh-Tam Davis
(74) Attorney, Agent, or Firm—Seed Intellectual Property Law Group PLLC

(57) ABSTRACT

Humanized antibodies which bind the NR-LU-13 antigen, conjugates containing such antibodies, and their use in pretargeting methods and conventional antibody therapy and immunodiagnosis are provided.

7 Claims, 35 Drawing Sheets

U.S. PATENT DOCUMENTS

| | | | |
|---|---|---|---|
| 5,443,953 A | 8/1995 | Hansen et al. | 424/1.49 |
| 5,464,764 A | 11/1995 | Capecci et al. | 435/172.3 |
| 5,476,786 A | 12/1995 | Huston | 435/252.33 |
| 5,487,992 A | 1/1996 | Capecchi et al. | 435/172.3 |
| 5,503,998 A | 4/1996 | Christou et al. | 435/172.3 |
| 5,506,125 A | 4/1996 | McCabe et al. | 435/172.1 |
| 5,525,510 A | 6/1996 | McCabe et al. | 435/285.3 |
| 5,530,101 A | 6/1996 | Queen et al. | 530/387.3 |
| 5,545,403 A | 8/1996 | Page | 424/133.1 |
| 5,545,404 A | 8/1996 | Page | 424/133.1 |
| 5,545,405 A | 8/1996 | Page | 424/133.1 |
| 5,545,806 A | 8/1996 | Lonberg et al. | 800/2 |
| 5,569,825 A | 10/1996 | Lonberg et al. | 800/2 |
| 5,578,287 A | 11/1996 | Theodore et al. | 424/1.49 |
| 5,584,807 A | 12/1996 | McCabe | 604/71 |
| 5,585,089 A | 12/1996 | Queen et al. | 424/133.1 |
| 5,585,097 A | 12/1996 | Bolt et al. | 424/133.1 |
| 5,624,821 A | 4/1997 | Winter et al. | 435/69.6 |

FOREIGN PATENT DOCUMENTS

| | | | |
|---|---|---|---|
| WO | WO 84/03712 | 9/1984 | |
| WO | WO 86/01533 | 3/1986 | |
| WO | WO 86/02097 | 4/1986 | |
| WO | WO 86/05807 | 10/1986 | |
| WO | WO 87/04462 | 7/1987 | |
| WO | WO 88/01649 | 3/1988 | |
| WO | WO 88/06630 | 9/1988 | |
| WO | WO 89/09825 | 10/1989 | |
| WO | WO 89/10404 | 11/1989 | |
| WO | WO 90/04036 | 4/1990 | |
| WO | WO 90/10457 | * 9/1990 | 424/85.91 |
| WO | WO 91/06320 | 5/1991 | |
| WO | WO 91/06657 | 5/1991 | |
| WO | WO 91/09967 | 7/1991 | |
| WO | WO 92/04381 | 3/1992 | |
| WO | WO 92/11018 | 7/1992 | |
| WO | WO 92/15683 | 9/1992 | |
| WO | WO 92/22653 | 12/1992 | |
| WO | WO 93/08300 | 4/1993 | |
| WO | WO 93/11238 | 6/1993 | |
| WO | WO 93/12246 | 6/1993 | |
| WO | WO 93/16185 | 8/1993 | |
| WO | WO 93/17105 | 9/1993 | |
| WO | WO 93/22332 | 11/1993 | |
| WO | WO 93/22442 | 11/1993 | |
| WO | WO 93/23537 | 11/1993 | |
| WO | WO 93/25240 | 12/1993 | |
| WO | WO 94/04679 | 3/1994 | |
| WO | WO 94/09131 | 4/1994 | |
| WO | WO 94/12625 | 6/1994 | |
| WO | WO 94/22902 | 10/1994 | |
| WO | WO 94/29451 | 12/1994 | |
| WO | WO 95/08577 | 3/1995 | |
| WO | WO 95/15335 | 6/1995 | |
| WO | WO 95/15341 | 6/1995 | |
| WO | WO 95/15769 | 6/1995 | |
| WO | WO 95/20672 | 8/1995 | |
| WO | WO 95/25167 | 9/1995 | |
| WO | WO 96/05228 | 2/1996 | |
| WO | WO 96/11013 | 4/1996 | |
| WO | WO 96/27011 | 9/1996 | |

OTHER PUBLICATIONS

Greenspan Nature Biotechnology vol. 7:936–937, 1999.*

Weiden, P. et al., "Rhenium–186–labeled Chimeric antibody NR–LU–13: Pharmacokinetics, biodistribution and immunogenicity relative to murine analog NR–LU–10," *The Journal of Nuclear Medicine* 34(12):2111–2119, 1993.

Goshorn et al., "Preclinical development of huNR–LU–10, a humanized antibody for tumor targeting," *Immunotechnology* 2(4):p. 300, 1996.

Leung et al., "Construction and Characterization of a Humanized, Internalizing, B–cell (CD22)–Specific, Leukemia/Lymphoma Antibody LL2," *Molecular Immunology* 32(17/18):1413–1427, 1995.

Taylor et al., "Altered Glycosylation and Selected Mutation in Recombinant . . . Activity," *Immunology* 83(3):50–506, 1994.

Dwek et al., "Glycobiology: The Function of Sugar in the IgG Molecule," *The Journal of Anatomy* 187(Part 2):279–292, 1995.

Davis et al., "Glycosylation Governs the Binding of Antipeptide . . . Virus Type 1," *The Journal of General Virology* 71(Part 12):2773–3148, 1990.

Heyman et al., "Carbohydrate Chains on IgG2b: A Requirement For Efficient Feedback Immunosuppression," *The Journal of Immunology* 134(6):4018–4023, 1985.

Muraoka et al., "Structural Requirements For IgM Assembly and Cytolytic Activity," *The Journal of Immunology* 142(2):695–701, 1989.

Sarmay et al., "Mapping and Comparison of the Interaction Sites on . . . Receptor," *Molecular Immunology* 29(5):633–639, 1992.

Pound et al., "Aglycosylated Chimaeric Human IgG3 Can Trigger The Human Phagocyte Respiratory Burst," *Molecular Immunology* 30(3):233–241, 1993.

Co et al., "Genetically Engineered Deglycosylation of the Variable . . . Antibody," *Molecular Immunology* 30(15):1361–1367, 1993.

Endo et al., "Glycosylation of the Variable Region . . . Chains," *Molecular Immunology* 32(13):931–940, 1995.

Xia et al., "Efficient Complement–Mediated . . . Antigen," *Molecular Immunology* 30(12):1089–1096, 1993

Greenman et al., "The Use of the Intracellular Single–Chain . . . Molecules," *Journal of Immunological Methods* 194(2):169–180, 1996.

Couto et al., "Cloning of cDNA's Encoding . . . Antibody," *Hybridoma* 12(4):485–489, 1993.

Peake et al., "Does Non–Enymatic Glycosylation Affect Complement Function in Diabetes?," *Diabetes Research* 11(2):109–114, 1989.

Tachibana et al., "Identification of Hybrid–Type Carbohydrate . . . Adenocarcinoma," *Biochimica et Biophysica Acta* 1182(3):257–263, 1993.

Nishimura et al., "Recombinant Human–Mouse Chimeric Monoclonal . . . Antigen," *Cancer Research* 47(4):999–1005, 1987.

Yoshida et al., "Mutants of Dictyostellium Discoideum . . . Site A," *Cell Structure and Function* 16(5):383–390, 1991.

Xia et al., "Structure of the CAMPATH–1 Antigen . . . Complement Lysis," *Biochemical Journal* 293(Part 3):633–640, 1993.

Brekke et al., "The structural requirements for complement activation by IgG: does it hinge on the hinge," *Immunol Today* 16(2):85–90, 1995.

Brüggemann et al., "Comparison Of The Effector Functions Of Human Immunoglobulins Using A Matched Set Of Chimeric Antibodies," *J. Exp. Med.* 166: 1351–1361, 1987.

Canfield and Morrison, "The Binding Affinity of Human IgG for its High Affinity Fc Receptor Is Determined by Multiple Amino Acids in the $C_H2$ Domain and Is Modulated by the Hinge Region," *J. Exp. Med. 173*: 1483–1491, 1991.

Dorai et al., "Aglycosylated Chimeric Mouse/Human IgG1 Antibody Retains Some Effector Function," *Hybridoma 10*(2): 211–217, 1991.

Hand et al., "Comparative biological properties of a recombinant chimeric anti–carcinoma mAb and a recombinant aglycosylated variant," *Cancer Immunology Immunotherapy 35*: 165–174, 1992.

Helfich et al., "Epitope Mapping Of SCLC–Cluster–2 Mabs And Generation Of Antibodies Directed Against New EGP–2 Epitopes," *Int. J. Cancer: Supplement 8*: 64–69, 1994.

Herlyn et al., "CO 17–1A and Related Monoclonal Antibodies: Their Production and Characterization," *Hybridoma 5*(Suppl. 1): S3–S10, 1986.

Houba et al., "Improved Characteristics of a Human β–Glucuronidase–Antibody Conjugate after Deglycosylation for Use in Antibody–Directed Enzyme Prodrug Therapy," *Bioconjugate Chem. 7*: 606–611, 1996.

Kabat, "The Structural Basis Of Antibody Complementarity," *Adv. Protein Chem. 32*: 1–75, 1978.

Leij et al., "SCLC–Cluster–2 Antibodies Detect The Pancarcinoma/Epithelial Glycoprotein EGP–2," *Int. J. Cancer: Supplement 8*: 60–63, 1994.

Litvinov et al., "Ep–CAM: A Human Epithelial Antigen Is a Homophilic Cell–Cell Adhesion Molecule," *The Journal of Cell Biology 125*(2): 437–446, 1994.

Lund et al., "Control of IgG/Fc Glycosylation: A Comparison Of Oligosaccarides From Chimeric Human/Mouse and Mouse Subclass Immunoglobulin," *Molecular Immunology 30*(8): 741–748, 1993.

McCloskey et al., "Human constant regions influence the antibody binding characteristics of mouse–human chimeric IgG subclasses," *Immunology 88*: 169–173, 1996.

Morgan et al., "The N–terminal end of the $C_H2$ domain of chimeric human IgG1 anti–HLA–DR is necessary for C1q, FcγRI and FcγRIII binding," *Immunology 86*: 319–324, 1995.

Strnad et al., "Molecular Cloning and Characterization of a Human Adenocarcinoma/Epithelial Cell Surface Antigen Complementary DNA," *Cancer Research 49*: 314–317, 1989.

Szala et al., "Molecular cloning of cDNA for the carcinoma–associated antigen GA733–2," *Proc. Natl. Acad. Sci. USA 87*: 3542–3546, 1990.

Tams and Welinder, "Mild Chemical Deglycosylation of Horseradish Pereoxidase Yields a Fully Active, Homogenous Enzyme," *Analytical Biochemistry 228*: 48–55, 1995.

Tao and Morrison, "Studies Of Aglycosylated Chimeric Mouse–Human IgG. Role of Carbohydrate in the Structure and Effector Functions Mediated by the Human IgG Constant Region," *Journal Of Immunology 143*: 2595–2601, 1989.

Tao et al., "The Differential Ability of Human IgG1 and IgG4 to Activate Complement Is Determined by the COOH–terminal Sequence of the $C_H2$ Domain," *J. Exp. Med. 173*: 1025–1028, 1991.

Winkelhake et al., "Effects of pH Treatments and Deglycosylation of Rabbit Immunoglobulin G on the Binding of C1q," *The Journal Of Biological Chemistry 255*(7): 2822–2828, 1980.

Woof and Amin, "The Role of Glycosylation in Antibody Effector Function," *GlycoNews Second 94*: 1–4, 1994.

\* cited by examiner

NR-LU-13 Heavy chain variable region sequences

```
GAG GTT CAG CTG CAG CAG TCT GGG GCA GAG CTT GTG AAG CCA GGG GCC TCA GTC AGG TTG TCC TGC
Glu Val Gln Leu Gln Gln Ser Gly Ala Glu Leu Val Lys Pro Gly Ala Ser Val Arg Leu Ser Cys    22
                                                 CDR1
ACA GCT TCT GGC TTC AAC ATT AAA GAC ACC TAT ATG CAC TGG GTG ATA GAG AGG CCT GAA CAG GGC
Thr Ala Ser Gly Phe Asn Ile Lys Asp Thr Tyr Met His Trp Val Ile Glu Arg Pro Glu Gln Gly    44
                                       CDR2
CTG GAG TGG ATT GGA AGG ATT GAT CCT GCG AAT GGT AAT ACT AAA TGT GAC CCG AAG TTC CAG GGC
Leu Glu Trp Ile Gly Arg Ile Asp Pro Ala Asn Gly Asn Thr Lys Cys Asp Pro Lys Phe Gln Gly    66

AAG GCC ACT ATA ACA GCA GAC ACA TCC TCC AAC ACA GCC TAC CTG CAG CTC AGC AGC CTG ACA TCT
Lys Ala Thr Ile Thr Ala Asp Thr Ser Ser Asn Thr Ala Tyr Leu Gln Leu Ser Ser Leu Thr Ser    88
                                                                 CDR3
GAG GAC ACT GCC GTC TAT TAC TGT TCT AGA GAG GTC CTA ACT GGG ACG TGG TCT TTG GAC TAC TGG
Glu Asp Thr Ala Val Tyr Tyr Cys Ser Arg Glu Val Leu Thr Gly Thr Trp Ser Leu Asp Tyr Trp   110

GGT CAA GGA ACC TCA GTC ACC GTC TCC TCA
Gly Gln Gly Thr Ser Val Thr Val Ser Ser                                                    120
```

NR-LU-13 Light chain variable region sequences

```
GAC ATC CAG ATG ATT CAG TCT CCA TCG TCC ATG TTT GCC TCT CTG GGA GAC AGA GTC AGT CTC TCT
Asp Ile Gln Met Ile Gln Ser Pro Ser Ser Met Phe Ala Ser Leu Gly Asp Arg Val Ser Leu Ser    22
                              CDR1
TGT CGG GCT AGT CAG GGC ATT AGA GGT AAT TTA GAC TGG TAT CAG CAG AAA CCA GGT GGA ACT ATT
Cys Arg Ala Ser Gln Gly Ile Arg Gly Asn Leu Asp Trp Tyr Gln Gln Lys Pro Gly Gly Thr Ile    44
                              CDR2
AAA CTC CTG ATC TAC TCC ACA TCC AAT TTA AAT TCT GGT GTC CCA TCA AGG TTC AGT GGC AGT GGG
Lys Leu Leu Ile Tyr Ser Thr Ser Asn Leu Asn Ser Gly Val Pro Ser Arg Phe Ser Gly Ser Gly    66

TCT GGG TCA GAT TAT TCT CTC ACC ATC AGC AGC CTA GAC TCT GAA GAT TTT GCA GAC TAT TAC TGT
Ser Gly Ser Asp Tyr Ser Leu Thr Ile Ser Ser Leu Asp Ser Glu Asp Phe Ala Asp Tyr Tyr Cys    88
              CDR3
CTA CAG CGT AAT GCG TAT CCG TAC ACG TTC GGA GGG GGG ACC AAG CTG GAA ATA AAA
Leu Gln Arg Asn Ala Tyr Pro Tyr Thr Phe Gly Gly Gly Thr Lys Leu Glu Ile Lys                107
```

*Fig. 2*

Light Chain

| | | | | | | | | | |
|---|---|---|---|---|---|---|---|---|---|
| 1 | | | | 5 | | | | | 10 |
| ASP | ILE | GLN | MET | THR | GLN | SER | PRO | SER | SER |
| 11 | | | | 15 | | | | | 20 |
| LEU | SER | ALA | SER | VAL | GLY | ASP | ARG | VAL | THR |
| 21 | | | | 25 | | | | | 30 |
| ILE | THR | CYS | ARG | ALA | SER | GLN | GLY | ILE | ARG |
| 31 | | | | 35 | | | | | 40 |
| GLY | ASN | LEU | ASP | TRP | TYR | GLN | GLN | LYS | PRO |
| 41 | | | | 45 | | | | | 50 |
| GLY | LYS | GLY | PRO | LYS | LEU | LEU | ILE | TYR | SER |
| 51 | | | | 55 | | | | | 60 |
| THR | SER | ASN | LEU | ASN | SER | GLY | VAL | PRO | SER |
| 61 | | | | 65 | | | | | 70 |
| ARG | PHE | SER | GLY | SER | GLY | SER | GLY | SER | ASP |
| 71 | | | | 75 | | | | | 80 |
| TYR | THR | LEU | THR | ILE | SER | SER | LEU | GLN | PRO |
| 81 | | | | 85 | | | | | 90 |
| GLU | ASP | PHE | ALA | THR | TYR | TYR | CYS | LEU | GLN |
| 91 | | | | 95 | | | | | 100 |
| ARG | ASN | ALA | TYR | PRO | TYR | THR | PHE | GLY | GLN |
| 101 | | | | 105 | | | | | |
| GLY | THR | LYS | LEU | GLU | ILE | LYS | | | |

The humanized sequence of NRX451 light chain, residue positions which differ between NR-LU-13 and NRX451-humanized are marked with bold type.

*Fig. 3*

Heavy Chain

| | | | | | | | | | |
|---|---|---|---|---|---|---|---|---|---|
| 1 | | | | 5 | | | | | 10 |
| GLN | VAL | GLN | LEU | VAL | GLN | SER | GLY | ALA | GLU |
| 11 | | | | 15 | | | | | 20 |
| VAL | LYS | LYS | PRO | GLY | ALA | SER | VAL | LYS | VAL |
| 21 | | | | 25 | | | | | 30 |
| SER | CYS | LYS | ALA | SER | GLY | PHE | ASN | ILE | LYS |
| 31 | | | | 35 | | | | | 40 |
| ASP | THR | TYR | MET | HIS | TRP | VAL | ARG | GLN | ALA |
| 41 | | | | 45 | | | | | 50 |
| PRO | GLY | GLN | GLY | LEU | GLN | TRP | MET | GLY | ARG |
| 51 | | | | 55 | | | | | 60 |
| ILE | ASP | PRO | ALA | ASN | GLY | ASN | THR | LYS | CYS |
| 61 | | | | 65 | | | | | 70 |
| ASP | LEU | SER | PHE | GLN | GLY | ARG | VAL | THR | ILE |
| 71 | | | | 75 | | | | | 80 |
| THR | ALA | ASP | THR | SER | ILE | ASN | THR | ALA | TYR |
| 81 | | | | 85 | | | | | 90 |
| MET | GLU | LEU | SER | SER | LEU | ARG | SER | ASP | ASP |
| 91 | | | | 95 | | | | | 100 |
| THR | ALA | VAL | TYR | TYR | CYS | SER | ARG | GLU | VAL |
| 101 | | | | 105 | | | | | 110 |
| LEU | THR | GLY | THR | TRP | SER | LEU | ASP | TYR | TRP |
| 111 | | | | 115 | | | | | 120 |
| GLY | GLN | GLY | THR | LEU | VAL | THR | VAL | SER | SER |

The humanized sequence of NRX451 light chain, residue positions which differ between NR-LU-13 and NRX451-humanized are marked with bold type.

*Fig. 4*

Alignment of the Light Chain Variable Regions of
NR-LU-13 (top) and humanized NRX451 (bottom).

DIQMISSPSSMFASLGDRVSLSC RASQGIRGNLD WYQQKPGGTIKLLIY STSNLNS

.... ...... .. ............. ...... .......

DIQMTQSPSSLSASVGDRVTITC RASQGIRGNLD WYQQKPGKGPKLLIY STSNLNS
                      CDR1                           CDR2

GVPSRFSGSGSGSDYSLTISSLESEDFADYYC LQRNAYPYTF GGGTKLEIK

................ .... ... ............. . .......

GVPSRFSGSGSGSDYTLTISSLQPEDFATYYC LQRNAYPYTF GQGTKLEIK
                                 CDR3

Alignment of the Heavy Chain Variable Regions of
NR-LU-13 (top) and humanized NRX451 (bottom).

EVQLQQSGAELVKPGASVRLSCTASGFNIK DTYMH WVIERPEQGLEWIG

... ...... ...... .. ......... ..... .. . ... . .

QVQLVQSGAEVKKPGASVKVSCKASGFNIK DTYMH WVRQAPGQGLQWMG
                              CDR1

RIDPANGNTK CDPKFQGKATITADTSSNTAYLQLSSLTSEDTAVYYCS

.......... .. ... ......... .... .... . ........

RIDPANGNTK CDLSFQGRVTITADTSINTAYMELSSLRSDDTAVYYCS
CDR2

REVLTGTWSLDY WGQGTSVTVSS

............ ...... .....

REVLTGTWSLDY WGQGTLVTVSS
CDR3

Fig. 5

Same frequencies, but matching with human sequences. Only one occurence of Asp at poition 182 is found and no occurences of Cys at position 181.

| RES | 181 | 182 |
|---|---|---|
| A | - | 0.48 |
| R | - | 0.02 |
| N | 0.01 | 0.18 |
| D | 0.00 | 0.00 |
| C | 0.00 | 0.00 |
| Q | 0.00 | - |
| E | - | - |
| G | 0.00 | 0.01 |
| H | 0.00 | - |
| I | - | 0.00 |
| L | - | 0.00 |
| K | 0.00 | 0.00 |
| M | - | - |
| F | 0.03 | - |
| P | 0.00 | 0.01 |
| S | 0.01 | 0.23 |
| T | - | 0.02 |
| W | 0.00 | - |
| Y | 0.91 | - |
| V | 0.00 | 0.02 |
| X | 0.01 | 0.02 |
| O | - | - |
| - | - | - |
| Z | - | - |
| B | - | 0.00 |
| Total | 1.00 | 1.00 |

*Fig. 7A*

Sequence positions 50 and 183 are structural mutations within 5 Å of the CDR's. Frequency of residue types at these positions are identical.

Position 50 (153 human lambda sequences)

| RES | 50 |
|---|---|
| A | - |
| R | - |
| N | - |
| D | - |
| C | - |
| Q | - |
| E | - |
| G | - |
| H | - |
| I | 0.00 |
| L | - |
| K | - |
| M | 0.00 |
| F | - |
| P | 0.93 |
| S | - |
| T | - |
| W | - |
| Y | - |
| V | - |
| X | 0.06 |
| O | - |
| - | - |
| Z | - |
| B | - |
| Total | 1.00 |

*Fig. 7B*

Position 50 (279 human kappa sequences)

| RES | 50 |
|---|---|
| A | 0.00 |
| R | - |
| N | - |
| D | - |
| C | - |
| Q | - |
| E | - |
| G | - |
| H | - |
| I | 0.00 |
| L | 0.00 |
| K | - |
| M | - |
| F | - |
| P | 0.96 |
| S | - |
| T | - |
| W | - |
| Y | - |
| V | - |
| X | 0.03 |
| O | - |
| - | - |
| Z | - |
| B | - |
| Total | 1.00 |

*Fig. 7C*

Position 50 is highly conserved in all the sequences, but proline can be exchanged by Ile or Leu. The framework used for the light chain (6fab) does have an Ile at this position. If this position is compared to other structures the backbone torsions are the same for structures with a Pro and an Ile at this position.

Position 50 (153 human lambda sequences)

| RES | 183 |
|---|---|
| A | 0.06 |
| R | - |
| N | 0.00 |
| D | 0.21 |
| C | - |
| Q | 0.15 |
| E | 0.01 |
| G | 0.01 |
| H | - |
| I | 0.00 |
| L | 0.00 |
| K | 0.00 |
| M | - |
| F | 0.00 |
| P | 0.40 |
| S | 0.01 |
| T | 0.01 |
| W | - |
| Y | 0.00 |
| V | 0.08 |
| X | 0.02 |
| O | - |
| - | - |
| Z | - |
| B | 0.00 |
| Total | 1.00 |

*Fig. 7D*

Position 183 (1210 mouse sequences)

| RES | 183 |
|---|---|
| A | 0.16 |
| R | 0.00 |
| N | 0.00 |
| D | 0.13 |
| C | - |
| Q | 0.16 |
| E | 0.25 |
| G | 0.02 |
| H | 0.00 |
| I | - |
| L | - |
| K | 0.00 |
| M | - |
| F | - |
| P | 0.17 |
| S | 0.08 |
| T | 0.00 |
| W | - |
| Y | - |
| V | 0.00 |
| X | 0.02 |
| 0 | - |
| - | - |
| Z | - |
| B | - |
| Total | 1.00 |

Leu is seen in human sequences at this position, but never in murine sequences, for both human and murine Sequences P is the most frequently occuring residue at position 183.

*Fig. 7E*

Comments for pcDNA3:
5446 nucleotides

CMV promotor: bases 209-863
T7 promotor: bases 864-882
Polylinker: bases 889-994
Sp6 promotor: bases 999-1016
BGH poly A: bases 1018-1249
SV40 promotor: bases 1790-2115
SV40 origin of replication: bases 1984-2069
Neomycin ORF: bases 2151-2945
SV40 poly A: bases 3000-3372
ColE1 origin: bases 3632-4305
Ampicillin ORF: bases 4450-5310

*There is a ATG upstream of the Xba I site

//HUMANIZED ANTIBODIES THAT BIND TO THE ANTIGEN BOUND BY ANTIBODY NR-LU-13

CROSS-REFERENCE TO RELATED APPLICATION

This application is a continuation-in-part of U.S. patent application Ser. No. 08/660,362, filed Jun. 7, 1996, abandoned.

TECHNICAL FIELD

The present invention relates to humanized antibodies derived from chimeric antibody NR-LU-13 or other antibodies having the same or similar binding specificity, fragments thereof (including, e.g., variable regions and scFv's), conjugates (including fusion proteins) containing such humanized antibodies or fragments, and the use of such humanized antibodies or fragments in diagnostic and therapeutic pretargeting methods and compositions. The present invention also relates to the use of such humanized antibodies in conventional immunotherapeutic and immunodiagnostic methods and compositions, e.g., for tumor treatment and imaging.

BACKGROUND OF THE INVENTION

A specific antibody which has been previously disclosed to be an effective targeting moiety is NR-LU-10, a murine monoclonal antibody produced against a human cancer antigen. NR-LU-10 is a nominal 150 kilodalton molecular weight murine $IgG_{2b}$ pancarcinoma monoclonal antibody that recognizes an approximately 40 kilodalton glycoprotein antigen expressed on most carcinomas. NR-LU-10 has been safely administered to hundreds of patients in human clinical trials. However, its disadvantage is that it is a murine derived monoclonal antibody. This is disadvantageous because immunogenicity may potentially reduce targeting efficacy if the antibody is administered repeatedly. While therapeutic efficacy may be obtained using a single administration, multiple administrative protocols are currently favored.

As a means of reducing immunogenicity of murine antibodies, various methods have been reported in the literature. Such methods include the production of chimeric antibodies which contain murine variable regions and human constant regions, the production of single chain antibodies which comprise variable binding sequences derived from murine antibodies, the production of antigen-binding fragments of murine antibodies which because of their smaller size are potentially less immunogenic, the production of human monoclonal antibodies and the production of "humanized" antibodies.

Murine monoclonal antibodies may be made more human-like, e.g., by genetically recombining the nucleotide sequence encoding the murine Fv region (i.e., containing the antigen binding sites) or the complementarity determining regions thereof with nucleotide sequences encoding human constant region sequences (comprised in the Fc region of antibody). These antibodies are typically referred to as chimeric antibodies.

In this regard, a chimeric antibody derived from NR-LU-10, referred to as NR-LU-13, has previously been reported. This antibody contains the murine Fv region of NR-LU-10 and therefore comprises the same binding specificity as NR-LU-10. Thus, this chimeric antibody binds the NR-LU-10 antigen.

Humanization ideally provides an antibody that is non-immunogenic, with complete retention of the antigen-binding properties of the parent non-human antibody molecule. Non-immunogenicity allows for the administration of multiple dosages without adverse immunogenic reaction. Various methods for producing humanized antibodies have been reported in the literature. For example, humanized antibodies can potentially be produced: (a) by grafting only the non-human CDRs onto human framework and constant regions (Jones et al., Nature 321:522–25 (1986); Verhoeyen et al., Science 239:1534–1536 (1988)); or (b) by transplanting the entire non-human variable domains (to preserve ligand-binding properties) but also "cloaking" them with a human-like surface by replacement of exposed residues to reduce immunogenicity (also referred to as "veneered" antibodies) (Padlan, Molec. Immun. 28:489–498 (1991); Padlan, Molec. Immun. 31(3):169–217 (1994)).

Retention of murine residues within human variable region framework domains reportedly helps retain proper binding function of the resultant humanized antibody. Humanized antibodies have been reported to potentially decrease or eliminate the immunogenicity of the antibody in a host recipient, thereby permitting an increase in the bioavailability and a reduction in the possibility of adverse immune reactions, thus potentially enabling multiple antibody administrations. Also, the synthesis of scFv and antibody fragments such as Fv, Fd, Fab, Fab', and $F(ab)'_2$ fragments, derived from antibodies having a desired binding specificity comprises another known means of producing targeting moieties having lesser immunogenicity than intact antibodies. Essentially, single chain antibodies and antibody fragments because of their smaller size could be less immunogenic than intact antibodies.

It is also known that recombinant proteins, e.g., antibodies, are glycosylated differently in different host cells used for expression. Essentially, different host cells have a characteristic manner by which they glycosylate specific sites on proteins referred to as glycosylation sites or glycosylation motifs.

For example, plant cells primarily glycosylate proteins by O-linked glycosylation, whereas animal cells typically glycosylate proteins by N-linked and O-linked glycosylation. Also, the specific carbohydrates and the glycosylation pattern varies dependent upon the particular host cells.

It has been reported in the literature that oligosaccharides may be significant insofar as the targeting of proteins to specific sites. Moreover, it is also known that carbohydrates may elicit an immunogenic response. Accordingly, there is the possibility that proteins expressed in foreign host cells may elicit an immunogenic response because of carbohydrate residues which are introduced by the host cells used for expression. This is particularly problematic if the foreign host cells glycosylate very differently from humans. For example, there is the possibility that mammalian proteins expressed in plant cells may be immunogenic because plant cells glycosylate proteins very dissimilarly to mammalian cells.

Due to the difficulties related to immunogenicity of murine or chimeric antibodies that bind to the antigen bound by antibody NR-LU-13, there is a need in the art for improved compositions and methods. The present invention fulfills this need and further provides other related advantages.

SUMMARY OF THE INVENTION

It is an object of the invention to provide humanized antibodies derived from NR-LU-13 (or from other non-human antibodies which bind the antigen bound by NR-LU- 13) or fragments of such humanized antibodies, which exhibit reduced immunogenicity or toxicity in humans but retain the ability to bind the NR-LU-13 antigen.

It is another object of the invention to provide conjugates containing humanized antibodies derived from NR-LU-13 or from other non-human antibodies or fragments thereof which bind the antigen bound by NR-LU-13.

It is still another object of the invention to provide improved two-step pretargeting methods wherein the improvement comprises using as the targeting moiety a humanized antibody derived from NR-LU-1 3 or from another non-human antibody or fragments thereof which bind the antigen bound by NR-LU-13.

It is another object of the invention to provide improved three-step targeting methods wherein the improvement comprises using as the targeting moiety a humanized antibody derived from NR-LU-13 or from another non-human antibody or fragments thereof which bind the antigen bound by NR-LU-13.

It is yet another object of the invention to provide compositions for treatment or diagnosis which contain conjugates comprising humanized antibodies derived from NR-LU-13 or from other non-human antibodies or fragments thereof which bind the antigen bound by NR-LU-13.

It is a more specific object of the invention to provide conjugates comprising a humanized antibody derived from NR-LU-13 or a fragment thereof capable of binding the antigen bond by NR-LU-13, directly or indirectly attached to a member of a ligand or anti-ligand partner, preferably avidin or streptavidin or a fragment or derivative thereof capable of binding biotin.

It is another object of the invention to provide a conjugate comprising a humanized antibody derived from NR-LU-13 or a fragment thereof, which binds the antigen bound by NR-LU-13, for use in a method of treating or diagnosing cancer.

It is an even more specific object of the invention to produce specific humanized variable heavy and light sequences derived from NR-LU-13 referred to herein as humanized NRX451 or fragments thereof which bind to the antigen bound by NR-LU-13.

It is another specific object of the invention to provide compositions for treating or diagnosing cancer using humanized NRX451 or fragments thereof which bind the antigen bound by NR-LU-13.

It is another object of the invention to produce antibodies, in particular, murine, chimeric or humanized antibodies which have been mutated so as to eliminate one or more potential glycosylation sites and thereby reduce immunogenicity or toxicity.

It is another object of the invention to use antibodies, preferably humanized antibodies, which have been mutated to eliminate N-linked glycosylation or modified to reduce N-linked glycosylation, in pretargeting methods and conventional antibody therapy.

Thus, the present invention provides a humanized antibody or an antigen-binding humanized antibody fragment, wherein the antibody or the antibody fragment binds specifically to the antigen bound by antibody NR-LU-13, and preferably wherein the antibody or the antibody fragment either does not possess N-linked glycosylation or its N-linked glycosylation has been modified post expression to reduce immunogenicity or toxicity. The present invention also provides a method of reducing immunogenicity or toxicity of an antibody or an antigen-binding antibody fragment of IgG class, comprising the steps of: (a) selecting a host system for the characteristic that the system does not N-link glycosylate an antibody or an antibody fragment; and (b) expressing in the host system a nucleotide sequence comprising nucleic acids (e.g., DNA or RNA or functional equivalents) encoding an IgG antibody or an antigen-binding antibody fragment. The present invention further provides a method of eliminating N-linked glycosylation in an antibody or an antigen-binding antibody fragment of IgG class to reduce immunogenicity or toxicity, comprising expressing in a host system a nucleotide sequence comprising nucleic acids (e.g., DNA or RNA or functional equivalents) encoding an IgG antibody or an antigen-binding antibody fragment, wherein the host system does not N-link glycosylate the antibody or the antibody fragment. The present invention further provides a method of modifying the N-linked glycosylation of an antibody or an antigen-binding antibody fragment of IgG class (e.g., to reduce immunogenicity or toxicity), comprising subjecting the antibody or antibody fragment to a post expression modification that modifies the N-linked glycosylation. In a preferred embodiment, antibodies or fragments of IgG. class are modified chemically to reduce immunogenicity or toxicity.

Conjugates are provided comprising a humanized antibody or antibody fragment of the present invention, attached directly or indirectly to a ligand, anti-ligand, diagnostic agent or therapeutic agent. Pharmaceutical compositions are provided comprising an antibody or antibody fragment or conjugate of the present invention, in combination with a pharmaceutically acceptable carrier or diluent. An antibody or antibody fragment or conjugate or composition of the present invention is provided for use as a diagnostic or as a medicament; for use in diagnostic or therapeutic pretargeting methods; and in methods for the diagnosis of cancer, or in methods for the treatment of cancer. In diagnostic or therapeutic methods, an antibody or antibody fragment or conjugate or composition of the present invention is administered to a warm-blooded animal (such as a human) in an amount effective for diagnosis or therapy, respectively.

These and other embodiments of the present invention will become evident upon reference to the following detailed description and attached drawings.

BRIEF DESCRIPTION OF THE DRAWINGS

FIG. 2 contains the nucleotide and amino acid sequences of NR-LU-13 light chain (SEQ ID NOs.:16 and 17) and NR-LU-13 heavy chain variable regions (SEQ ID NOs 14 and 15).

FIG. 3 contains the amino acid sequence (SEQ ID NO:18) of the preferred humanized variable light sequence derived from NR-LU-13, referred to as humanized NRX451-light.

FIG. 4 contains the amino acid sequence (SEQ ID NO:19) of the preferred humanized variable heavy sequence derived from NR-LU-13, referred to as humanized NRX451-heavy.

FIG. 5 is an alignment of the heavy and light variable regions (SEQ ID NOs:17 and 18) of NR-LU-13 and the humanized heavy and light variable regions (SEQ ID NOs:15 and 19) derived therefrom, referred to as NRX451 heavy and NRX451 light.

FIG. 7a–7e contains amino acid frequencies for specific positions of human antibody sequences.

FIGS. 15a–5c depict the complement mediated cytotoxicity (C'MC) activity in unmodified and modified NRX451.

DETAILED DESCRIPTION OF THE INVENTION

Figure 1:
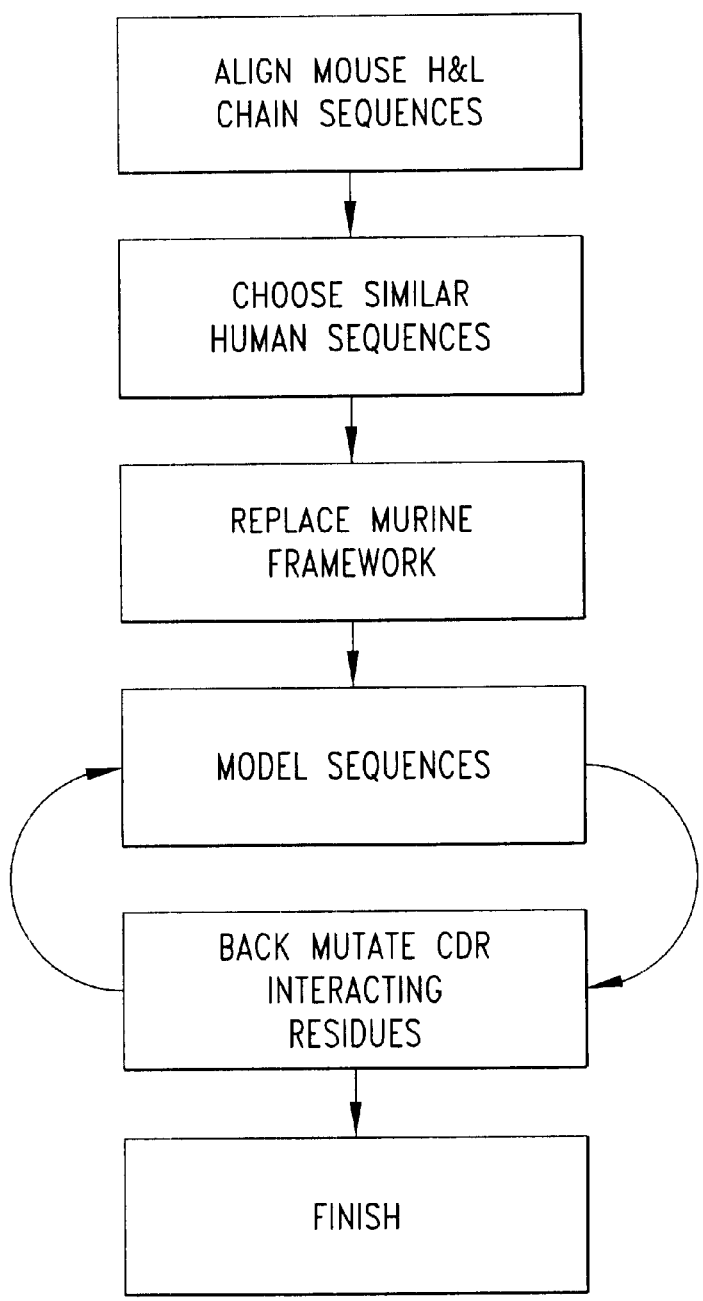
FIG. 1 depicts schematically the sequence analysis and computer modeling used to synthesize humanized antibodies from NR-LU-13.

Prior to setting forth the invention, it may be helpful to an understanding thereof to set forth definitions of certain terms to be used hereinafter.

Antibody—As used herein, includes both polyclonal and monoclonal antibodies; and may be an intact molecule, a fragment thereof (such as Fv, Fd, Fab, Fab' and F(ab)'$_2$ fragments, or multimers or aggregates of intact molecules and/or fragments; and may occur in nature or be produced, e.g., by immunization, synthesis or genetic engineering.

Protein—As used herein, includes proteins, polypeptides and peptides; and may be an intact molecule, a fragment thereof, or multimers or aggregates of intact molecules and/or fragments; and may occur in nature or be produced, e.g., by synthesis (including chemical and/or enzymatic) or genetic engineering.

Humanized antibody—This refers to an antibody derived from a non-human antibody (typically murine), or derived from a chimeric antibody, that retains or substantially retains the antigen-binding properties of the parent antibody but which is less immunogenic in humans. This may be achieved by various methods, including by way of example: (a) grafting only the non-human CDRs onto human framework and constant regions (humanization), or (b) transplanting the entire non-human variable domains, but "cloaking" them with a human-like surface by replacement of surface residues ("veneering"). Such methods are disclosed, for example, in Jones et al., *Nature* 321:522–525 (1986); Morrison et al., *Proc. Natl. Acad. Sci.* 81:6851–6855 (1984); Morrison and Oi, *Adv. Immunol.* 44:65–92 (1988); Verhoeyer et al., *Science* 239:1534–1536 (1988); Padlan, *Molec. Immun.* 28:489–498 (1991); Padlan, *Molec. Immun.* 31(3):169–217 (1994). In the present invention, humanized antibodies will include "humanized" and "veneered" antibodies, but exclude chimeric antibodies. A preferred method of humanization comprises alignment of the non-human heavy and light chain sequences to human heavy and light chain sequences, selection and replacement of the non-human framework with a human framework based on such alignment, molecular modeling to predict conformation of the humanized sequence and comparison to the conformation of the parent antibody, followed by repeated back mutation of residues in the CDR region which disturb the structure of the CDRs until the predicted conformation of the humanized sequence model closely approximates the conformation of the non-human CDRs of the parent non-human antibody. This method of humanization is depicted schematically in FIG. 1. Also, such humanized antibodies may be further derivatized to facilitate uptake and clearance, e.g., via Ashwell receptors, or other receptor mediated clearance mechanisms such as by the incorporation of galactose residues or other hexoses (e.g., U.S. Pat. Nos. 5,530,101 and 5,585,089).

Humanized antibody fragment—This refers to fragments, derived from a humanized antibody, which bind antigen and which may be derivatized to exhibit structural features that facilitate clearance and uptake, e.g., by the incorporation of galactose residues. This includes, e.g., F(ab), F(ab)'$_2$, scFv, light chain variable region, heavy chain variable region, and combinations thereof.

Complementarity Determining Region or CDR—The term CDR, as used herein, refers to amino acid sequences which together define the binding affinity and specificity of the natural Fv region of a native immunoglobulin binding site (Chothia et al., *J. Mol. Biol.* 196:901–917 (1987); Kabat et al., U.S. Dept. of Health and Human Services NIH Publication No. 91–3242 (1991)).

Framework Region or FR—The term FR, as used herein, refers to amino acid sequences interposed between CDRs. One function of these portions of the antibody is to hold the CDRs in appropriate orientation (allows for CDRs to bind antigen).

Constant Region or CR—The term CR as used herein refers to the portion of the antibody molecule which confers effector functions. In the present invention, murine constant regions are substituted by human constant regions. The constant regions of the subject humanized antibodies are derived from human immunoglobulins. The heavy chain constant region can be selected from any of the five isotypes: alpha, delta, epsilon, gamma or mu. Further, heavy chains of various subclasses (such as the IgG subclasses of heavy chains) are responsible for different effector functions and thus, by choosing the desired heavy chain constant region, chimeric antibodies with desired effector function can be produced. Preferred human constant regions are gamma 1 (IgG1), gamma 2 (IgG2), gamma 3 (IgG3) and gamma 4 (IgG4). Preferred is an Fc region of the gamma 1 (IgG1) isotype. The light chain constant region can be of the kappa or lambda type, and is preferably of the kappa type.

Chimeric antibody—This is an antibody containing sequences derived from two different antibodies (e.g., U.S. Pat. No. 4,816,567), which typically are of different species. Most typically chimeric antibodies comprise human and murine antibody fragments, generally human constant and murine variable regions.

NR-LU-10—A murine monoclonal antibody of the IgG2b isotype that recognizes an approximately 40 kilodalton glycoprotein antigen expressed on a large array of carcinomas. This antibody is a pancarcinoma antibody that has been safely administered in human clinical trials. The antigen bound by NR-LU-10 is expressed by cancers including, e.g., small cell lung, non-small cell lung, colon, breast, renal, ovarian, and pancreatic, among other carcinoma tissues. This antibody has been previously used as a targeting moiety in two-step and three-step pretargeting methods.

NR-LU-13—A chimeric monoclonal antibody containing the variable light and heavy regions of NR-LU-10 and human constant domains. This antibody binds the same antigen as NR-LU-10.

NR-LU-10 or NR-LU-13 antigen—These terms are used interchangeably and refer to the antigen bound by NR-LU-10 or NR-LU-13, which is an approximately 40 kilodalton glycoprotein antigen expressed by many carcinomas and noncancerous tissues.

Humanized NRX451 or humanized NRX451-light or humanized NRX451-heavy—These terms refer to specific humanized variable domain sequences derived from the Fv of NR-LU-13.

Humanized antibody or humanized antibody fragment conjugates—Conjugates which contain the humanized antibodies or humanized antibody fragments of the invention. These conjugates may include a ligand or anti-ligand, and/or an active agent as defined infra. The ligand, anti-ligand or active agent may be directly or indirectly attached to the humanized antibody or humanized antibody fragment, e.g., by the use of known linkers. These conjugates may exhibit or be derivatized to exhibit structural features that direct uptake and clearance thereof, e.g., by incorporation of hexoses such as galactose that direct liver uptake via Ashwell receptor mediated clearance.

Pretargeting—As defined herein, pretargeting involves target site localization of a targeting moiety that is conjugated with one member of a ligand/anti-ligand pair; after a time period sufficient for optimal target-to-non-target accumulation of this targeting moiety conjugate, active agent conjugated to the opposite member of the ligand/anti-ligand pair is administered and is bound (directly or indirectly) to the targeting moiety conjugate at the target site. Pretargeting optionally also involves an additional step of administering a clearing agent.

Targeting moiety—A molecule that binds to a defined population of cells. The targeting moiety may bind any target, such as a receptor, an oligonucleotide, an enzymatic substrate, an antigenic determinant, or other binding site present on or in the target cell population. The targeting moiety may be a protein, peptide, antibody and antibody fragments thereof, fusion proteins, and the like. Antibody is used throughout the specification as a prototypical example of a targeting moiety. Tumor is used as a prototypical example of a target.

Ligand/anti-ligand pair—A complementary/anti-complementary set of molecules that demonstrate specific binding, generally of relatively high affinity. Exemplary ligand/anti-ligand pairs include zinc finger protein/dsDNA fragment, enzyme/inhibitor, hapten/antibody, lectin/carbohydrate, ligand/receptor, and biotin/avidin or streptavidin. Biotin/avidin or streptavidin is used throughout the specification as a prototypical example of a ligand/anti-ligand pair.

Ligand—As defined herein, a "ligand" is a relatively small, soluble molecule that exhibits rapid serum, blood and/or whole body clearance when administered intravenously in an animal or human. Biotin and biotin analogs are used as the prototypical ligand. Analogs of biotin having reduced or enhanced binding affinity to avidin and streptavidin are well known in the art.

Anti-ligand—As defined herein, an "anti-ligand" demonstrates high affinity, and preferably, multivalent binding of the complementary ligand. Preferably, the anti-ligand when conjugated to a targeting moiety is large enough to avoid rapid renal clearance, and contains sufficient multivalence to accomplish cross-linking and aggregation of targeting moiety-ligand conjugates. Univalent anti-ligands are also contemplated by the present invention. Anti-ligands of the present invention may exhibit or be derivatized to exhibit structural features that direct the uptake thereof, e.g., by the incorporation of hexose residues that direct liver uptake. Avidin and streptavidin are used herein as prototypical anti-ligands.

Avidin—As defined herein, "avidin" includes avidin, streptavidin and derivatives and analogs thereof that are capable of high affinity, multivalent or univalent binding of biotin. Exemplary streptavidin molecules are described in U.S. Pat. Nos. 5,168,049 and 5,272,254.

Clearing agent—An agent capable of binding, complexing or otherwise associating with an administered moiety (e.g., targeting moiety-ligand, targeting moiety-anti-ligand or anti-ligand alone) present in the recipient's circulation, thereby facilitating circulating moiety clearance from the recipient's body, removal from blood circulation, or inactivation thereof in circulation. The clearing agent is preferably characterized by physical properties, such as size, charge, configuration or a combination thereof, that limit clearing agent access to the population of target cells recognized by a targeting moiety used in the same treatment protocol as the clearing agent.

Active agent—A diagnostic or therapeutic agent, including radionuclides, drugs, anti-tumor agents, cytokines, hormones, toxins and the like. Radionuclide therapeutic agents are prototypical active agents.

Target cell retention—The amount of time that a radionuclide or other therapeutic agent remains at the target cell surface or within the target cell. Catabolism of conjugates or molecules containing such therapeutic agents appears to be primarily responsible for the loss of target cell retention.

Conjugate—A conjugate is a molecule that is the combination of two or more molecules (or portions of any or all) that are directly (e.g., covalently or non-covalently bound) or indirectly (e.g., incorporated or bound indirectly) associated with one another. A conjugate includes chemical conjugates (covalently or non-covalently bound), fusion proteins and the like. Conjugates may possess a ligand or anti-ligand, and/or active agent.

Immunogenicity—A measure of the ability of a targeting protein or therapeutic moiety to elicit an immune response (humoral or cellular) when administered to a recipient. The present invention is concerned with the immunogenicity of conjugates and their component parts.

Aglycosylated antibody or aglycosylated humanized antibody—These terms refer to antibodies or humanized antibodies, or antigen binding fragments thereof which have been mutagenized by site-specific mutagenesis to modify amino acid residues in sites which would otherwise potentially be glycosylated so as to eliminate or reduce glycosylation.

Humanized antibody of reduced immunogenicity—This refers to a humanized antibody exhibiting reduced immunogenicity relative to the parent antibody, e.g., humanized antibody containing humanized NRX451-heavy and humanized NRX451-light sequences in relation to NR-LU-13.

Humanized antibody substantially retaining the binding properties of the parent antibody—This refers to a humanized antibody which retains the ability to specifically bind the antigen recognized by the parent antibody used to produce such humanized antibody. For example, humanized antibodies which substantially retain the binding properties of NR-LU-13 specifically bind to an approximately 40 kilodalton protein expressed by many carcinomas, and more preferably to the same epitope as NR-LU-13. Preferably the humanized antibody will exhibit the same or substantially the same antigen-binding affinity as the parent antibody. Generally, the affinity will be within about the same order of magnitude as the affinity of the parent antibody. Methods for assaying antigen-binding affinity are well known in the art and include half-maximal binding assays, competition assays, and Scatchard analysis.

Where applicable, the above-recited definitions include functional equivalents, i.e., molecules that differ in length, structure, components, etc., but which nevertheless are able to perform or achieve one or more of the functions of the defined molecule. Functional equivalents of the aforementioned defined molecules include functional equivalents of antibodies or antibody fragments of the present invention. One functional equivalent is a "mimetic" compound, i.e., an organic chemical construct designed to mimic the proper configuration and/or orientation for antigen binding. Another functional equivalent is a short polypeptide designated as a "minimal" polypeptide, constructed using computer-assisted molecular modeling and mutants having altered binding affinity, which minimal polypeptides exhibit the antigen binding affinity of the antibody.

As noted above, the subject invention is directed toward the production of humanized antibodies, and antigen-binding fragments thereof, derived from NR-LU-13 or other non-human antibodies which bind to the antigen recognized by NR-LU-13 (at the same or different epitopes), and their usage, especially in two-step and three-step pretargeting methods. Moreover, given that the subject humanized antibodies will typically contain human constant regions, they also may be used as therapeutic antibodies. Specifically, humanized antibodies which contain human constant regions typically elicit human effector functions, e.g., complement mediated cytotoxicity (C'MC) and antibody dependent cell-mediated cytotoxicity (ADCC) activity. Such activity may result in direct tumor cell lysis by complement proteins or ADCC effector cells, NK polymorphonuclear cells and monocytes. Also, such activity may result in the induction of an inflammatory response as typified by infiltration of inflammatory effector cells, macrophage and polymorphonuclear leukocytes. Therefore, these humanized antibodies may potentiate tumor cell lysis absent the need for attachment to another active agent, e.g., a radionuclide or a toxin.

Alternatively, humanized antibodies, and antigen-binding fragments, with or without effector sequences may be attached to active agents to effect a desired therapeutic function.

As previously described, NR-LU-13 is a chimeric antibody containing murine Fv sequences and human constant domain sequences. NR-LU-13 is an antibody that binds the NR-LU-13 antigen at the same epitope as NR-LU-10. NR-LU-10 is a pancarcinoma antibody which is a murine monoclonal antibody of the IgG2b isotype having a molecular weight of 150 kilodaltons. As discussed, this monoclonal antibody as well as the Fab fragment thereof have been safely administered to many hundreds of patients in human clinical trials.

Radioimmunoassay, immunoprecipitation and Fluorescence-Activated Cell Sorting (FACS) analysis have been used to determine reactivity profiles of NR-LU-10. The NR-LU-10 target antigen is present on either fixed cultured cells or in detergent extracts of various types of cancer cells. For example, the NR-LU-10 antigen is expressed by small cell lung, non-small cell lung, colon, breast, renal, ovarian, pancreatic, and other carcinoma tissues. Tumor reactivity of the NR-LU-10 antibody is set forth in Table A, while NR-LU-10 reactivity with normal tissues is set forth in Table B. The values in Table B are obtained as described below. Positive NR-LU-10 tissue reactivity indicates NR-LU-10 antigen expression by such tissues. The NR-LU-10 antigen has been further described by Varki et al., "Antigens Associated with a Human Lung Adenocarcinoma Defined by Monoclonal Antibodies," *Cancer Research* 44: 681–687 (1984), and Okabe et al., "Monoclonal Antibodies to Surface Antigens of Small Cell Carcinoma of the Lung," *Cancer Research* 44: 5273–5278 (1984).

The tissue specimens were scored in accordance with three reactivity parameters: (1) the intensity of the reaction; (2) the uniformity of the reaction within the cell type; and (3) the percentage of cells reactive with the antibody. These three values are combined into a single weighted comparative value between 0 and 500, with 500 being the most intense reactivity. This comparative value facilitates comparison of different tissues. Table B includes a summary reactivity value, the number of tissue samples examined and the number of samples that reacted positively with NR-LU-10.

Methods for preparing antibodies that bind to epitopes of the NR-LU-10 antigen are also known and are described in U.S. Pat. No. 5,084,396. Briefly, such antibodies may be prepared by the following procedure:

absorbing a first monoclonal antibody directed against a first epitope of a polyvalent antigen onto an inert, insoluble matrix capable of binding immunoglobulin, thereby forming an immunosorbent;

combining the immunosorbent with an extract containing polyvalent NR-LU-10 antigen, forming an insolubilized immune complex wherein the first epitope is masked by the first monoclonal antibody;

immunizing an animal with the insolubilized immune complex;

fusing spleen cells from the immunized animal to myeloma cells to form a hybridoma capable of producing a second monoclonal antibody directed against a second epitope of the polyvalent antigen;

culturing the hybridoma to produce the second monoclonal antibody; and collecting the second monoclonal antibody as a product of the hybridoma.

Monoclonal antibodies NR-LU-01, NR-LU-02, NR-LU-03 and NR-LU-06 prepared in accordance with the procedures described in the aforementioned patent, are exemplary antibodies which bind the same cancer antigen as NR-LU-10, which are suitable for use in pretargeting methods.

Additional antibodies reactive with the NR-LU-10 antigen may also be prepared by standard hybridoma production and screening techniques. Any hybridoma clones so produced and identified may be further screened as described above to verify antigen and tissue reactivity.

TABLE A

| Organ/Cell Type Tumor | #Pos/Exam | Intensity[a] Avg. | Intensity[a] Range | Percent[b] Avg. | Percent[b] Range | Uniformity[c] Avg. | Uniformity[c] Range |
|---|---|---|---|---|---|---|---|
| Pancreas Carcinoma | 6/6 | 3 | 3 | 100 | 100 | 2.3 | 2.3 |
| Prostate Carcinoma | 9/9 | 2.8 | 2.3 | 95 | 80–100 | 2 | 1.3 |
| Lung Adeno-carcinoma | 8/8 | 3 | 3 | 100 | 100 | 2.2 | 1.3 |
| Lung Small Cell Carcinoma | 2/2 | 3 | 3 | 100 | 100 | 2 | 2 |
| Lung Squamous Cell Carcinoma | 8/8 | 2.3 | 2.3 | 73 | 5–100 | 1.8 | 1.3 |
| Renal Carcinoma | 8/9 | 2.2 | 2.3 | 83 | 75–100 | 1 | 1 |
| Breast Adeno-carcinoma | 23/23 | 2.9 | 2.3 | 97 | 75–100 | 2.8 | 1.3 |
| Colon Carcinoma | 12/12 | 2.9 | 2.3 | 98 | 95–100 | 2.9 | 2.3 |
| Malignant Melanoma Ocular | 0/2 | 0 | 0 | 0 | 0 | 0 | 0 |
| Malignant Melanoma | 0/11 | 0 | 0 | 0 | 0 | 0 | 0 |
| Ovarian Carcinoma | 35/35 | 2.9 | 2.3 | 100 | 100 | 2.2 | 1.3 |
| Undifferentiated Carcinoma | 1/1 | 2 | 2 | 90 | 90 | 2 | 2 |
| Osteosarcoma | 1/1 | 2 | 2 | 20 | 20 | 1 | 1 |
| Synovial Sarcoma | 0/1 | 0 | 0 | 0 | 0 | 0 | 0 |
| Lymphoma | 0/2 | 0 | 0 | 0 | 0 | 0 | 0 |
| Liposarcoma | 0/2 | 0 | 0 | 0 | 0 | 0 | 0 |
| Uterine Leiomyosarcoma | 0/1 | 0 | 0 | 0 | 0 | 0 | 0 |

TABLE B

| Organ Cell Type | #Pos/Exam | Summary Reactivity |
|---|---|---|
| Adenoid | | |
| Epithelium | 3/3 | 433 |
| Lymphoid Follicle-Central | 0/3 | 0 |
| Lymphoid Follicle-Peripheral | 0/3 | 0 |
| Mucus Gland | 2/2 | 400 |
| Adipose Tissue | | |
| Fat Cells | 0/3 | 0 |
| Adrenal | | |
| Zona Fasciculata Cortex | 0/3 | 0 |
| Zona Glomerulosa Cortex | 0/3 | 0 |
| Zona Reticularis Cortex | 0/3 | 0 |
| Medulla | 0/3 | 0 |
| Aorta | | |
| Endothelium | 0/3 | 0 |
| Elastic Interna | 0/3 | 0 |
| Tunica Adventitia | 0/3 | 0 |
| Tunica Media | 0/3 | 0 |
| Brain-Cerebellum | | |
| Axons, Myelinated | 0/3 | 0 |
| Microglia | 0/3 | 0 |
| Neurons | 0/3 | 0 |
| Purkenje's Cells | 0/3 | 0 |
| Brain-Cerebrum | | |
| Axons, Myelinated | 0/3 | 0 |
| Microglia | 0/3 | 0 |
| Neurons | 0/3 | 0 |
| Brain-Midbrain | | |
| Axons, Myelinated | 0/3 | 0 |
| Microglia | 0/3 | 0 |
| Neurons | 0/3 | 0 |
| Colon | | |
| Mucosal Epithelium | 3/3 | 500 |
| Muscularis Externa | 0/3 | 0 |
| Muscularis Mucosa | 0/3 | 0 |
| Nerve Ganglia | 0/3 | 0 |
| Serosa | 0/1 | 0 |
| Duodenum | | |
| Mucosal Epithelium | 3/3 | 500 |
| Muscularis Mucosa | 0/3 | 0 |
| Epididymis | | |
| Epithelium | 3/3 | 419 |
| Smooth Muscle | 0/3 | 0 |
| Spermatozoa | 0/1 | 0 |
| Esophagus | | |
| Epithelium | 3/3 | 86 |
| Mucosl Gland | 2/2 | 450 |
| Smooth Muscle | 0/3 | 0 |
| Gall Bladder | | |
| Mucosal Epithelium | 0/3 | 467 |
| Smooth Muscle | 0/3 | 0 |
| Heart | | |
| Myocardium | 0/3 | 0 |
| Serosa | 0/1 | 0 |
| Ileum | | |
| Lymph Node | 0/2 | 0 |
| Mucosal Epithelium | 0/2 | 0 |
| Muscularis Externa | 0/1 | 0 |
| Muscularis Mucosa | 0/2 | 0 |
| Nerve Ganglia | 0/1 | 0 |
| Serosa | 0/1 | 0 |
| Jejunum | | |
| Lymph Node | 0/1 | 0 |
| Mucosal Epithelium | 2/2 | 400 |
| Muscularis Externa | 0/2 | 0 |
| Muscularis Mucosa | 0/2 | 0 |
| Nerve Ganglia | 0/2 | 0 |
| Serosa | 0/1 | 0 |
| Kidney | | |
| Collecting Tubules | 2/3 | 160 |
| Distal Convoluted Tubules | 3/3 | 500 |
| Glomerular Epithelium | 0/3 | 0 |
| Mesangial | 0/3 | 0 |
| Proximal Convoluted Tubules | 3/3 | 500 |
| Liver | | |
| Bile Duct | 3/3 | 500 |

TABLE B-continued

| Organ Cell Type | #Pos/Exam | Summary Reactivity |
|---|---|---|
| Central Lobular Hepatocyte | 1/3 | 4 |
| Periportal Hepatocyte | 1/3 | 40 |
| Kupffer Cells | 0/3 | 0 |
| Lung | | |
| Alveolar Macrophage | 0/3 | 0 |
| Bronchial Epithelium | 0/2 | 0 |
| Bronchial Smooth Muscle | 0/2 | 0 |
| Pneumocyte Type I | 3/3 | 354 |
| Pneumocyte Type II | 3/3 | 387 |
| Lymph Node | | |
| Lymphoid Follicle-Central | 0/3 | 0 |
| Lymphoid Follicle-Peripheral | 0/3 | 0 |
| Mammary Gland | | |
| Aveolar Epithelium | 3/3 | 500 |
| Duct Epithelium | 3/3 | 500 |
| Myoepithelium | 0/3 | 0 |
| Muscle Skeletal | | |
| Muscle Fiber | 0/3 | 0 |
| Nerve | | |
| Axon Myelinated | 0/2 | 0 |
| Endoneurium | 0/2 | 0 |
| Neurolemma | 0/2 | 0 |
| Neuron | 0/2 | 0 |
| Perineurium | 0/2 | 0 |
| Ovary | | |
| Corpus Luteum | 0/3 | 0 |
| Epithelium | 1/1 | 270 |
| Granulosa | 1/3 | 400 |
| Serosa | 0/3 | 0 |
| Theca | 0/3 | 0 |
| Oviduct | | |
| Epithelium | 1/1 | 500 |
| Smooth Muscle | 0/3 | 0 |
| Pancreas | | |
| Acinar Cell | 3/3 | 500 |
| Duct Epithelium | 3/3 | 500 |
| Islet Cell | 3/3 | 500 |
| Peritoneum | | |
| Mesothelium | 0/1 | 0 |
| Pituitary | | |
| Adenohypophysis | 2/2 | 500 |
| Neurohypophysis | 0/2 | 0 |
| Placenta | | |
| Trophoblasts | 0/3 | 0 |
| Prostate | | |
| Concretions | 0/3 | 0 |
| Glandular Epithelium | 3/3 | 400 |
| Smooth Muscle | 0/3 | 0 |
| Rectum | | |
| Lymph Node | 0/2 | 0 |
| Mucosal Epithelium | 0/2 | 0 |
| Muscularis Externa | 0/1 | 0 |
| Muscularis Mucosa | 0/3 | 0 |
| Nerve Ganglia | 0/3 | 0 |
| Salivary Gland | | |
| Acinar Epithelium | 3/3 | 500 |
| Duct Epithelium | 3/3 | 500 |
| Skin | | |
| Apocrine Glands | 3/3 | 280 |
| Basal Layer | 3/3 | 33 |
| Epithelium | 1/3 | 10 |
| Follicle | 1/1 | 190 |
| Stratum Corneum | 0/3 | 0 |
| Spinal Cord | | |
| Axons Myelinated | 0/2 | 0 |
| Microglial | 0/2 | 0 |
| Neurons | 0/2 | 0 |
| Spleen | | |
| Lymphoid Follicle-Central | 0/3 | 0 |
| Lymphoid Follicle-Peripheral | 0/3 | 0 |
| Trabecular Smooth Muscle | 0/3 | 0 |
| Stomach | | |
| Chief Cells | 3/3 | 290 |
| Mucosal Epithelium | 3/3 | 367 |
| Muscularis Mucosa/Externa | 0/3 | 0 |
| Parietal Cells | 3/3 | 290 |
| Smooth Muscle | 0/3 | 0 |
| Stromal Tissue | | |
| Adipose | 0/63 | 0 |
| Arteriolar Smooth Muscle | 0/120 | 0 |
| Endothelium | 0/120 | 0 |
| Fibrous Connective Tissue | 0/120 | 0 |
| Macrophages | 0/117 | 0 |
| Mast Cells/Eosinophils | 0/86 | 0 |
| Testis | | |
| Interstitial Cells | 0/3 | 0 |
| Sertoli Cells | 3/3 | 93 |
| Thymus | | |
| Hassal's Epithelium | 3/3 | 147 |
| Hassal's Keratin | 3/3 | 333 |
| Lymphoid Cortex | 0/3 | 0 |
| Lymphoid Medulla | 3/3 | 167 |
| Thyroid | | |
| C-cells | 0/3 | 0 |
| Colloid | 0/3 | 0 |
| Follicular Epithelium | 3/3 | 500 |
| Tonsil | | |
| Epithelium | 1/3 | 500 |
| Lymphoid Follicle-Central | 0/3 | 0 |
| Lymphoid Follicle-Peripheral | 0/3 | 0 |
| Mucus Gland | 1/1 | 300 |
| Striated Muscle | 0/3 | 0 |
| Umbilical cord | | |
| Epithelium | 0/3 | 0 |
| Urinary Bladder | | |
| Mucosal Epithelium | 3/3 | 433 |
| Serosa | 0/1 | 0 |
| Smooth Muscle | 0/3 | 0 |
| Uterus | | |
| Endometrial Epithelium | 3/3 | 500 |
| Endometrial Glands | 3/3 | 500 |
| Smooth Muscle | 0/3 | 0 |
| Vagina/Cervix | | |
| Epithelial Glands | 1/1 | 500 |
| Smooth Muscle | 0/2 | 0 |
| Squamous Epithelium | 1/1 | 200 |

However, while the NR-LU-13 antibody and other antibodies of non-human origin which bind the NR-LU-10 antigen possess therapeutic and diagnostic utility, especially as targeting moieties in pretargeting methods, they suffer from one potential disadvantage. Specifically, because they contain non-human (e.g., murine) sequences, they may be immunogenic in humans. This is disadvantageous because such immunogenicity may reduce targeting efficacy upon repeated administration of antibody.

Thus, the present invention provides targeting moieties having substantially the same antigen binding properties as NR-LU-13, but which exhibit reduced immunogenicity. More specifically, the present invention provides humanized antibodies, and antigen-binding humanized antibody fragments, derived from NR-LU-13 or other non-human antibodies which specifically bind the same cancer antigen recognized by NR-LU-13, and more preferably the same epitope. As used herein, a humanized antibody, or humanized antibody fragment, that "binds specifically" to the antigen bound by antibody NR-LU-13 means that the antibody or antibody fragment has a binding affinity of at least about $10^4$ $M^{-1}$. Preferably, the binding affinity is at least about $10^6$ $M^{-1}$, and more preferably at least about $10^8$ $M^{-1}$.

As discussed, it has been reported in the literature that humanized antibodies may potentially be derived from murine antibodies which exhibit the same or substantially some antigen-binding characteristics, but which exhibit reduced immunogenicity.

Humanized antibodies may be produced by a variety of methods. These humanization methods include: (a) grafting only non-human CDRs onto human framework and constant regions (e.g., Jones et al., *Nature* 321:522–525 (1986) (conventional humanized antibodies); Verhoeyen et al., *Science* 239:1534–1536 (1988); and (b) transplanting the entire non-human variable domains, but cloaking (veneering) these domains by replacement of exposed residues (to reduce immunogenicity) (e.g., Padlan, *Molec. Immun.* 28:489–498 (1991) (veneered antibodies). As noted supra, humanized antibodies as defined herein includes both conventional "humanized" and "veneered antibodies".

Within the present invention, the election was made to humanize NR-LU-13 using a humanization protocol which involves a series of sequence analysis and molecular modeling steps. This protocol is depicted schematically in FIG. 1. Essentially, it comprises comparison of the murine heavy and light variable chain sequences with a database of human heavy and light variable region sequences; selection of the most similar human framework sequences; replacement of selected framework residues based on sequence similarity; generation of molecular models corresponding to parent murine and putative humanized sequences; back mutating to modify the residues believed to perturb conformation of complementarity determining regions (CDRs) by comparison to the molecular model corresponding to parent murine sequence; constructing a molecular model based on the modified sequence; and comparison of this model with the parent murine sequence. This analysis is continued until the conformation of the CDRs in the humanized model closely match the CDR conformation in the parent murine model. This protocol may also be utilized to humanize other non-human (e.g., murine) antibodies specific for the antigen bound by NR-LU-13, and more preferably antibodies which bind the same epitope as NR-LU-13.

More specifically for the humanization of NR-LU-13, DNA fragments encoding the NR-LU-13 antibody were cloned, and these DNA fragments were sequenced by known methods, including the entire variable heavy and light domains which includes the complementarity determining regions (CDRs) and framework regions (FRs). The amino acid sequences encoding the murine variable heavy and light sequences were compared to a database of human sequence pairs (immunoglobulin light and heavy chains originating from the same clone). The DNA sequences and deduced amino acid sequences of the cloned heavy and light chain variable regions of NR-LU-13 are depicted in FIG. 2. The immunoglobulin sequence data used for such comparison was obtained from Kabat et al., "Sequences of Proteins of Immunological Interest," U.S. Dept. Health and Human Services, Fifth Ed. 1991. Structural data was obtained from Bernstein et al., "The protein databank: A computer based archival file for macromolecular structures, *J Mol. Biol.* 112:535–542 (1977).

After sequence comparison, the most identical human antibody sequence was selected to supply the initial framework for the "grafted" antibody. The most identical sequence pair was found to be that of the clone R3.5H5G' CL (Manheimer-Lory et al., *J Exp. Med.*, 174 (Dec. 1991) 1639–1642). The sequence of the original murine CDRs derived from NR-LU-13 were then transferred to the selected human framework structure. This process resulted in an initial putative humanized Fv sequence. The initial putative humanized sequence underwent a series of mutations as previously described.

The initial putative humanized sequence was then "refined" by testing the sequence in three-dimensional models. A molecular model was constructed of the original murine sequence and the initial humanized sequence. Equivalent residue positions in the murine model and the humanized model were compared. Residues in the humanized model which were predicted to perturb the structure of the CDRs were "back mutated." A molecular model was then constructed of the modified putative humanized sequence and again compared to the murine molecular model. This cycle of putative humanized sequence molecular modeling and "back mutation" followed by comparison of the resultant modified humanized sequence model to the murine model is repeated until the conformation of the CDRs in the humanized model closely matches the CDR conformation of the murine model. This humanization protocol is depicted schematically in FIG. 1.

Using this methodology, with variable heavy and light sequences derived from NR-LU-13 (referred to as NRX451-light and NRX451-heavy sequences), humanized NRX451 heavy and light sequences were obtained. These humanized light and heavy sequences are respectively set forth in FIG. 3 and FIG. 4. In both of these figures, the variable heavy or light framework residues which vary from the parent NRX451 heavy and light murine sequence residues are in bold type.

It can be seen upon review of FIGS. 3 and 4 that the humanized variable heavy and light sequences (referred to as NRX451-heavy and NRX451-light sequences) differ from the parent murine antibody variable sequences mainly at the base of the Fv domain towards the C portion of the Fab fragment. The numbering of the subject NRX451 murine and humanized sequences is according to UDB numbering. These humanized variable heavy and light sequences are intended to result in humanized antibodies exhibiting less immunogenicity than NR-LU-13.

While it is intended that the NRX451 sequences (given their sequence similarity to human immunoglobulins) depicted in FIGS. 3 and 4 result in antibodies eliciting reduced immunogenicity in humans (compared to murine NR-LU-10 or chimeric NR-LU-13) and may moreover exhibit enhanced serum half-life, other modifications of the above-identified NRX451 sequences are within the scope of the present invention. For example, these humanized sequences may be further modified by deletion, addition or substitution mutation. In particular, they may be modified by the substitution of one or more exposed framework residues according to the method of Padlan, *Molec. Immunol.* 28:489–498 (1991), referenced herein. For example, a particular amino acid residue contemplated for substitution is the cysteine at position 60 of the heavy chain by another amino acid, e.g., serine.

In particular, the invention embraces substitution modifications which do not substantially adversely affect antigen binding. For example, this includes conservative amino acid substitutions, e.g., the substitution of an acidic amino acid by another acidic amino acid. Conservative amino acid substitution mutations are well known in the art.

Moreover, the invention specifically embraces NRX451-heavy and NRX451-light sequences and fragments thereof which are contained in pNRX451 which is a plasmid. A plasmid of NRX451 (pNRX451) is a mammalian expression vector derived from pcDNA3 (Invitrogen) containing cDNA encoding humanized heavy and light chains.

Also, they may be truncated by the deletion of one or more amino acid residues to produce functional (antigen-binding) humanized sequences. For example, it has been observed during expression of the subject humanized antibodies in CHO and insect cells that fragments (apparently produced because of a cellular cleavage mechanism or the purification method) which lack residues of the subject humanized NRX451 sequences are functional, i.e., they still bind the NR-LU-13 antigen. In particular, it is observed that humanized Fv sequences containing the above humanized sequences, but lacking the first seven N-terminal residues of the NRX451 humanized heavy chain sequence are functional. Based on these results, it is expected that other deletions, e.g., other N-terminal and C-terminal deletions of the subject humanized NRX451, should also be functional (bind antigen). Functional deletions can be identified by sequential expression of various deletions, and screening the resultant deletion to determine its ability to bind the NR-LU-13 antigen. As described below, mutated antibody sequences may be expressed in any of a variety of host systems, e.g., mammalian cells (such as CHO cells), insects, plant cells, transgenic plants and transgenic animals.

As noted above, the subject invention further relates to the modification of antibodies (especially IgG class) to eliminate N-linked glycosylation (i.e., pre-expression modification of antibodies to prevent N-linked glycosylation) or to modify N-linked glycosylation (i.e., post expression modification of N-linked glycosylation of antibodies). As described herein, elimination or modification of N-linked glycosylation has the beneficial property of reducing immunogenicity and/or toxicity. Antibodies are glycoproteins which are glycosylated at characteristic sites dependent upon their isotype. For example, IgGs are N-link glycosylated as a bianternary complex at Asn-Xaa-Ser(Thr) motif in each of the $C_H2$ domains (wherein in this motif Xaa is any amino acid and Ser and Thr are interchangeable). Glycosylation occurs as a post translational event when oligosaccharides, ranging in size from 8 to 90 saccharides, are N-linked to the motif at the Asn residue (297).

The effects of glycosylation on the tertiary structure of antibodies, and specifically the Fc region thereof, is known to be structurally significant. For example, such significance has been revealed by NMR studies (see R. A. Dwek et al, *J Anat.* 187:279–292 (1995), "Glycobiology: The function of sugar in the IgG molecule". Moreover, glycosylation is significant as C1q binding and antibody binding to monocytes is significantly reduced in glycosylated monoclonal antibodies.

Also, modification of glycosylation patterns in IgG has been reported to be associated with many diseases including rheumatoid arthritis, age and pregnancy (See Dwek et al, Ibid.). Consequently, in the commercial production of monoclonal antibodies glycosylation has recently become a concern. More specifically, inappropriate glycosylation patterns have become a concern because monoclonal antibody production has expanded to include new organisms, many of which glycosylate proteins dissimilarly in relation to human cells. Previously, monoclonal antibodies were only expressed in mammalian cells. However, with the development of new and improved vector systems, protein purification and culturing methods, antibodies, e.g., murine, chimeric and humanized antibodies may be expressed in many hosts and host cell systems, e.g., mammalian, yeast, insect and plant cells. While this offers significant advantages, e.g., insects typically provide for high expression of recombinant proteins; there is at least one potential problem with expressing proteins in different hosts. Specifically, while the fidelity of protein expression in different hosts is well controlled, post translational modification is an innate property of the pertinent host cell line. In general, host cells glycosylate proteins in a characteristic manner, i.e., glycosylation pattern.

The post translational process of glycosylation in novel expression systems has been believed to be potentially problematic because it may affect the biodistribution of the resultant glycoprotein because of altered carbohydrate recognition. In this regard, it is widely accepted that oligosaccharides act as recognition elements. For example, many animal proteins isolated from cells and tissues have sequence motifs that recognize carbohydrate domains. Therefore, modification of glycosylation sites would be expected to alter the biodistribution of a protein.

Moreover, because oligosaccharides affect antibody structure, modification of glycosylation sites might be expected to potentially adversely affect the structure and the binding conformation of the antibody molecule. However, as shown in the disclosure of the present invention, it was discovered that elimination or modification of antibodies' carbohydrate moieties (particularly humanized antibodies to the NR-LU- 13 antigen) had beneficial rather than deleterious effects.

In order to reduce or eliminate immunogenicity or toxicity of IgG class antibodies, the present invention provides for pre-expression or post expression modification of antibodies to prevent or modify N-linked glycosylation. The elimination of potential glycosylation sites in monoclonal antibodies, e.g., chimeric and humanized antibodies and fragments thereof, may be accomplished by site specific mutagenesis. Specifically, the present invention includes site-specifically mutagenizing DNA sequences encoding antibodies or antibody fragments, preferably humanized antibodies or humanized variable sequences which introduce substitution mutations in or proximate to one or more glycosylation sites.

This is accomplished by site-specific mutagenesis of a codon in a DNA encoding an immunoglobulin sequence which corresponds to an amino acid residue contained within a glycosylation site, or which is sufficiently proximate thereto such that the modification of such amino acid results in the elimination of glycosylation of said glycosylation site. In general, this will involve site specific mutagenesis of the Asn-Xaa-Ser(Thr) glycosylation motifs which are present in immunoglobulins. For example, such Asn-Xaa-Ser(Thr) motifs are known to be present in the $C_H2$ domain of IgGs at conserved sites in the antibody molecule.

Elimination of glycosylation at such site(s) is accomplished by site specific mutagenesis of a glycosylation site contained in an antibody sequence in order to alter (substitute or delete) one or more of the amino acids contained therein and thereby prevent glycosylation at such site. Methods for introducing site specific mutations in DNA sequences at a desired site are well known in the art.

In general, therefore the method will comprise cloning a DNA sequence encoding a desired antibody, identifying the glycosylation motifs contained therein, and modifying one or more codons in said glycosylation motifs so as to introduce an amino acid substitution mutation such that upon expression of such DNA in a selected host cell the resultant antibody is not glycosylated at said site.

As noted, methods of site specific mutagenesis are well known in the art. In site-directed mutagenesis, the substitution is accomplished by chemically synthesizing an oligonucleotide incorporating the desired base change, hybridizing the oligonucleotide to the DNA encoding sequence to be altered, and extending the mismatched primer with DNA polymerase to create the new gene sequence. The mutated gene can subsequently be inserted into a suitable host organism or expression system to yield the mutant DNA or RNA or produce the altered protein product. Typically, such modification will substitute the asparagine residue in a glycosylation motif with another amino acid.

Alternatively, a glycosylation motif can be changed by deletion of the DNA codon for either asparagine or serine/threonine in the sequence, Asn-Xaa-Ser/Thr, which would prevent glycosylation from occurring at that site. For example, DNA sequences between two unique restriction sites flanking the glycosylation site can be chemically synthesized without the asparagine codon. The original wild type DNA sequence can then be replaced with the altered sequence in the plasmid construct using the two restriction sites.

For example, one means comprises the synthesis of two different oligonucleotides that overlap the targeted sequence which is to be modified, i.e., the portion of the DNA which encodes the Asn-Xaa-Ser(Thr) motif, one of which contains the mutation which is to be inserted; conducting two separate polymerase chain reactions wherein in the first reaction the mutant oligonucleotide is amplified; and conducting a second polymerase chain reaction wherein a PCR "sewing reaction" is performed. This essentially results in the combination of the mutated oligonucleotide with the second oligonucleotide primer to create a single mutant cDNA which contains the desired mutation. The amplified cDNA which contains the mutation is then inserted into the appropriate insertion site in a vector which contains the original (non-mutated) antibody DNA sequence. The resultant clones are then sequenced to verify that the mutation has been inserted at the appropriate site.

Mutations of glycosylation sites may be introduced into any cloned antibody sequence, e.g., murine antibody sequences, chimeric antibody sequences and humanized antibody sequences. The resultant mutated antibody DNA sequences are then expressed in desired expression systems to obtain antibodies having reduced or no glycosylation.

Alternatively, N-linked glycosylation (and optionally O-linked glycosylation) of an IgG antibody may be modified post expression. It is further within the scope of the present invention to modify an antibody (or fragment) both pre-expression and post expression. Modification post expression means eliminating or modifying (e.g., reducing) N-linked glycosylation post expression. Post expression modifications include: expression of antibody sequences in host systems (expression systems) that do not N-link glycosylate an antibody or antibody fragment; chemical modification; and enzymatic modification. Host systems are discussed in more detail below. Glycosylation sites on an antibody may be removed enzymatically. There are a number of glycosidases capable of cleaving the carbohydrates on protein molecules. Examples of some N glycosidases commonly used for deglycosylation of N-linked carboxyhydrates includes: Endoglycosidase H, which cleaves high mannose type and hybrid oligosaccharide chains; Endoglycosidase F, which cleaves biantennary complex type oligosaccharide; and Peptide N-glycosidase F, which cleaves tri and tetraantennary complex type chains as well as others cleaved by the above described N-glycosidases. O-linked carbohydrates can also be removed enzymatically using O-glycanase, and the like. Glycosidases are commercially available (e.g., Sigma Chemical Co., St. Louis, Mo.). These enzymes and others known to one of ordinary skill in the art are capable of removing some of the specified carbohydrates using mild reaction conditions between pH 4.0 and 9.0. For example, PNGase F is most active at pH 8.0, but will function adequately±one pH unit.

The chemical modification methodology of the present invention, for modifying antibodies to reduce immunogenicity and/or toxicity, is oxidation which can optionally be followed by a reduction step. Oxidation of carbohydrates on the antibody generate aldehyde groups which can be reduced to their corresponding alcohols. The method involves using a mild oxidizing agent, such as sodium meta periodate, followed by reduction with a mild reducing agent, such as sodium borohydride. In the oxidation procedure, thioether or a thioether containing compounds such as methionine may be optionally added to the reaction mixture to protect oxidation sensitive amino acids in the complement determining region of the antibody. Other water soluble thioethers could also be used for the same purpose. It would be evident to one of ordinary skill in the art that the use of such a compound may be optimized for the particular antibody being oxidized. Also, the molarity of the oxidation and reduction agents as well as other reaction parameters used in the procedure of the present invention may be optimized for each antibody.

Other methods may be used in handling (e.g., stabilizing) the reactive aldehydes generated by oxidizing agents. For example, where the reduction step is omitted after oxidation, aldehydes could be oxidized to corresponding carboxylic acids. This conversion is a facile reaction and can be accomplished using a variety of mild oxidants such as, oxygen, hydrogen peroxide, N-bromosuccinimide, silver oxide, sodium permanganate, and the like. Still another methodology involves capping of aldehydes to render them inactive toward any other functionalities that exist within the antibody. Capping agents include hydroxylamines such as carbomethoxyamine, or hydrazide derivatives such as acetic hydrazide and methyl hydrazino-carboxylate. Reaction of either of these two classes of capping agents results in the formation of stable adducts. Another method involves conversion of the aldehyde to a stable amine by reductive alkylation with a primary amine (e.g., glycine) and sodium cyanoborohydride. All the above-recited agents are commercially available (e.g., Aldrich Chemical Co., Milwaukee, Wis. and Sigma Chemical Co., St. Louis, Mo.) and procedures for their use are known to those in the art.

In one embodiment of the present invention, oxidation of the carbohydrates on NRX 451 using sodium meta periodate ($NaIO_4$) followed by reduction with sodium borohydride ($NaBH_4$) successfully inactivated complement mediated cytotoxicity (C'MC) activity on the antibody without affecting antibody dependent cellular cytotoxicity (ADCC) activity. For example, N-Acetyl-D-Glucoseamine (GlcNac) is oxidized between carbons 3 and 4 to corresponding aldehyde groups. In this embodiment, methionine was added to the reaction mixture to protect oxidation sensitive amino acids in the complement determining region of the antibody. It has been previously reported in the literature (Awwad et al., *Cancer Immunol. Immunother.* 38:23–30 (1994)) that oxidation with NaIO$_4$ does not alter C'MC activity of a monoclonal antibody. However, surprisingly and advantageously it was discovered as disclosed herein that the oxidation/reduction procedure of the present invention altered the C'MC activity without affecting ADCC activity. The degree of carbohydrate modification was monitored by lectin binding ELISA. C'MC and ADCC activity was measured using in vitro $^{51}$Cr release cytotoxicity assays well known in the art.

The antibody NRX451 produced in CHO cells demonstrated some toxicity when given to human subjects in a Phase I clinical trial. It was determined that this particular antibody had ADCC and C'MC activity from in vitro analyses. Also, this monoclonal antibody was cross-reactive with antigens located in the gut of humans which may have been the cause of the toxicity, as well as being reactive at tumor sites. Therefore, the present invention describes chemical modification of the carbohydrates which removes C'MC activity and the toxicity shown in patients. The results of clinical trails from using the chemically modified NRX451 resulted in no toxic effects in the patients. Data from seven patients studied with the oxidized/reduced humanized antibody NRX451 indicate that the antibody can be safely administered.

Using the above-described methodology or other humanization methods referenced herein, humanized sequences may be derived from other antibodies produced against the cancer antigen bound by NR-LU-13. Such antibodies are exemplified in U.S. Pat. No. 5,084,396, referenced herein. These antibodies include NR-LU-01, NR-LU-02, NR-LU-03 and NR-LU-06, and fragments thereof.

After the humanized variable sequences are identified, the corresponding DNA sequences are synthesized and used for the production of humanized antibodies. As discussed supra, these humanized antibodies will preferably exhibit an antigen-binding affinity for the antigen bound by NR-LU-13. Generally the binding affinity will be at least about 10$^4$ M$^{-1}$; preferably at least about 10$^6$ M$^{-1}$; and more preferably at least about 10$^8$ M$^{-1}$. Assays for determining affinity of antibodies for antigen are well known in the art and include by way of example half-optimal binding assays, competition assays, and Scatchard analysis.

The humanized antibodies are obtained by expression of the humanized variable heavy and light chains in an appropriate host system. Essentially, as used herein an appropriate "host system" refers to any expression system including host cell tissue or multicellular organism and vector or vectors containing nucleic acid sequences which encode the subject humanized antibodies or fragments thereof, which in combination provide for the expression of functional antibodies, i.e., the humanized heavy and light chains associate to produce the characteristic antigen-binding structure.

The following references are representative of methods and host systems suitable for expression of recombinant immunoglobulins: Weidle et al., *Gene* 51:21–29 (1987); Dorai et al., *J. Immunol.* 13(12):4232–4241 (1987); De Waele et al., *Eur. J. Biochem.* 176:287–295 (1988); Colcher et al., *Cancer Res.* 49:1738–1745 (1989); Wood et al., *J. Immunol.* 145(a):3011–3016 (1990); Bulens et al., *Eur. J. Biochem.* 195:235–242 (1991); Beggington et al., *Biol. Technology* 10:169 (1992); King et al., *Biochem. J.* 281:317–323 (1992); Page et al., *Biol. Technology* 9:64 (1991); King et al., *Biochem. J.* 290:723–729 (1993); Chaudary et al., *Nature* 339:394–397 (1989); Jones et al., *Nature* 321:522–525 (1986); Morrison and Oi, *Adv. Immunol.* 44:65–92 (1988); Benhar et al., *Proc. Natl. Acad. Sci. USA* 91:12051–12055 (1994); Singer et al., *J. Immunol.* 150:2844–2857 (1993); Cooto et al., *Hybridoma* 13(3):215–219 (1994); Queen et al., *Proc. Natl. Acad. Sci. USA* 86:10029–10033 (1989); Caron et al., *Cancer Res.* 32:6761–6767 (1992); Cotoma et al., *J. Immunol. Meth.* 152:89–109 (1992).

Expression host systems including vectors, host cells, tissues and organisms capable of producing functional recombinant antibodies, and in particular humanized and chimeric antibodies, are well known in the art. Moreover, host systems suitable for expression of recombinant antibodies are commercially available.

Host cells known to be capable of expressing immunoglobulins or antibody fragments include, by way of example, mammalian cells such as Chinese Hamster Ovary (CHO) cells, COS cells, myeloma cells; bacteria such as *Escherichia coli*; yeast cells such as *Saccharomyces cerevisiae*; insect cells such as *Spodoptera frugiperda*; among other host cells. CHO cells are used by many researchers given their ability to effectively express and secrete immunoglobulins. Also, insect cells are desirable because they are capable of high expression of recombinant proteins.

Expression in insect cells or insects is preferably effected using a recombinant baculovirus vector capable of expressing heterologous proteins (herein humanized immunoglobulin sequences) under the transcriptional control of a baculovirus polyhedrin promoter. (E.g., U.S. Pat. No. 4,745,051 relating to baculovirus/insect cell expression system). Polyhedrin is a highly expressed protein, therefore its promoter provides for efficient heterologous protein production. The preferred baculovirus is *Autographa californica* (ACMNPV). Suitable baculovirus vectors are commercially available from Invitrogen.

Essentially, these vectors are modified, e.g., by homologous recombination to produce recombinant baculovirus containing humanized NR-LU-13 variable heavy and light sequences operably linked to the polyhedrin promoter. Insects or insect cells are then infected with the recombinant baculovirus. Preferably, the baculovirus will invade the cells of the wall of the insect gut, migrate to the nucleus of these cells and replicate, resulting in occlusion bodies which accumulate in infected cells and tissues, which ultimately lyse the insect. The expressed humanized antibodies are then recovered from the insect or insect remains.

Also, the subject humanized antibodies may be expressed in transgenic plants or animals. The subject humanized antibody sequences may be operatively linked to a promoter that is specifically activated in mammary tissue such as a milk-specific promoter. Such methods are described in U.S. Pat. No. 4,873,316 and U.S. Pat. No. 5,304,498.

Typically, such methods will use a vector containing a signal peptide which enables secretion of an operably linked polypeptide sequence, a milk specific promoter such as casein promoter, an enhancer sequence and humanized immunoglobulin sequences specific to the NR-LU-10 antigen, e.g., humanized sequences derived from NR-LU-13.

This vector will be introduced in a suitable host, e.g., bovine, ovine, porcine, rabbit, rat, frog, or mouse embryo, typically by microinjection under conditions whereby the expression vector integrates into the genome of the particular embryo. The resultant transgenic embryo is then transferred to a surrogate mother, and offspring are screened to identify those transgenics which contain and express the humanized antibodies in their milk. Transgenics which contain and/or express the antibody sequences may be identified, e.g., by Southern blot or Western blot analysis. The milk produced by such transgenic animals is then collected and humanized antibodies isolated therefrom. As noted, such methods are described in detail in U.S. Pat. Nos. 4,873,316 and 5,304,498.

The subject humanized antibody sequences may also be expressed in plants, e.g., transgenic plants, plant tissues, plant seeds and plant cells. Such methods are described, e.g., in U.S. Pat. No. 5,202,422.

Expression vectors suitable for transformation of plants, plant tissues and plant cells are known in the art. In general, such vectors include the DNA of interest (herein humanized antibody sequences), a suitable promoter (typically plant, bacterial or viral promoter) and a selectable marker functional in plants or plant cells. Methods for introducing desired DNAs into plants and plant cells include by way of example Agrobacterium-mediated transformation, protoplast transformation, gene transfer into pollen, injection into reproductive organs and injection into immature embryos.

The transformed embryos or plants are then used to produce progeny by traditional methods, e.g., cross-fertilization, backcrossing, etc. Progeny which express the humanized antibody are then identified, e.g., by Western blotting, cell binding assays, etc. These progeny are then cultivated and harvested and used for recovery of antibodies. Such methods are described in detail in U.S. Pat. No. 5,202,422 and U.S. Pat. No. 5,004,863. Plants useful for the expression of heterologous proteins are well known and include, by way of example, tomatoes, tobacco, corn, soybean and cotton plants. For example, the subject humanized antibodies which optionally are further Imutated to eliminate glycosylation sites may be expressed in plant cells that do not N-link glycosylate and/or O-link glycosylate antibodies and antibody fragments.

Recombinant expression of functional humanized antibodies may be effected by one of two general methods. In the first method, the host or host cells are transfected with a single vector which provides for the expression of both heavy and light variable sequences fused to appropriate constant regions. In the second method, host cells are transfected with two vectors, which respectively provide for expression of either the variable heavy or light sequence fused to an appropriate constant region.

The subject humanized sequences derived from NR-LU-13 are expressed in appropriate host cells under conditions that a functional antibody fragment (e.g., Fv) or entire antibody is obtained. Preferably such sequences will be fused to appropriate human constant sequences, i.e., human heavy or light constant sequences. Human constant sequences are well known and have been reported in the literature. For example, Kabat et al., "Sequences of Proteins of Immunological Interest," 5th Ed., U.S. Dept. Health & Human Services (1991), contains such sequences. Known human constant sequences used for the production of humanized antibodies include, by way of example, human gamma 1, gamma 3 and gamma 4 (human heavy constant sequences) and kappa and lambda (human light constant sequences). The selected human constant sequence affects the effector function of the humanized antibody.

In expressing recombinant antibodies in cell culture, e.g., in CHO cells or insect cells, it is preferred to provide for the secretion of the antibody by the host cell. This entails operably linking the DNA's encoding the humanized heavy and light chain sequences to appropriate signal peptide sequences, i.e., those which are recognized and processed by the particular host cell. Signal peptides are well known and available. Typically, a signal peptide is selected which is homologous to the host cell or the expressed protein. For example, the endogenous signal peptides of murine NR-LU-10 may be used.

The expression system (e.g., expression vector) will preferably contain sequences which provide for the selection of transfectants and expression of humanized antibodies. Therefore, preferably the vector or vectors will contain genes which allow for selection, e.g., antibiotic (or drug) resistance genes. Also, the vector will preferably contain promoters which provide for efficient expression of the heavy and light chains as well as other regulatory sequences, e.g., polyadenylation regions, enhancer regions, etc. The design of systems suitable for expression of recombinant antibodies is well known and within the purview of the ordinary skilled artisan, as evidenced by the above-identified references relating to expression of recombinant immunoglobulins.

A well known example of host cells suitable for expression of immunoglobulins is CHO cells. In expressing immunoglobulins in CHO cells, or other mammalian cells, it is desirable to include a sequence which provides for amplification, so as to enhance vector copy number and enhance antibody yields. Such sequences, includes, by way of example dominant selectable markers, such as dihydrofolate reductase (DHFR), neomycin phosphotransferase (NEO), glutamine synthetase (GS), adenosine deaminase (ADA), among others.

Examples of suitable promoters useful for the expression of proteins in mammalian cells include, by way of example, viral promoters such as the human cytomegalovous (CMV) early promoter, SV40 early and late promoters, and the RSV promoter and enhancer. Also, mammalian promoters may be used, e.g., immunoglobulin promoters, growth hormone promoters such as bovine growth hormone promoter, etc. It is preferable to select a strong promoter, i.e., one which provides for high levels of transcription.

Also, the vector will preferably contain polyadenylation sequences (polyA) sequences which provide for polyadenylation of MRNA which function to enhance MRNA stability, and thereby enhance protein production. Examples of suitable poly A sequences include, by way of example, SV40 poly A sequences, and bovine growth hormone promoter (BGH) poly A sequence, among others.

In one embodiment of the present invention, it was elected to express the subject humanized sequences in CHO (dhfr) cells, which cells were transfected with a vector which was derived from a commercially available vector but which was modified.

Plasmid vector pcDNA3 was obtained from Invitrogen Corp. (San Diego, Calif.). This vector contains the human cytomegalovirus (hCMV) promoter and enhancer (Boshart et al., *Cell* 41:521–530 (1985)) for target gene expression, a neomycin resistance gene for selection in mammalian cells and a prokaryotic origin of replication and beta-lactamase gene for propagation and selection in *E. coli*. Vector pcDNA3 was modified to incorporate a second hCMV promoter and enhancer, also a DHFR gene for gene amplification and additional restriction sites to accommodate the antibody genes.

In one embodiment, it was elected to fuse the heavy and light NRX451 humanized variable sequences to human γ1 and K constant regions. However, other human constant regions may be substituted therefor. The exact methods which were used are described in detail in the examples. Moreover, it is expected that humanized antibodies containing the subject NRX451 humanized heavy and light sequences may be expressed using other constant regions or other known host systems which are capable of expressing functional recombinant antibodies. In particular, it is expected that the subject humanized antibodies may be expressed in transgenic plants or animals, or in insects as described above.

After the humanized antibodies are expressed they are purified and then assayed for their ability to bind antigen. Methods for purifying recombinant immunoglobulins are well known and are described in the references incorporated herein relating to production of recombinant antibodies. For example, a well known method of purifying antibodies involves protein A purification because of the propensity of protein A to bind the Fc region of antibodies.

The ability of the subject humanized antibodies to bind antigen is determined by any of numerous known methods for assaying antigen-antibody affinity. As discussed, the parent murine antibody NR-LU-13 binds an approximately 40 kilodalton glycoprotein expressed on numerous carcinomas. This antigen has been characterized in Varki et al., *Cancer Res.* 44:681–687 (1984); Okabe et al., *Cancer Res.* 44:5273–5278 (1989), referenced herein. Thus, it is routine to test the ability of humanized antibodies produced according to the invention in binding the NR-LU-13 antigen. Moreover, methods for evaluating the ability of antibodies to bind to epitopes of this antigen are known.

In one aspect of the invention, the humanized antibodies (or fragments thereof) of the present invention would be usefail tools in methods for medical diagnostic and therapeutic purposes. A diagnostic method or therapeutic method is described for detecting the presence or absence of a target site within a mammalian host. When determining the criteria for employing humanized antibodies or antibody conjugates for in vivo administration for therapeutic purposes, it is desirable that the general attainable targeting ratio is high and that the absolute dose of therapeutic agent delivered to the tumor is sufficient to elicit a significant tumor response. Methods for utilizing the humanized antibodies described in the present invention can be found, for example, in U.S. Pat. Nos. 4,877,868, 5,175,343, 5,213,787, 5,120,526, and 5,202,169.

In a preferred embodiment of the invention, an antibody conjugate or composition of the present invention is used in pretargeting methods. Essentially, such pretargeting methods are characterized by an improved targeting ratio or increased absolute dose to the target cell sites in comparison to conventional cancer diagnosis or therapy. A general description of pretargeting methods may be found in U.S. Pat. Nos. 4,863,713, 5,578,287, and 5,630,996. Moreover, typical pretargeting approaches are summarized below.

Pretargeting methods are of two general types: three-step pretargeting methods and two-step pretargeting methods.

The three-step pretargeting protocol features administration of an targeting moiety-ligand conjugate, which is allowed to localize at a target site and to dilute in the circulation. This is followed by administration of an anti-ligand which binds to the targeting moiety-ligand conjugate and clears unbound targeting moiety-ligand conjugate from the blood, as well as binds to targeting moiety-ligand conjugate at the target site. Thus, the anti-ligand fulfills a dual function by clearing targeting moiety-ligand conjugate not bound to the target site as well as attaches to the target site form a targeting moiety-ligand: anti-ligand complex. Finally, a diagnostic or therapeutic active agent-ligand conjugate that exhibits rapid whole body clearance is administered.

When the active agent-ligand conjugate in circulation comes into close proximity to the targeting moiety-ligand: anti-ligand complex bound to the target site, the anti-ligand portion of the complex binds to the ligand portion of the circulating active agent-ligand conjugate, thus producing a targeting moiety-ligand: anti-ligand:ligand-active agent "sandwich" at the target site. Furthermore, because the unbound diagnostic or therapeutic active agent is attached to a rapidly clearing ligand (rather than a slowly clearing targeting moiety, such as antibody, antibody fragment), this technique provides decreased non-target exposure to the active agent.

Alternatively, the two-step pretargeting methods eliminate the step of administering the above identified anti-ligand. These "two-step" procedures feature targeting moiety-ligand or targeting moiety-anti-ligand administration, followed by the administration of active agent conjugated to the opposite member of the ligand/anti-ligand pair.

As an optional step in the two-step pretargeting methods of the present invention, ligand or anti-ligand, designed specifically to provide a clearance function, is administered to facilitate the clearance of circulating targeting moiety-ligand or targeting moiety-anti-ligand. Thus, in the two-step pretargeting approach, the clearing agent does not become bound to the target cell population, either directly or through the previously administered target cell bound targeting moiety-anti-ligand or targeting moiety-ligand conjugate.

A targeting moiety in the pretargeting methods of the present invention has the functional property that it binds to a defined target cell population, such as tumor cells. Preferred targeting moieties useful in this regard are antibodies (polyclonal or monoclonal), such as human monoclonal antibodies or "humanized" murine or chimeric antibodies are also useful as targeting moieties in accordance with the present invention. Some examples of humanized antibodies include those that are CHO produced, produced in hosts such as plant (for example corn, soybean, tobacco, and the like), insect, mammalian, yeast, and bacterial. The humanized antibodies may be those that bind to the antigen bound by antibody NR-LU-13. Preferably, the humanized antibody may not possess N-linked glycosylation or its N-linked glycosylation has been modified post expression to reduce immunogenicity or toxicity.

The subject humanized antibodies may potentially possess antitumor activity even absent attachment to other diagnostic or therapeutic active agents, because of the presence of human constant sequences which may provide for human effector functions. However, while antibody (therapeutic or diagnostic agent) conjugates have known application in therapy and diagnostics alone, in the preferred embodiments of the present invention, humanized antibodies will be used in the pretargeting methods as prototypical targeting moieties.

Ligand/Anti-ligand pairs suitable for use in the present invention include biotin/avidin or streptavidin, haptens and epitopes/antibody, fragments or analogs thereof, including mimetics, lectins/carbohydrates, zinc finger proteins/dsDNA fragments, enzyme inhibitors/enzymes; and analogs and derivatives thereof. Preferred ligands and anti-ligands bind to each other with an annnity of at least about $K_A \geq 10^9 M^{-1}$ or $K_D \leq 10^{-9} M$. Biotin/avidin or streptavidin is a preferred ligand/anti-ligand pair.

In general such pretargeting methods will preferably include the administration of a anti-ligand that provides a clearance function. The clearance is probably attributable to cross-linking and/or aggregation of conjugates that are circulating in the blood, which leads to complex/aggregate clearance by the recipient's RES (reticuloendothelial system). In one embodiment of the present invention, the anti-ligand clearance of this type is preferably accomplished with a multivalent molecule. However, a univalent molecule of sufficient size to be cleared by the RES on its own could also be employed.

Alternatively, receptor-based clearance mechanisms, e.g., Ashwell receptor or other receptors, may be exploited by addition of hexose residues, such as galactose or mannose residues, to provide for clearance of the anti-ligand, anti-ligand conjugate or humanized antibody via the liver. Such clearance mechanisms are less dependent upon the valency of the clearing agent than the RES complex/aggregate clearance mechanisms described above.

For example, if the targeting moiety-ligand or targeting moiety-anti-ligand has been derivatized to provide for clearance (i.e., addition of a hexose residue) a clearing agent should not be necessary. Preferred clearing agents are disclosed in U.S. Pat. Nos. 5,624,896 and 5,616,690; as well as PCT Application Publication Number WO 95/15978.

Diagnostic and therapeutic active agents of the present invention include anti-tumor agents such as, radionuclides, cytokines, drugs and toxins.

Radionuclides usefull within the present invention include gamma-emitters, positron-emitters, Auger electron-emitters, X-ray emitters and fluorescence-emitters, with beta- or alpha-emitters preferred for therapeutic use. Radionuclides are well-known in the art and include $^{123}$I, $^{125}$I, $^{130}$I, $^{131}$I, $^{133}$I, $^{135}$I, $^{47}$SC, $^{72}$AS, $^{72}$Se, $^{90}$Y, $^{88}$Y, $^{97}$Ru, $^{100}$Pd, $^{101m}$Rh, $^{119}$Sb, $^{128}$Ba, $^{197}$Hg, $^{211}$At, $^{212}$Bi, $^{153}$Sm, $^{169}$Eu, $^{212}$Pb, $^{109}$Pd, $^{111}$In, $^{67}$Ga, $^{68}$Ga, $^{64}$Cu, $^{67}$Cu, $^{75}$Br, $^{76}$Br, $^{77}$Br, $^{99m}$Tc, $^{11}$C, $^{13}$N, $^{15}$O, $^{166}$Ho, and $^{18}$F. Preferred therapeutic radionuclides include $^{188}$Re, $^{186}$Re, $^{203}$Pb, $^{212}$Pb $^{212}$Bi, $^{109}$Pd, $^{64}$Cu, $^{67}$Cu, $^{90}$Y, $^{125}$I, $^{131}$I, $^{77}$Br, $^{211}$At, $^{97}$Ru, $^{105}$Ru, $^{198}$Au, $^{166}$Ho, and $^{199}$Ag or $^{177}$Lu.

Other anti-tumor agents, e.g., agents active against proliferating cells, are useful in the present invention. Exemplary anti-tumor agents include cytokines, such as IL-2, IL-12, interferon α, β or γ, tumor necrosis factor or the like, lectin inflammatory response promoters (selectins), such as L-selectin, E-selectin, P-selectin or the like, and like molecules.

Drugs suitable for use herein include conventional chemo-therapeutics, such as vinblastine, doxorubicin, bleomycin, methotrexate, 5-fluorouracil, 6-thioguanine, cytarabine, cyclophosphamide and cis-platinum, as well as other conventional chemotherapeutics as described in *Cancer: Principles and Practice of Oncology*, 2d ed., V. T. DeVita, Jr., S. Hellman, S. A. Rosenberg, J. B. Lippincott Co., Philadelphia, Pa, 1985, Chapter 14. A preferred drug within the present invention is a trichothecene. Other preferred drugs suitable for use herein as a diagnostic or therapeutic active agent in the practice of the present invention include experimental drugs as described in *NCI Investigational Drugs, Pharmaceutical Data* 1987, NIH Publication No. 88–2141, Revised November 1987.

Several of the potent toxins useful within the present invention consist of an A and a B chain. The A chain is the cytotoxic portion and the B chain is the receptor-binding portion of the intact toxin molecule (holotoxin). Preferred toxins in this regard include holotoxins, such as abrin, ricin, modeccin, Pseudomonas exotoxin A, Diphtheria toxin, pertussis toxin and Shiga toxin; and A chain or "A chain-like" molecules.

In a preferred embodiment, the targeting moiety will comprise a humanized antibody or a humanized antibody conjugate of the present invention, the ligandlanti-ligand binding pair will be biotin/avidin (e.g., streptavidin), and the active agent will be a radionuclide in pretargeting methods. The particularly preferred retargeting method is the two-step method and the use of a clearing agent. The preferred humanized antibody targeting moiety is an antibody which specifically binds to the antigen bound by NR-LU-13 and the humanized antibody does not possess glycosylation or its glycosylation has been chemically modified.

One skilled in the art, based on the teachings in this application and the applications referenced herein, can readily determine an effective diagnostic or therapeutic effective dosage and treatment protocol. This will depend upon factors such as the particular selected therapeutic or diagnostic agent, route of delivery, the type of target site(s), affinity of the targeting moiety for target site of interest, any cross-reactivity of the targeting moiety with normal tissue, condition of the patient, whether the treatment is effected alone or in combination with other treatments, among other factors. A therapeutic effective dosage is one that treats a patient by extending the survival time of the patient. Preferably, the therapy further treats the patient by arresting the tumor growth and most preferably, the therapy further eradicates the tumor.

For example, in the case of humanized antibody—avidin or streptavidin conjugates in pretargeting strategies, a suitable dosage will range from about 10 to about 2500 mg, more preferably from about 50 to 1500 mg, and most preferably from about 100 to 800 mg. The dosage of the ligand-active agent conjugate, for example, a radionuclide—biotin containing conjugate, will generally range from about 0.001 to about 10 mg and more preferably from about 0.1 to 2 mg. For example, a suitable dosage of ligand-active agent, Y-90-DOTA-biotin, ranges from about 10 to 300 mCi in 0.1 to 2.0 mg. Also, In$^{111}$ may be used at 1–10 mCi alone or in combination with Y$^{90}$. The radioactivity ranges are dependent upon the isotope employed.

In general such pretargeting methods will include the administration of a clearing agent. The dosage of the clearing agent will be an amount which is sufficient to substantially clear the previously administered conjugate from the circulation, i.e., at least about 50%, more preferably at least about 90%, and most preferably approaching or at 100%. In general, this will be administered several days after administration of the humanized antibody—streptavidin conjugate, preferably about 1 to 5 days after, more preferably at least about 1 to 2 days after. Generally, the determination of when to administer the clearing agent depends on the target uptake and endogenous clearance of targeting moiety conjugate. Particularly preferred clearing agents are those which provide for Ashwell receptor mediated clearance, such as galactosylated proteins, e.g., galactosylated biotinylated human serum albumin (HSA) and small molecule clearing agents containing galactose and biotin. In the case of HSA based clearing agents, a typical dosage of the clearing agent will range from about 100 to 1000 mg, and more preferably about 200–500 mg.

If a clearing agent is administered, the ligand-active agent conjugate is preferably administered about 2 to 12 hours after.

The conjugates may be administered by known methods of administration. Known methods of administration include, by way of example, intraperitoneal injection, intravenous injection, intramuscular injection, intranasal administration, among others. Intravenous administration is generally preferred.

The present invention is further described through presentation of the following examples. These examples are offered by way of illustration and not by way of limitation.

EXAMPLES

Example 1

HUMANIZED SEQUENCES OF NRX451

Essentially, the cDNA sequence encoding the variable regions of NR-LU-13 antibody (hybridoma producing the antibody was deposited with American Type Culture Collection (1080 University Blvd., Manassas,Va. 20110 as ATCC Accession No. SD3273, converted to ATCC Accession No. CRL-12360) were cloned and sequenced by known methods. The cDNA sequences of the cloned light and heavy sequence of NR-LU-13 are contained in FIG. 2. Using these sequences, the amino acid sequence of the Fv region of NR-LU-13 which includes the entire variable light and variable heavy regions was elucidated.

A. Humanization Protocol

Briefly, the humanization protocol comprises a cycle of sequence analysis and molecular modeling, as outlined in FIG. 1. Sequence Human Ab data was obtained from the immunoglobulin sequence database (E. A. Kabat et al., Sequences of Proteins of Immunological Interest, U.S. Departmnent of Health and Human Services, Fifth Edition, 1991), and structural data was obtained from the Brookhaven databank (F. C. Bernstein et al., *J Molec. Biol.* 112:535–42, (1977)).

The antibody heavy and light chain sequences of NR-LU-13 were compared to a database of human sequence pairs (immunoglobulin light and heavy chains originating from the same clone). Based on this comparison, the most identical human sequence was chosen to supply the framework for the grafted antibody. The sequences of the murine complementarity determining regions (CDRs) of NR-LU-13 were then transferred to the selected human framework. This process provided the "initial" humanized Fv sequence.

This initial humanized sequence was then reformed by testing sequences in three-dimensional models. A model was constructed of the original murine sequence and of the initial putative humanized sequence. Equivalent residue positions in the murine model and the humanized model were compared. Residues in the humanized model which were predicted to perturb the structure of the CDRs were "back mutated", i.e., murine framework residues were restored. Models were then constructed using modified sequences, and were again compared to the murine Fv model. This cycle of modeling a "back mutation" and comparing it to the murine model was continued, until the conformation of the CDRs in the humanized model closely matched the CDR conformations in the parent murine model. The specific stepwise process which resulted in the subject humanized heavy and light sequences derived from NR-LU-13 is contained in FIG. 1.

B. Sequence Analysis

The variable sequences of the NR-LU-13 antibody were compared to 58 pairs of κ-heavy chain pairs which are known CDR to be expressed together as functional antibodies. The most identical sequence pair was found to be that from the human antibody clone R3.5H5G'CL (A. Manheimer-Lory et al., *J. Exp. Med.* 174:1639–52, (1991)). The NR-LU-13 antibody contains a κV/hIIc chain pair. The R3.5H5G'CL antibody is a κI/hI chain pair. Therefore, both light and heavy chains were selected from the most homologous human classes.

The NR-LU-13 light and heavy chain sequences were compared with a database of immunoglobulin sequences, in order to identify abnormal sequence positions. The relative frequency for each residue position showed that the heavy chain framework region 3 (HFR3) was the most abnormal region within the NR-LU-13 antibody sequence, and in particular, position Cys 181 was abnormal. In most of the sequences examined (90%), this position was occupied by a Tyr residue, forming an integral part of the $V_L/V_H$-interface. Residue frequencies within selected positions are depicted in FIGS. 7a–7f.

C. Modeling Construction i. Modeling Protocol

Models were constructed using the combined algorithm previously described by Martin et al., *Proc. Natl. Acad Sci., USA* 86:9268–72 (1989) and Pedersen et al., *Immunomethods* 1:126–36 (1992).

Whenever possible, CDRs were modeled from canonical loops (Chothia et al., *Nature* 342:877–83 (1989)). Remaining loops were modeled using a combination of database search and ab initio methods, using the conformational search program CONGEN of R. E. Bruccoleri and M. Karplus, *Biopolymers* 26:137–68 (1987). In the case of NRX451 CDRs, L1, L2, L3, H1 and H2 were built from canonical loops. CDR H3 was constructed using a database search at the base of the CDR and ab initio fragment generation for the central part of the loop to attempt to saturate conformational space. CDR H3 was built onto a combining site containing only the backbone atoms of the canonical loops, and all atoms from framework residues. All CDR sidechains were reconstructed using CONGEN.

The models were energy minimized. In the minimization, the backbone of the framework was fixed, although the framework sidechains and the CDRs were allowed to move.

ii. Outline of "Back Mutations"

Initial "back mutations" (replacement of murine framework residues) from CDR-grafted NRX451 (the "initial" nominal sequence) were identified where the canonical classification of the CDRs was changed by the change in framework sequence. Only one such position was identified—Arg 193 (R3.5H5G'CL)/Ala 193 (NRX451). This position is a canonical determinant for CDR H2 (incorporated in graft 2 and thereafter). Any residue position within 5 A of a CDR residue which had altered residue type in the R3.5H5G'CL framework sequence was "back mutated" if sidechain or backbone conformation was significantly altered between the NPTX451 and R3.5H5G'CL model. Residue positions Ser 55, Thr 141. Tyr 181, Ala 182, Met 191, Ser 198 and Ala 218 were "back mutated" in this way (incorporated in graft 4 and thereafter).

Finally, all residue differences between the R3.5H5G'CL framework and the NRX451 framework were visually inspected. Two additional residue positions close to the CDRs were identified (Thr 75 and Phe 77) and "back mutated".

iii. Humanized Model

Figure 6A:
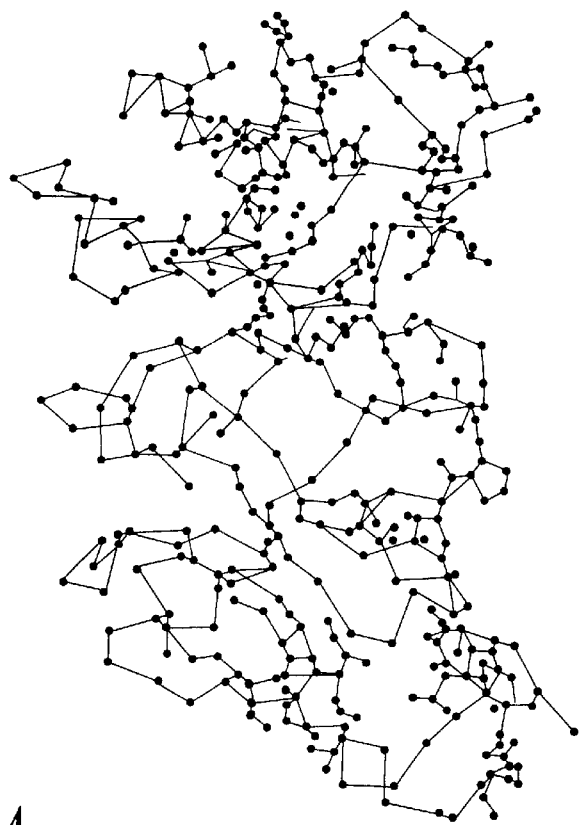
FIGS. 6a and 6b contain molecular models of (a) the Fv of chimeric NR-LU-13 antibody and (b) a humanized Fv (NRX451) derived therefrom.
Figure 6B:
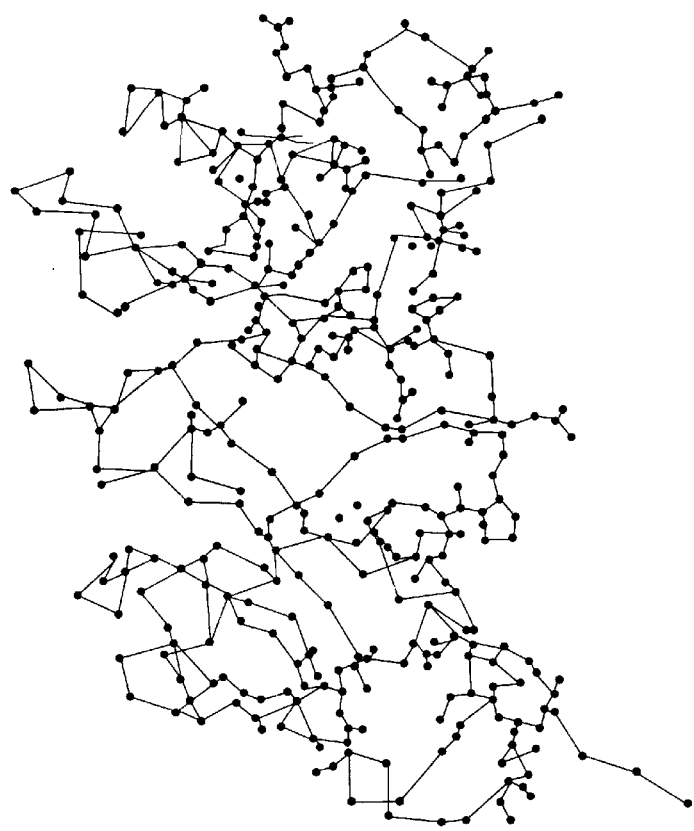

In the final NRX451/R3.5H5G'CL models, the residues of the light and heavy chain variable regions that differ between NR-LU-13 and NRX451-humanized sequences are mainly at the base of the Fv domain towards the C portion of the Fab fragment (see FIG. 5). Models were analyzed using ProCheck (v.2.1) (R. A. Laskowski et al., Instruction Manual, "Procheck v.2.1: Programs to check the stereochemical quality of protein studies", Oxford Molecular Ltd. (1993)). FIG. 6 contains molecular models of the NR-LU-13 and the first humanized Fv derived therefrom NRX451.

4. Humanized Sequence

The humanized light and heavy sequences are respectively derived from NR-LU-13, referred to as NRX451 heavy and light chains, are presented in FIGS. 3 and 4. The variable sequences of NR-LU-13 and humanized NRX451 are aligned in FIG. 5. The chains are numbered separately.

Thus, based on these sequences, DNAs encoding such humanized variable regions are synthesized.

Example 2

GENERAL METHODOLOGY FOR CONSTRUCTION OF HUMANIZED VARIABLE REGIONS

Variable Region Synthesis

The humanized variable regions were synthesized as a series of overlapping oligonucleotides. Each complete variable region was 400 to 450 bases in length.

Approximately 16 oligonucleotides (oligos) were synthesized to cover both heavy and light chains. Oligos ranged in size from 40 to 88 bases. The annealed gene fragments were amplified by PCR and cloned. Each variable region included restriction sites to facilitate cloning, a leader sequence to direct secretion from eukaryotic cells, and a splice donor site to allow precise joining with the constant region.

Euklarotic Expression Vector

A vector was constructed which was able to stably transfect eukaryotic cells and direct high level expression of the antibody chains. A commercially available vector containing the CMV promoter and enhancer and the neomycin resistance gene, was modified to contain a second CMV promoter and enhancer, immunoglobulin constant regions and a DHFR gene.

Figure 8:
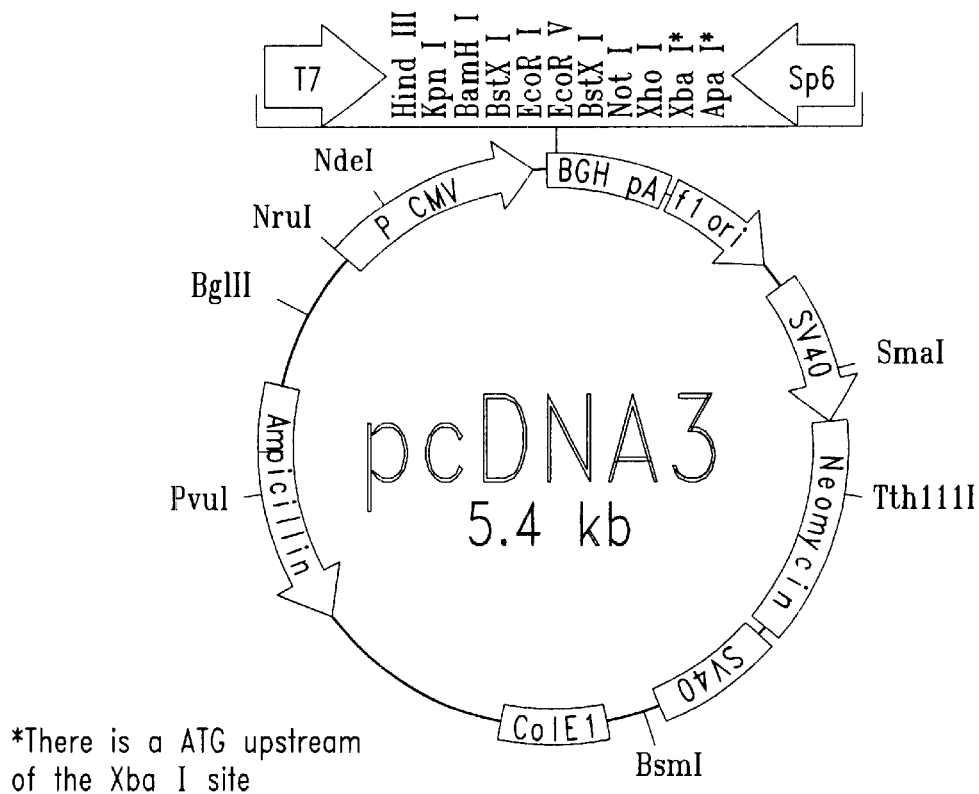
FIG. 8 depicts a plasmid pcDNA3 which is an intermediate for pNRX451-C, a plasmid used to express NRX451.

The vector pCDNA3 was purchased from Invitrogen Corp. (San Diego, Calif.). This vector is depicted in FIG. 8. The neomycin resistance gene of pCDNA3 allows selection of G418 resistant transfectants in eukaryotic cells. This vector contains prokaryotic elements which enable selection and propagation in *E. coli*.

A second CMV promoter and enhancer region were added using PCR to copy the existing CMV elements followed by insertion into pCDNA3. Specifically, oligonucleotides NX62 (CCTGACGAATTCGTTGACATTGATTATTGAC) (SEQ ID NO:1) and NX63 (CCTGACGCGGCCGCTTCGATAAGCCAGTAAGC) (SEQ ID NO:2) were synthesized to anneal to the 5' and 3' ends of CMV, respectively. NX62 and NX63 were synthesized to introduce EcoRI and NotI restriction sites, respectively. PCR was performed by standard procedures and the resulting fragment was restriction digested with EcoRI and NotI. Plasmid pCDNA3 was likewise digested and the fragment was inserted by standard procedures well known in the art. The resulting plasmid was designated pCMV4.

The kappa constant region and preceding intron were isolated from human peripheral blood lymphocyte DNA by PCR. Oligonucleotides NX64 (GTTCGGCTCGAGCACAGCTAGCATTATCTGGGA TAAGCATGCTG) (SEQ ID NO:3) and NX65 (GTTACGGGGCCCCTAACACTCTCCCCTGTTGAAG) (SEQ ID NO:4) were synthesized to anneal to the intron preceding the constant region exon and the 3' end of the constant region, respectively. NX64 contained both XhoI and NheI restriction sites. NX65 contained an ApaI restriction site following the constant region stop codon. PCR was performed by standard procedure. The fragment was digested with XhoI and ApaI and inserted into pCMV4 by standard procedures. The resulting plasmid was designated pC4-CK3.

The human gammal constant region, including the preceding intron and succeeding polyadenylation site, was isolated from human plasmacytoma (MC/CAR, ATCC CRL 8083) DNA by PCR. Oligonucleotides NX66 (GTACGCGGATCCCAGACACTGGACGCTG) (SEQ ID NO:5) and NX67 (CATTCGGAATTCGAACCATCACAGTCTCGC) (SEQ ID NO:6) were synthesized to anneal to the preceding intron and polyadenylation site, respectively. NX66 contained a BamHI site. NX67 contained an EcoRI site following the polyadenylation site. PCR was performed by standard procedure. The fragment was inserted into pCDNA3 by standard procedures. The resulting plasmid was designated pGammal-4.

The humanized variable regions of the heavy and light chains were synthesized in similar manner. A series of eight overlapping oligonucleotides were synthesized for each variable region plus native murine leader sequence. The internal 6 oligonucleotides ranged from 79 to 88 bases in length with overlaps of 19 to 26 base pairs. The outside oligonucleotides were 40 to 44 bases in length including restriction sites (Vh; HindIII and BamHI, Vk; NotI and NheI). The 3' outside oligonucleotides also included intron splice donor sites. The PCRs contained 1 pmol each of the internal oligonucleotides and 30 pmol each of the outside primers. The temperature profile of the reaction was as follows: 1 cycle of 5 min at 94° C., and 1 cycle of 5 min at 72° C. The resulting PCR products were restriction digested with the appropriate enzymes and inserted into pC4-CK3 (Vk) or pGamnmal-4 (Vh) to give rise to plasmids pVKE and p4gammaB respectively. Both plasmids were restriction endonuclease cleaved with BglII and EcoRI. A 6 kilobase (kb) fragment from pVKE and a 3.2 kb fragment from p4gammaB were joined to form pWE1A2. Plasmid pWE1A2 contained the complete humanized heavy and light chains in essentially genomic (intron-containing) form. Antibody expression from COS and CHO cells transfected with pWE1A2 was very poor.

The plasmid was modified to contain the antibody genes in cDNA form. An additional BGH polyadenylation region was added to follow the heavy chain cDNA. The DHFR gene and control elements were added.

The BGH polyadenylation region was copied from pCDNA3 using PCR and inserted into pWE1A2 as a BamHI/EcoRI fragment. The resulting plasmid lacked the gamma constant region, but could now accommodate the cDNA gamma chain as an XbaI/BamHI fragment.

RNA was extracted from pWE1A2 transfected CHO (dhfr) cells with a commercially available RNA extraction kit (Glass Max, Gibco BRL). Reverse transcriptase-PCR (RT-PCR) was performed as per manufacturer's instructions (Perkin Elmer Cetus). In this procedure, NX109 (GCTGACGAATTCTCATTTACCCGGAGACAGGGAG) (SEQ ID NO:7), which anneals to the 3' terminus of the gamma chain constant region was used to specifically prime a reverse transcriptase reaction in which gamma chain messenger RNA was copied into cDNA. NX109 and NX110 (CCGTCTATTACTGTTCTAGAGAGGTC) (SEQ ID NO:8), which anneals within the heavy chain variable region, were used to amplify the cDNA generated in the reverse transcription reaction. The PCR primers contained BamHI (NX109) and XbaI (NX110) restriction sites to facilitate cloning. The restricted PCR product was inserted into the plasmid to form plA2.C1.

A DHFR gene transcription unit was added to the plasmid to allow gene amplification in eukaryotic cells. The DHFR coding sequence was preceded by an SV40 promoter and followed by an SV40 polyadenylation signal. The DNA encoding DHFR and control elements was generated by PCR and inserted into plA2.C1 to form plasmid p61.1.

Figure 9:
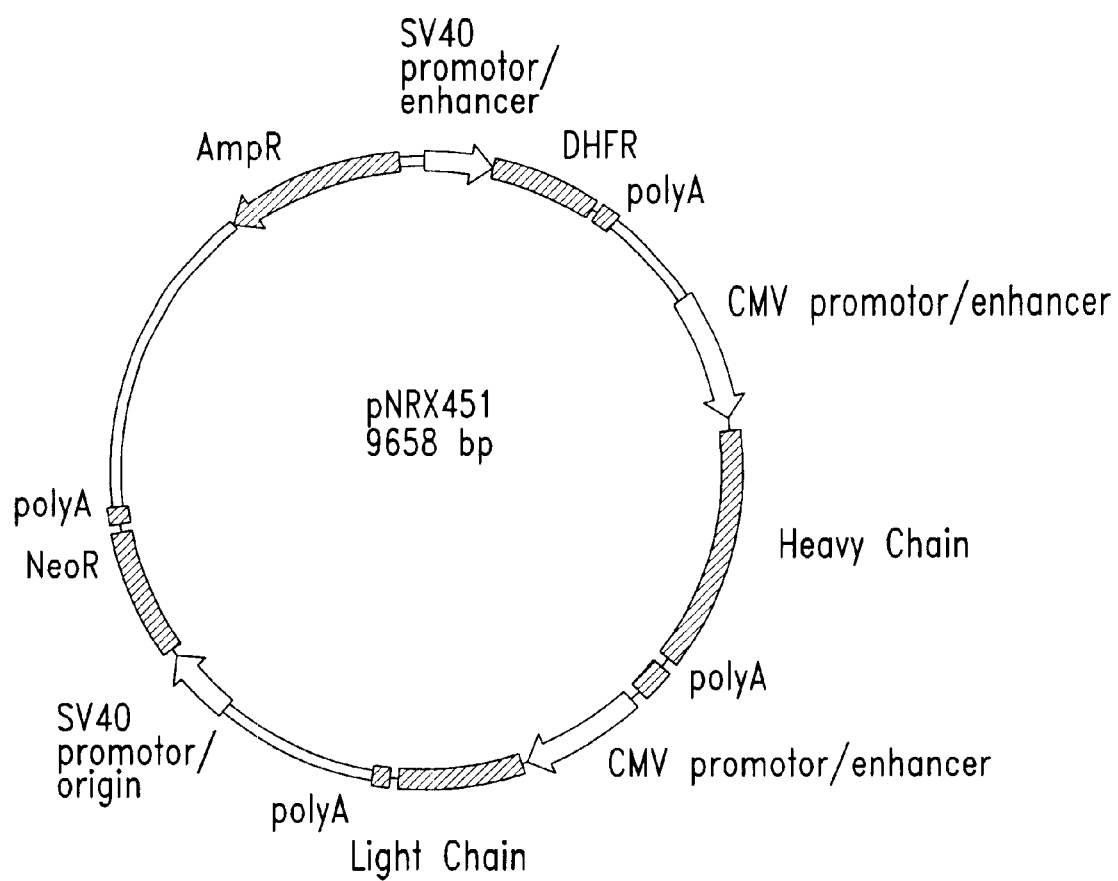
FIG. 9 depicts plasmid pNRX451-C used to express NRX451.
Figure 10:
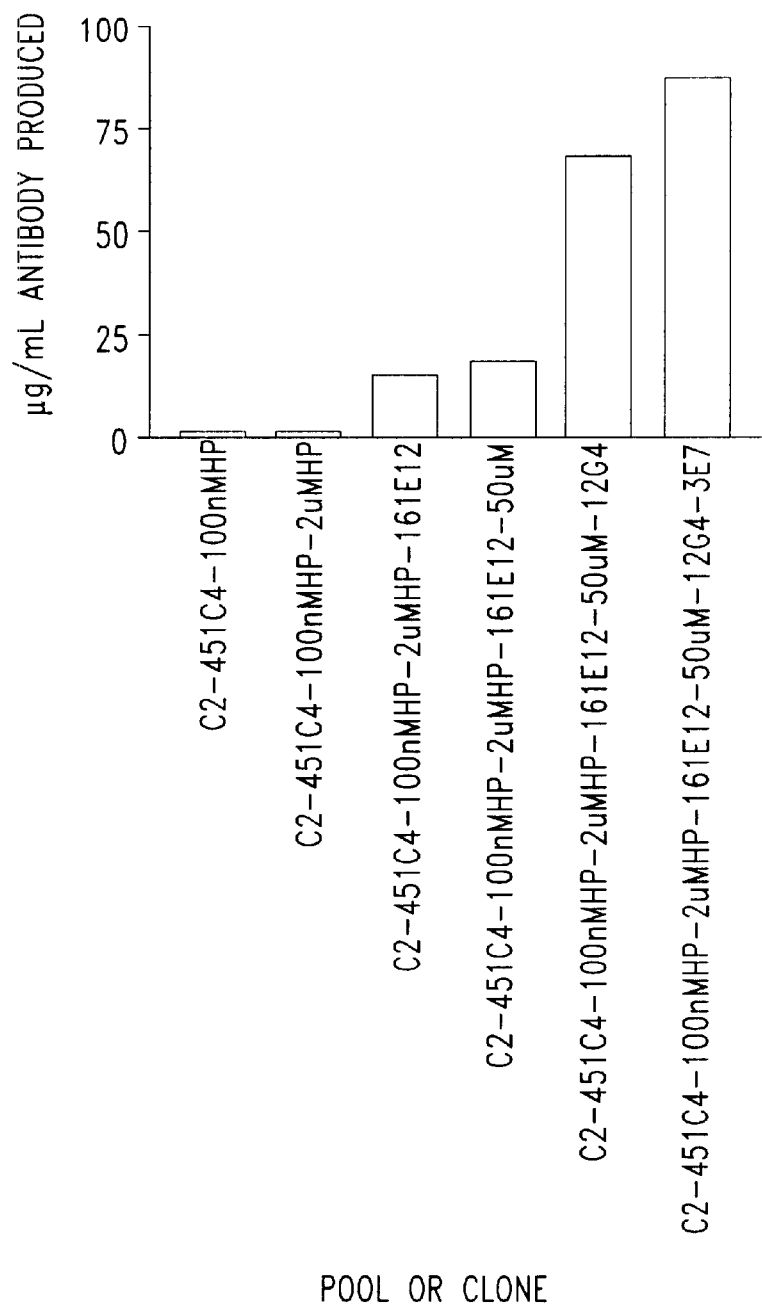
FIG. 10 contains results of kappa and gamma ELISAs for specific NRX451 humanized antibody producing clones.

The light chain genes were switched to cDNA by the identical process used for the heavy chain. Oligonucleotide NX65 (GTTACGGGGCCCCTAACACTCTCCCCTGTTGAAG) (SEQ ID NO:4), which anneals to the 3' end of the kappa constant region, was used for reverse transcription and then NX65 and NXK1 (CAGCGTGCGGCCGCACCATGGACATCAGGGCTC CTGCTCAG) (SEQ ID NO:9) were used for PCR amplification of the entire kappa chain gene. The PCR product was inserted into p61.1 to form pNRX451. This plasmid is depicted in FIG. 9.

Example 3

EXPRESSION AND ISOLATION OF FINAL CLONE NRX451

C2-451C4-100NM HP-2 $\mu$M HP-161E 12–50 $\mu$M-12G4-3E7

CHO (dhfr-) (ATCC CRL 9096) cells were transfected in 6-well plates using Lipofectace® (Gibco) with linearized pNRX451 plasmid. Transfected cells were allowed to recover in Iscove's Modified Dulbecco's Medium (IMDM) (Gibco) containing 10% dialyzed Fetal Bovine Serum (dFBS) (Sigma) and 1X Hypoxanthine and Thymidine (Gibco). After 2 days of recovery, transfected cells were initially selected in IMDM containing 10% of DFBS and 800 $\mu$g/mL Geneticin® (Gibco) but lacking hypoxanthine and thymidine.

Surviving cells were subjected to gene amplification at 1000 cells/well in 96-well plates in IMDM containing 10% CIFBS and 100 nM Methotrexate (Sigma). Fourteen day supernatant were tested in gamma/kappa ELISA for antibody production. The highest producing wells were selected and pooled and designated C2-451C4-100 nM HP.

These cells were then amplified at 100 cells/well in 96-well plates in IMDM containing 10% DFBS and 2 $\mu$M Methotrexate. Fourteen day supernates were tested in gamma/kappa ELISA. The highest producing wells were selected and pooled and designated C2-451C4-100 nM HP-2 $\mu$M HP.

This pool was cloned at 1 cell/well in 96-well plates in IMDM containing 10% DFBS and 2 $\mu$M Methotrexate. Fourteen-twenty-one day supernates were tested in gamma/kappa ELISA. The highest producing clones were maintained in IMDM containing 10% dFBS and 2 $\mu$M Methotrexate and passed into IMDM containing 10% dFBS and 10, 50 or 200 $\mu$M Methotrexate.

The highest producing clone was selected (C2-451C4-100 nM HP-2 $\mu$M HP-161E12–50 $\mu$M) and subjected to 2 rounds of limiting dilution cloning in 96-well plates in IMDM containing 10% dFBS and 50 $\mu$M Methotrexate before cell banking. The final clone was designated C2-451C4-100 nM HP-2 $\mu$M HP-161E12–50 $\mu$M-12G4-3E7 (hybridoma producing the antibody was deposited with American Type Culture Collection (10801 University Blvd., Manassas, Va. 20110 ATCC Accession No. SD3273, converted to ATCC Accession No. CRL-12360)

Example 4

IMMUNOREACTIVITY OF NRX451

Figure 11:
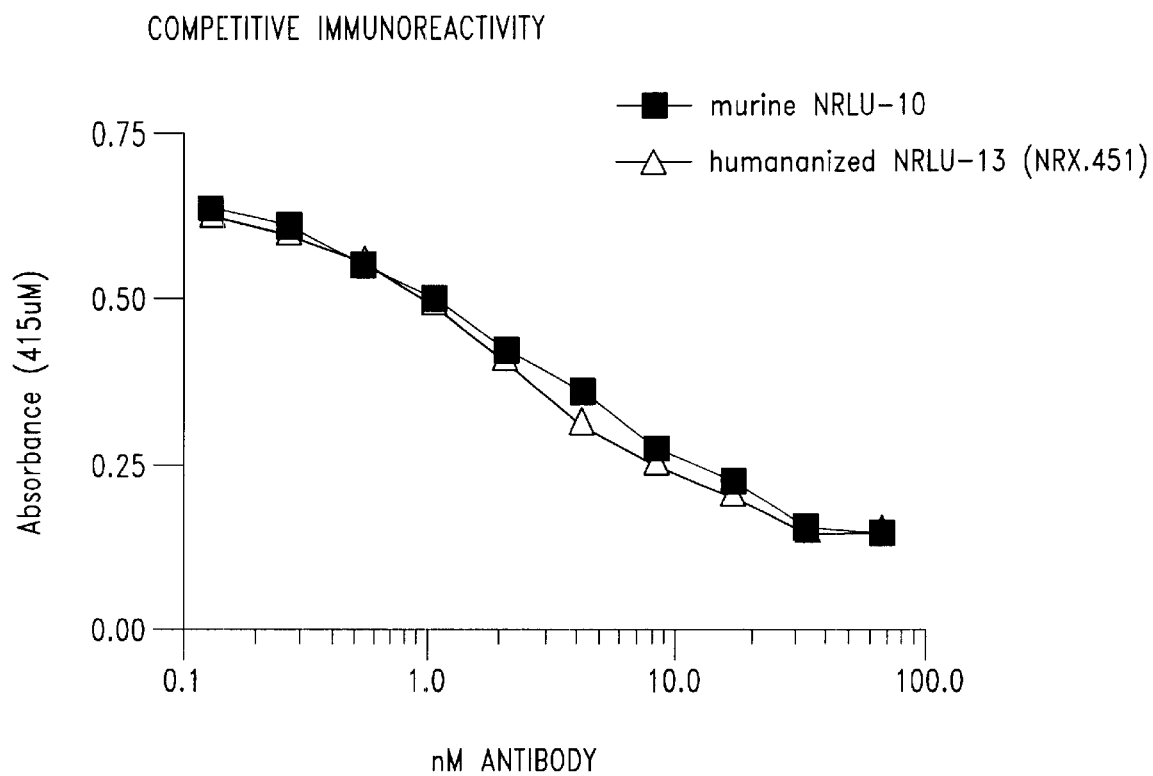
FIG. 11 compares immunoreactivity of humanized NRX451 antibody to intact NR-LU-10 antibody by competitive immunoreactivity.

The humanized NRX451 antibody was shown to exhibit immunoreactivity as determined by competitive immunoreactivity ELISA using the murine NRLU-10 as a comparison. These results are shown in FIG. 11. These results demonstrate that the humanized antibody exhibited greater than 65% of the immunoreactivity of NRLU-10.

The protocol for the competitive immunoreactivity ELISA is set forth below.

Competitive Immunoreactivity ELISA

Immunoreactivity is assessed in a competitive binding ELISA where standard murine NRLU-10 and test antibodies are allowed to compete with peroxidase-labeled murine NRLU-10 for binding to an NP40 (Sigma) extract of the KSA antigen-positive LS174 cell line.

Plate preparation: Coat 96-well plate with 100 $\mu$L/well optimized dilution of NP40 extract of LS174. Incubate to dryness overnight at 37° C.

Reagent Prep:
 Diluent: PBS+5% Chicken serum (Sigma)+0.5% Tween 20 (Sigma) (PCT)
 Standard and test antibodies:
  Dilute standard and test antibodies to 12 $\mu$g/mL in PCT. Perform 9 log2 dilutions in PCT.
 Peroxidase-NRLU-10:
  Dilute to optimized concentration in PCT.
  Add 100 $\mu$L Peroxidase-NRLU-10 to 500 $\mu$L of each dilution of standard and test antibodies for final concentrations of 10 $\mu$g/ml (66.67 nM) to 0.2 $\mu$g/mL.

Assay: Wash plate in PBS+0.5% Tween 20 using automated plate washer.
 Add 100 $\mu$L each dilution in duplicate to plate.
 Incubate at room temperature for 60 minutes. Wash as above.
 Add 100 $\mu$L Substrate buffer to each well. Incubate at room temperature for 30 minutes. Read on automated plate reader.

Calculations: Following a log-logit transformation of the data where curves are fit to the same slope, the concentration of the unlabeled competitor antibody required for 50% inhibition (k) is determined.

k standard/k test×100=% Immunoreactivity.

Example 5

Figure 12:
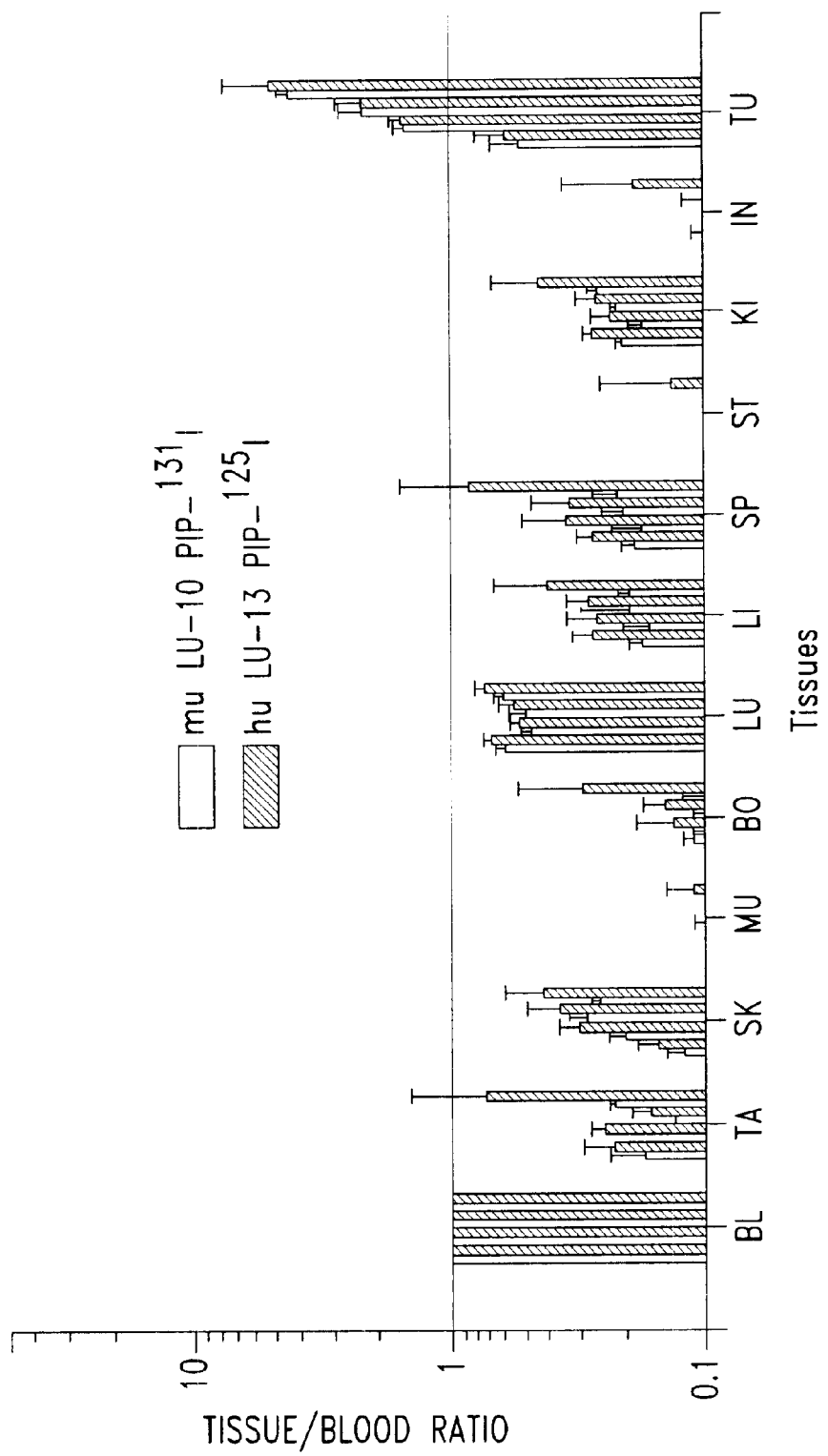
FIG. 12 compares the tissue biodistribution of different radiolabeled antibodies including humanized antibodies produced according to the invention.

Some variability in tissue uptake of radiolabeled antibodies from study to study is observed. The best method for in vivo comparison of two different antibody constructs involves labeling each with different isotopes (e.g., I-131 and I-125) and co-injecting an equimolar mixture of the antibodies into tumored nude mice. Experimentally, this removes a degree of inter-animal variability from the biodistribution data. This was done for comparison of CHO-produced humanized NR-LU-13 ("NRX451") and hybridoma-produced murine NR-LU-10. As these are two fundamentally different proteins, some differences in absolute pharmacokinetics were expected, and were observed. However, when correcting for the differing blood-pool concentration present in each tissue, these two proteins were found to exhibit analogous profiles of biodistribution at all timepoints. This may be appreciated from FIG. 12. The value shown in FIG. 12 are the ratios defined by taking (% injected dose/gram of tissue) divided by the (% injected dose/gram of blood) for each antibody construct. Tissues sampled were blood, tail (the site of injection), skin, muscle, bone, lung, liver, spleen, stomach, kidney, intestines, and tumor (subcutaneous SW-1222 colon carcinoma xenografts). With one exception, the average values of all tissues remained below 1.0 for all major organs and tissues, indicative of little specific retention of radiolabeled antibody beyond the blood-born contribution of radioactivity. The exception is tumor, where both constructs show consistent increasing, specific localization over time of nearly identical magnitude. The data support the in vitro assessment that fall immunoreactivity is retained by the humanized construct, and that little perturbation in the overall non-target tissue biodistribution has been imparted by the humanization process.

Despite the fact that neither the CHO nor the larval NRX451 has been produced in GMP purity, a preliminary dual label co-inject study was performed in the same xenograft model as above. The results of biodistributions performed at 4, 24, 48, and 168 hours after co-injection of the proteins showed they possess remarkably similar overall localization patterns. Also by flow cytometry there was no detectable binding of any of NR-LU-10 to red blood cells, granulocytes, monocytes, or lymphocytes.

Figure 13:
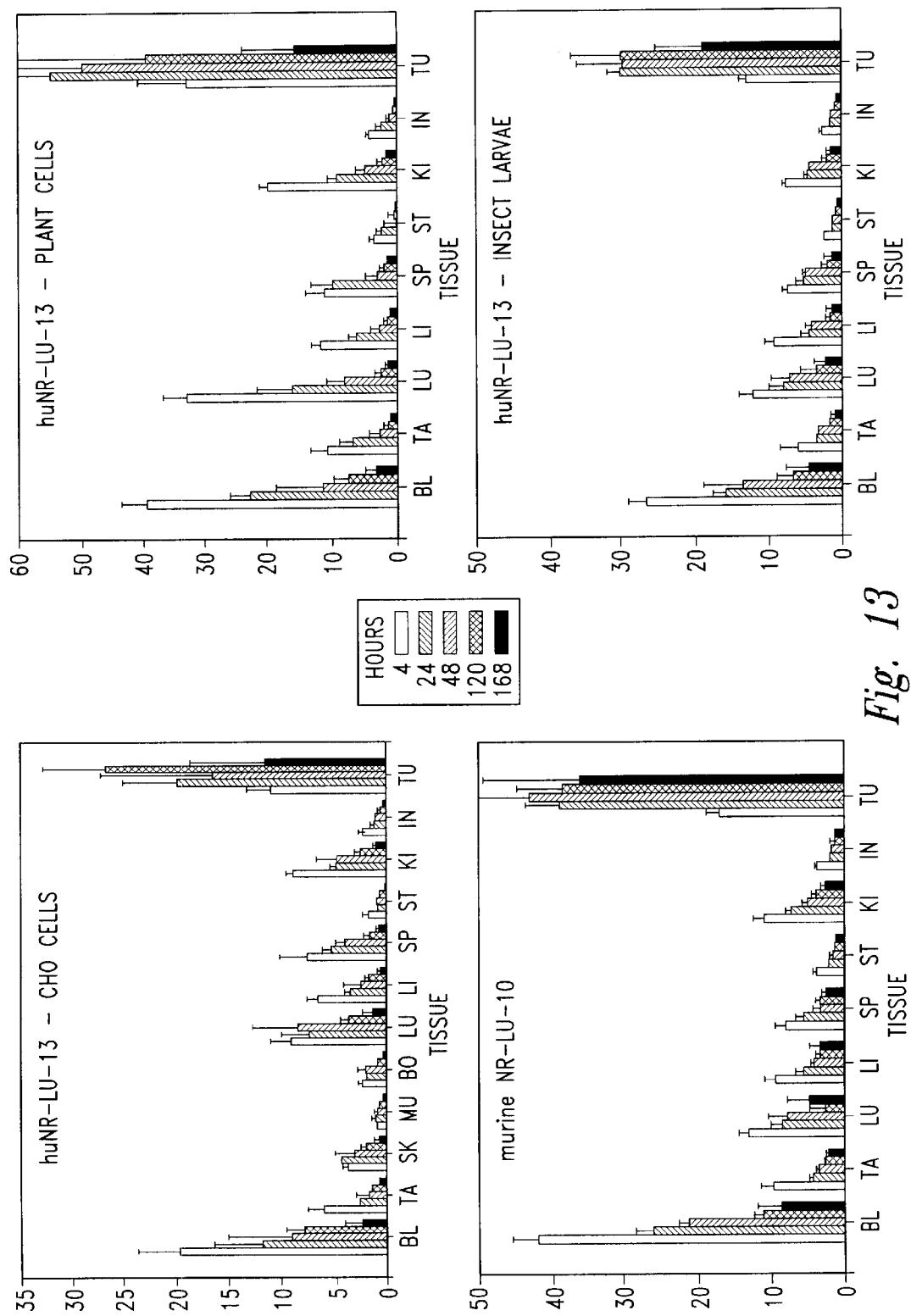
FIG. 13 compares the biodistribution of humanized NR-LU-13 (NRX451) expressed in CHO cells, plant cells, and insect larvae to murine NR-LU-10 produced in mouse hybridoma cells.

Pharmacokinetic and biodistribution analyses of each form of NRX451 were carried out in nude mice bearing a human colon carcinoma xenograft (SW1222). FIG. 13 shows the biodistribution of NRX451 produced in CHO cells, tobacco plant cells, and insect larvae. The antibody in each instance was radiolabeled with $^{125}$I. Four mice per group were injected by the tail vein with either 50 or 100 $\mu$g of antibody. Distribution of the radioactivity in the blood, tail, lung, liver, spleen, stomach, kidney, intestine and tumor was determined at 4, 24, 48, 120, and 168 hours.

The overall pattern shows a consistent declining concentration of antibody in the blood and all soft tissues at successive time points. In vivo immunoreactivity is demonstrated by the positive ratio of tumor to blood counts at all time points from 24–168 hours and by the increase in tumor counts over the 0–48 hour period. No significant non-target retention of radiolabel was evident beyond the blood pool activity in each organ.

EXAMPLE 6

CHEMICAL MODIFICATION OF NRX 451

The oxidation/reduction method used for the chemical modification of NRX451, produced according to Examples 1 through 3 is described. In this example, 50 mg of CHO produced NRX451 was diluted to 5.0 mg/ml with phosphate buffered saline (PBS) in a 50 ml Erlenmeyer flask. The solution was stirred constantly throughout the procedure at 150 rpm using a magnetic stir plate. Added to the antibody solution was 1.0 ml (10%v/v) of 0.4 M sodium phosphate, pH 7.0, making the pH of the final solution 7.0. Methionine (8.2 mg) was then added to the reaction mixture such that the final concentration is 5.0 mM. For the oxidation step, 117.6 mg of sodium meta periodate (NaIO$_4$) was added to the stirred antibody solution to achieve a final concentration of 50 mM. The oxidation reaction was allowed to stir for 20 minutes at 25° C. and then the reaction mixture was quenched with 310 $\mu$l of ethylene glycol. After an additional 20 minutes, the reaction mixture was diluted to 2.0 mg/ml with cold 0.5 M sodium borate at pH 9.0 (25% of final volume) and 7.44 ml of PBS.

For the reduction step, the above solution was cooled to 4° C. in an ice bath followed by an addition of 94.6 mg of sodium borohydride (NaBH$_4$) to obtain a final concentration of 100 mM. After stirring at 4° C. for 3 hours, the mixture was treated with sodium tetrathionate and the oxidized/reduced antibody solution was then buffer exchanged into PBS, a suitable storage buffer.

Figure 14:
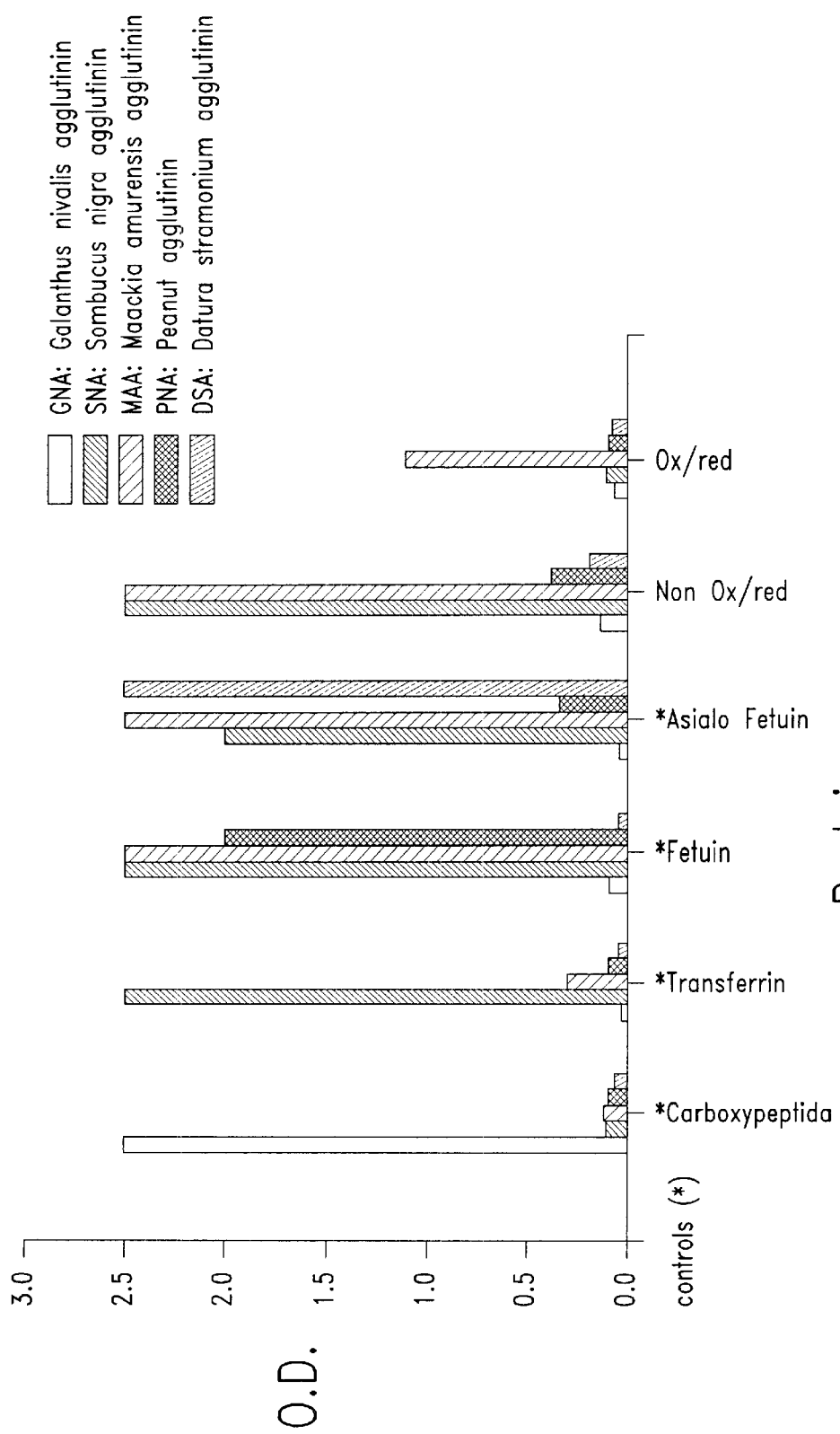
FIG. 14 compares the lectin binding profiles of the oxidized/reduced and non-oxidized reduced NRX451.

The lectin binding profiles of the oxidized/reduced CHO produced NRX451 and non-oxidized/reduced CHO produced NRX451 were compared to determine the extent of carbohydrate modification. There is a noticeable change in the lectin binding profiles of NRX451 and oxidized/reduced NRX451 as can be seen in FIG. 14. The terminally linked sialic acid alpha (2-) to galactose or N-acetylgalactoseamine and a galactose-B (1-40-N acetylglucosamine present on the non-oxidized NRX451 have been altered. Both of these carbohydrates are susceptible to oxidation by periodate and appear to be perturbed.

Figure 15A:
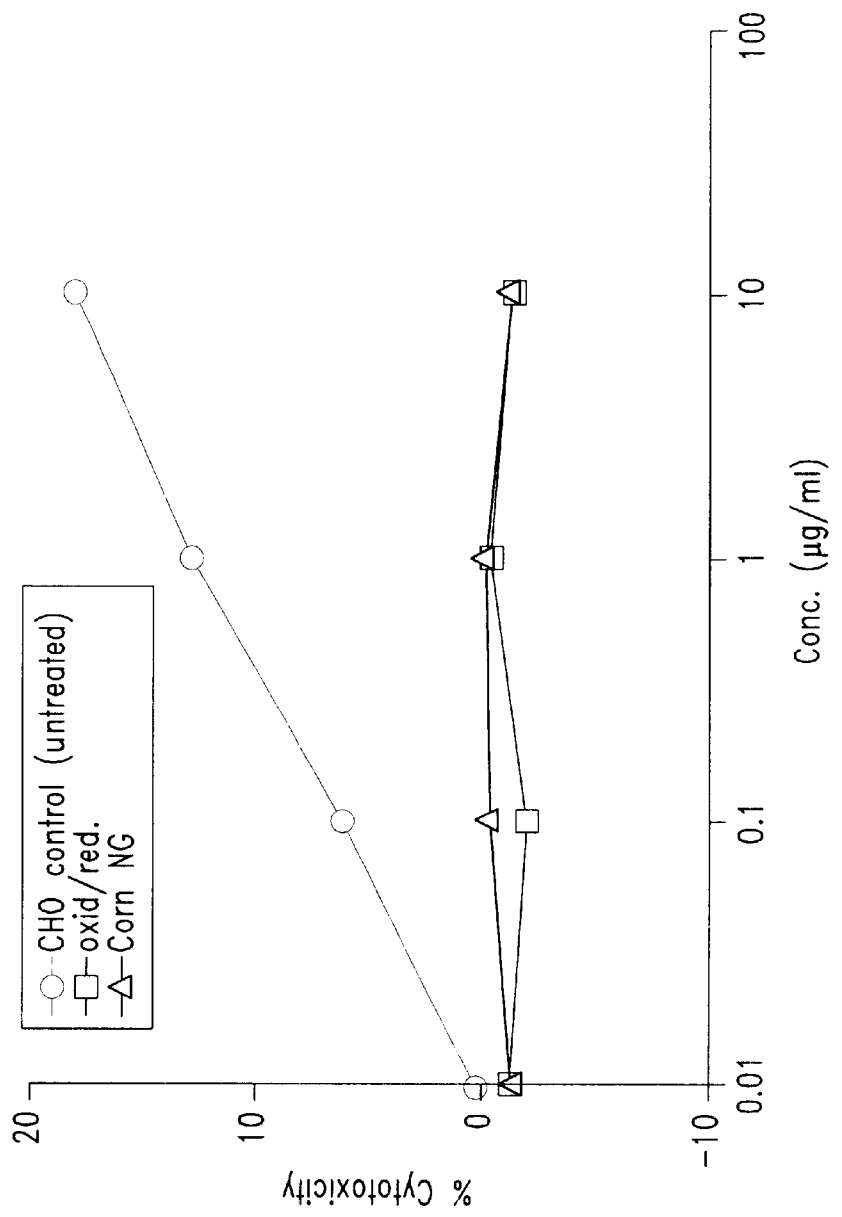
Figure 15B:
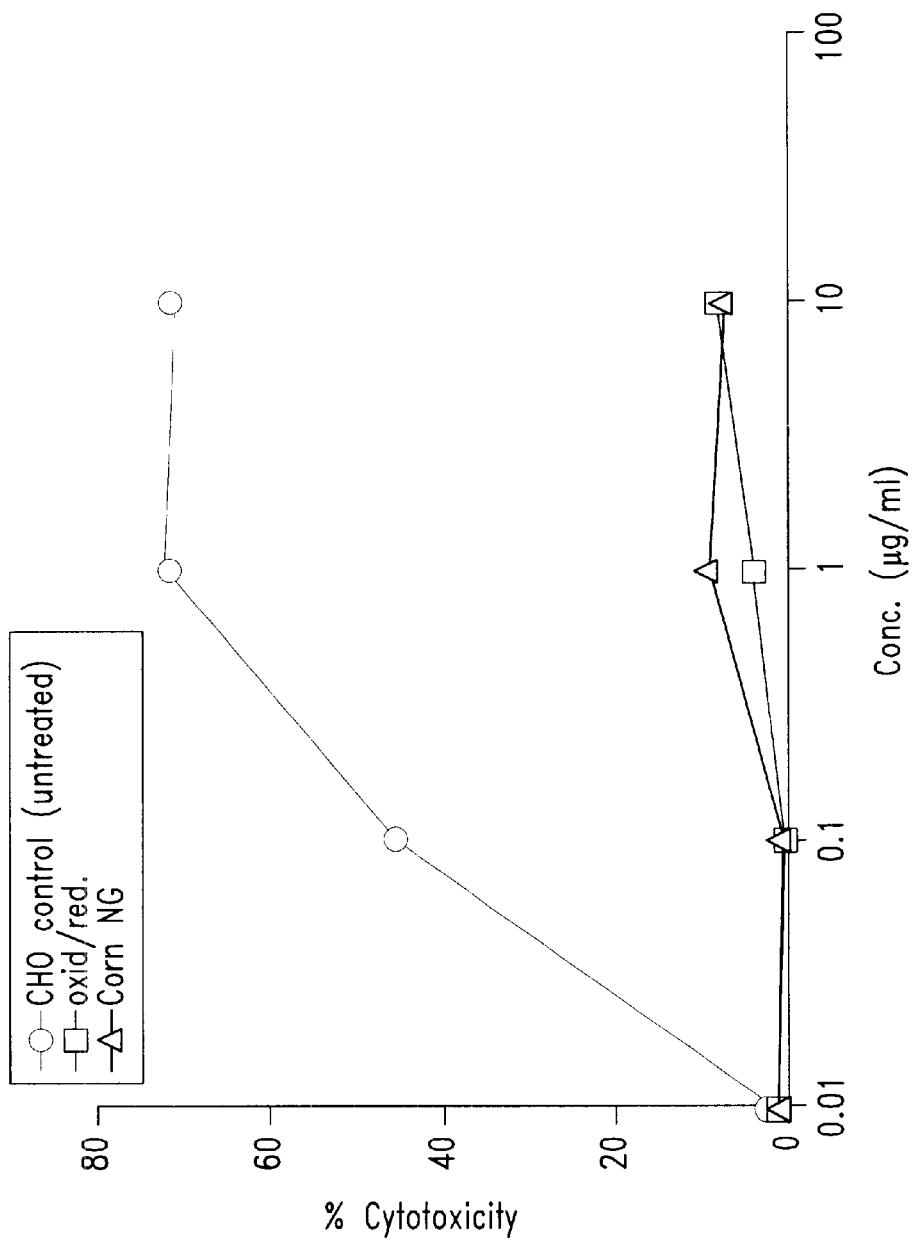
Figure 15C:
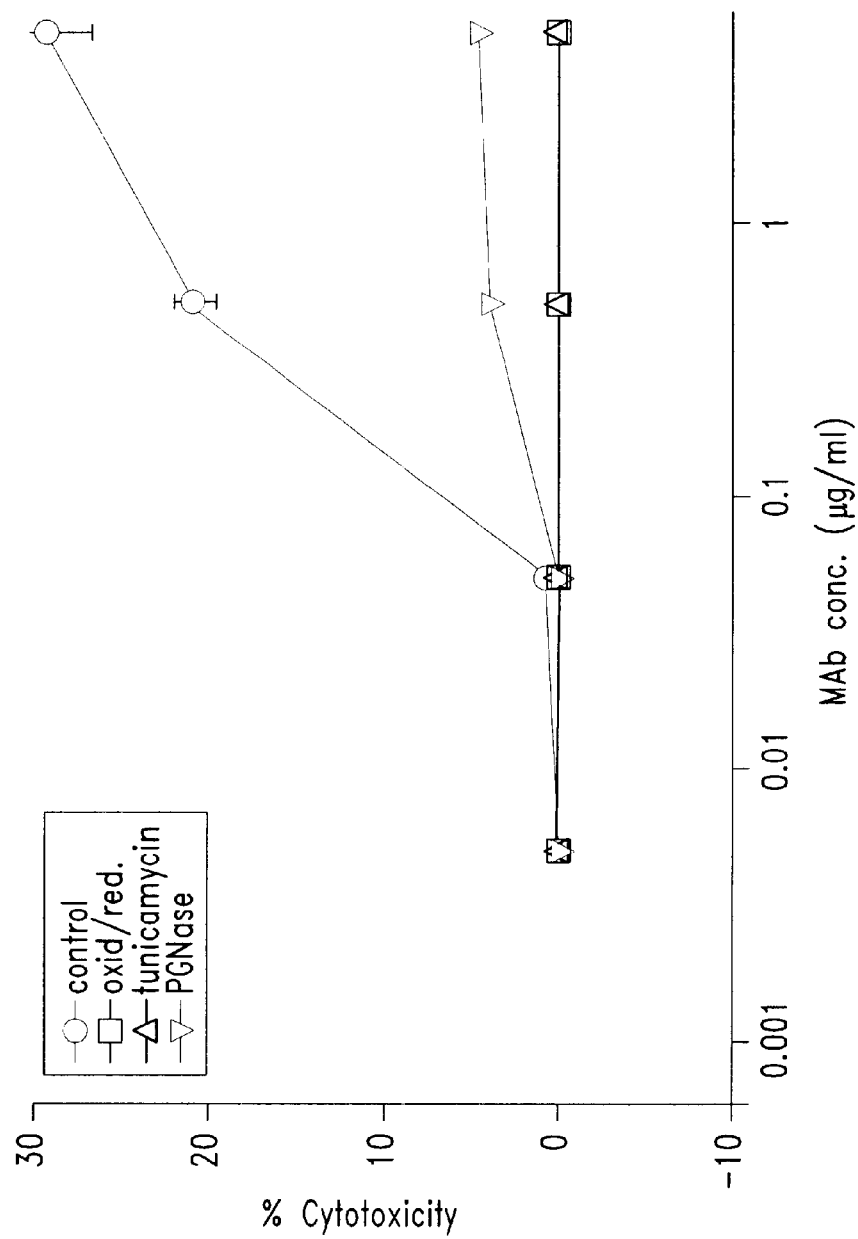
Figure 15D:
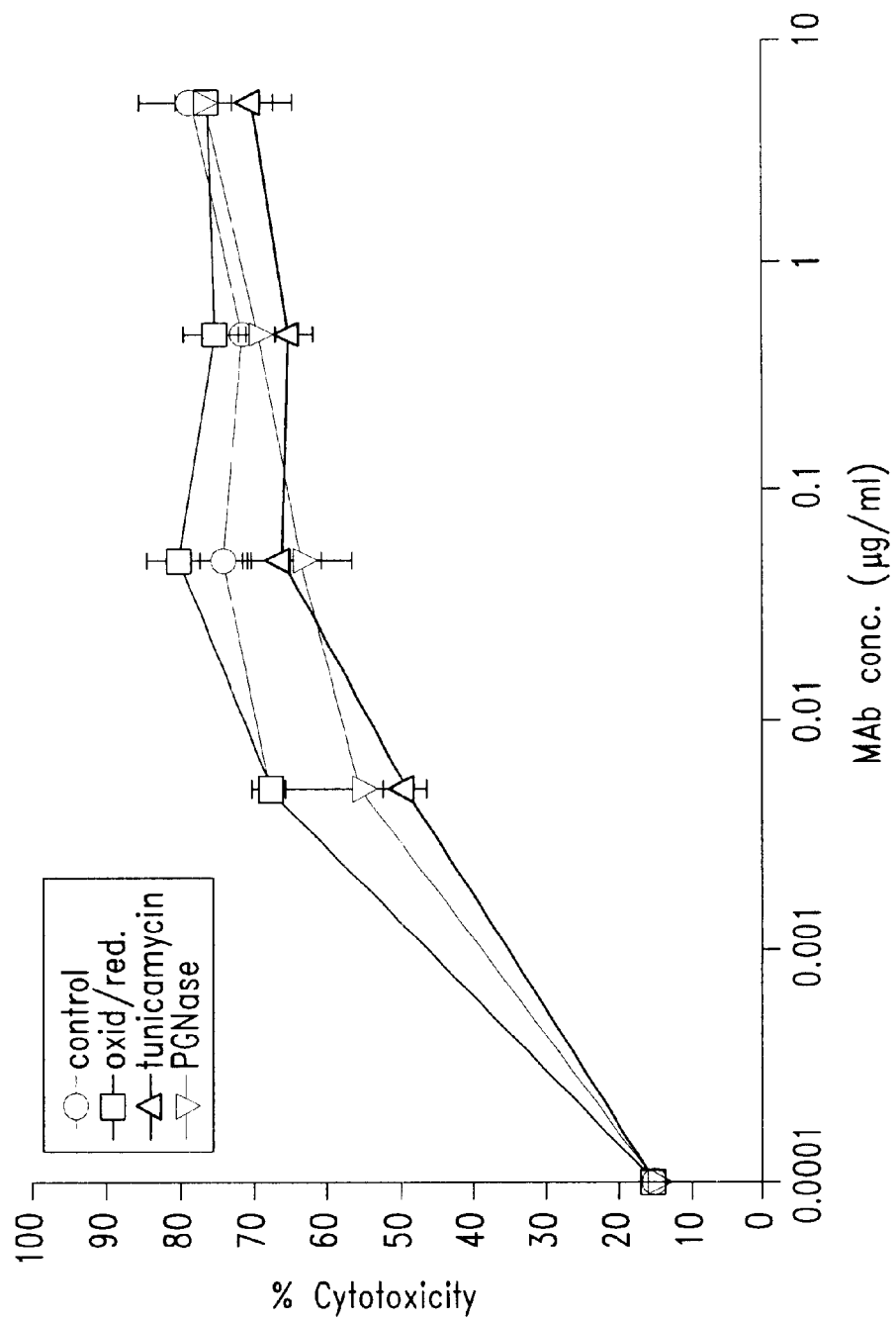
FIG. 15d depicts antibody dependent cellular cytotoxicity (ADCC) activity in unmodified and modified NRX451.
Figure 16A:
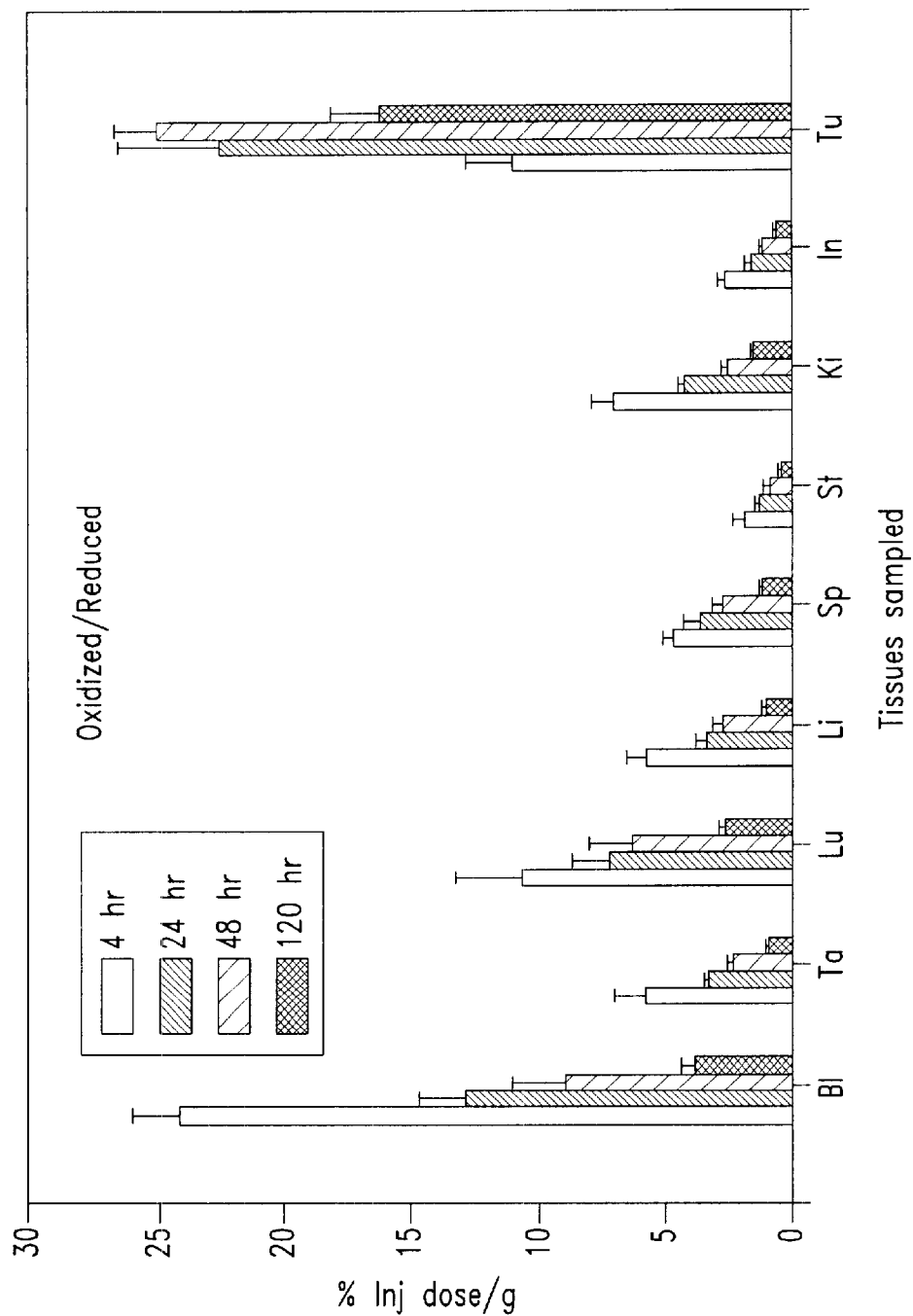
FIGS. 16a–16c compare the biodistribution of 50/50 coinjection of labeled NRX451 and oxidized/reduced NRX451 in a mouse model.
Figure 16B:
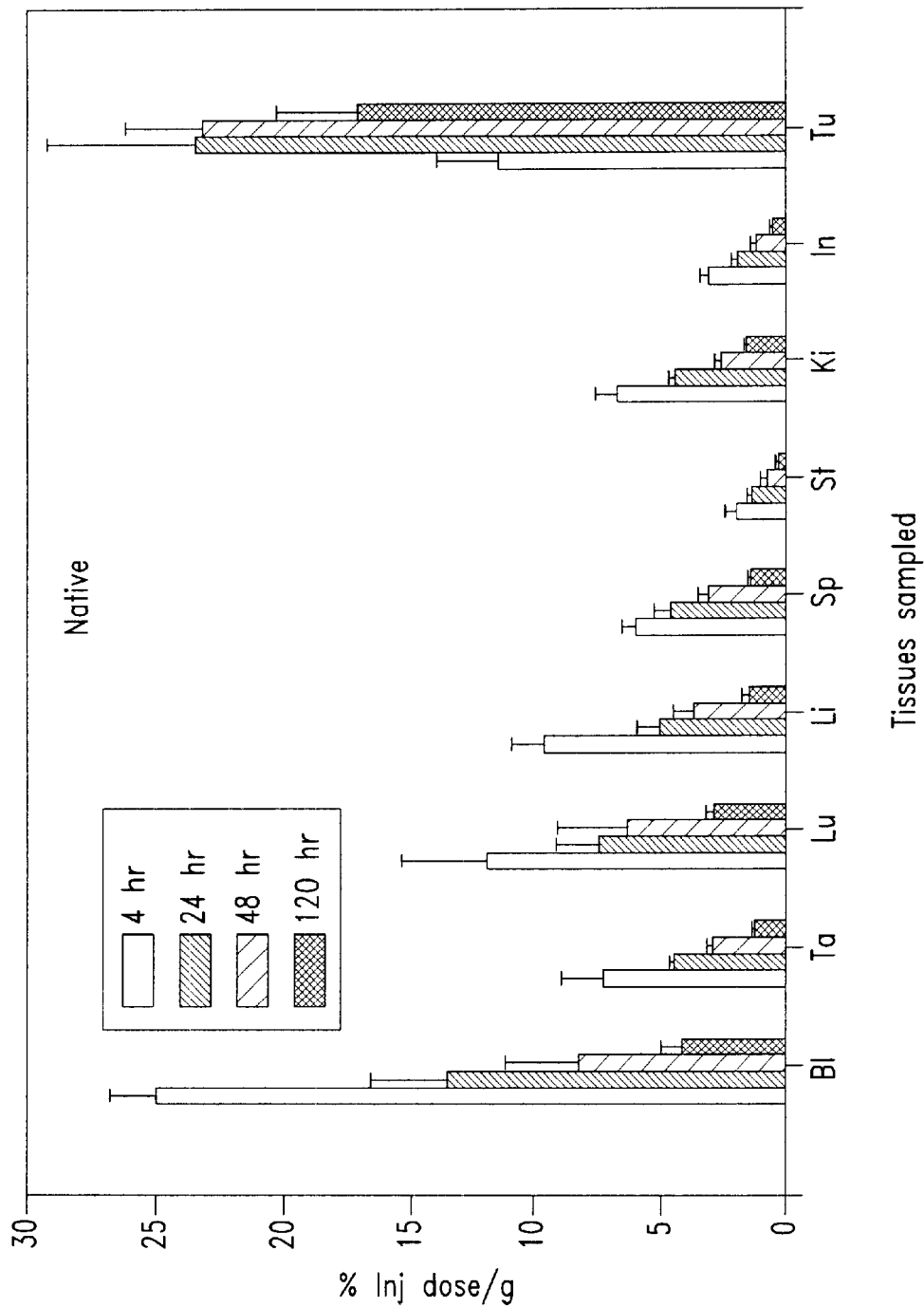
Figure 16C:
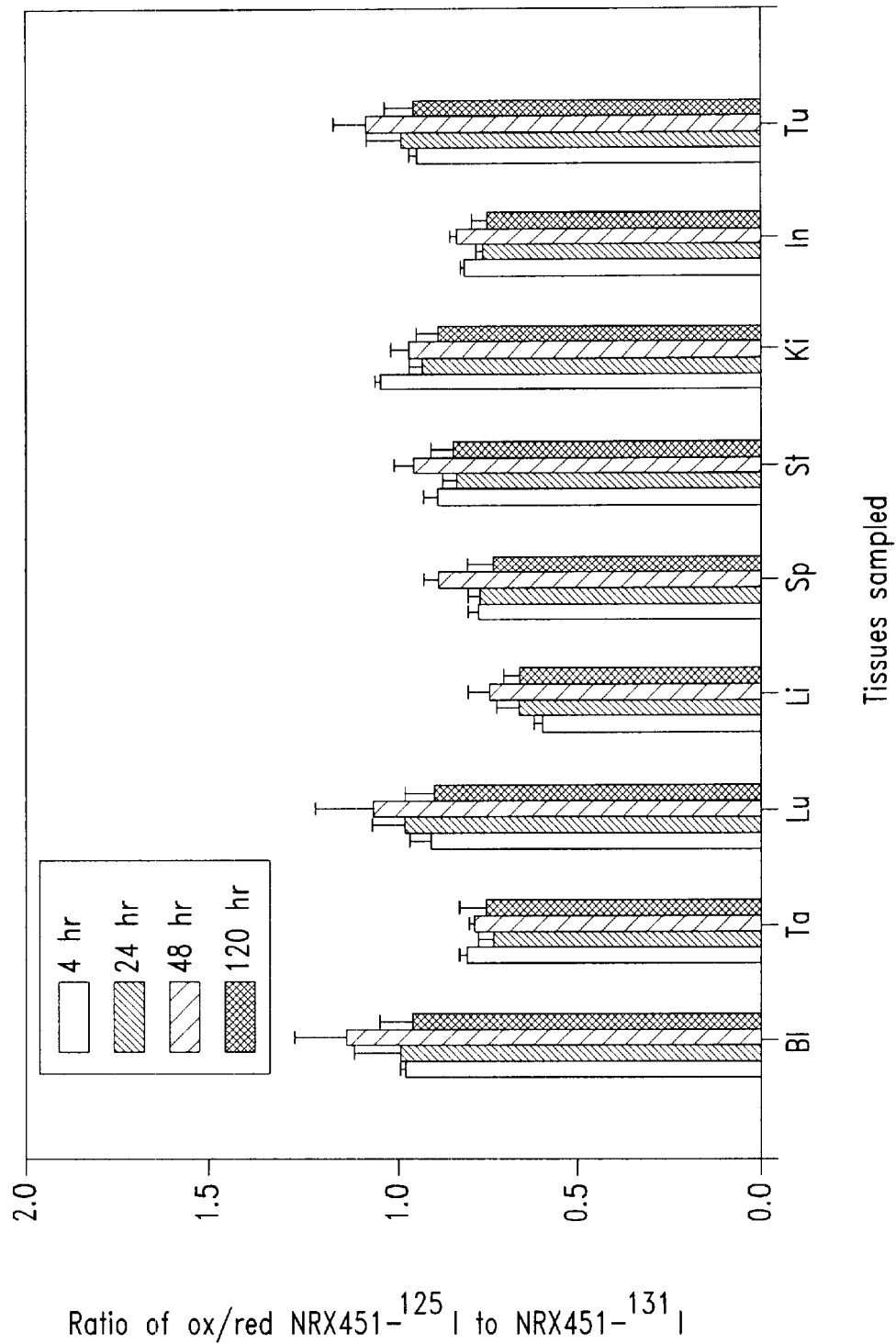

The C'MC and ADCC assays were performed on two different cell lines MCF-7, ATCC No. HTB 22 and SW1222 which express the antigen reactive with NRX451. FIGS. 15a and b illustrate that there is very little C'MC activity associated with the oxidized/reduced NRX451. However, untreated NRX451 has high levels of C'MC activity. FIG. 15c shows two controls of NRX451, one which has been deglycosylated using N-glycosidase F (PNGase F), an enzyme that is known to hydrolyze all types of asparagine bound N-glycans. The other control is NRX451 that has been cultured in the presence of tunicamycin, a known glycosylation inhibitor. Both of the controls show reduced C'MC activity in the in vitro assays. FIG. 15d shows that the ADCC activity remains intact on all of the controls as well as the oxidized/reduced NRX451. When NRX451 and oxidized/reduced NRX451 were injected into a mouse model, the biodistribution was identical, as shown in FIGS. 16a, b, and c.

Figure 17:
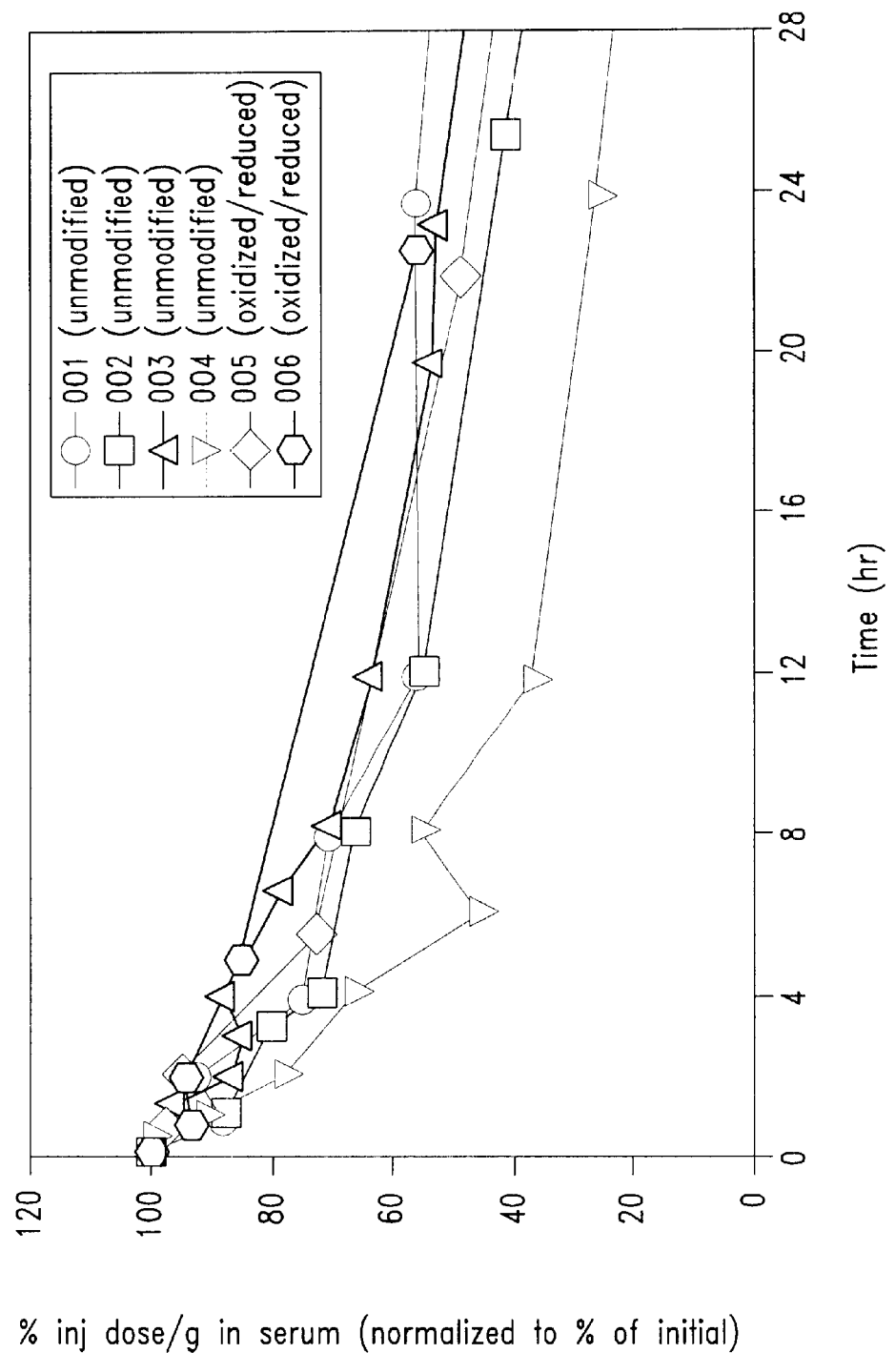
FIG. 17 compares the blood clearance of NRX451 and oxidized/reduced NRX451 in human cancer patients.

NRX451 and oxidized/reduced NRX451 was prepared according to GMP and an appropriate dosage amount following the pretargeting methodology was given to patients with cancer to observe and compare the blood clearance. FIG. 17 shows that the blood clearance of the two types of NRX451 was equivalent out to 24 hours post injection.

EXAMPLE 7

CLINICAL ACTIVITY OF CHO EXPRESSED NRX451

In one example of this technology, corn cells are transfected with an appropriate vector (e.g., U.S. Pat. Nos. 5,120,657; 5,015,580; 5,149,655; 5,405,779; 5,503,998; 5,506,125; 5,525,510 or 5,584,807) containing the genes for NRX451 and the deglycosylated mutant of NRX451. The deglycosylated mutant of NRX451 was made by creating a point mutation at position 297 (end of the $C_H2$ domain) on the heavy chain of an Asn to Gln thereby eliminating the N-linked glycosylation site. The antibodies were expressed and purified and tested for ADCC and C'MC against the human breast adenocarcinoma cell line MCF-7 (HTB 22 ATCC repository).

For the C'MC studies, MCF-7 cells (2×10$^6$) were labeled with $^{51}$Cr for 2 hours at 37° C. After multiple washings in culture medium (DMEM/F12, 10% fetal calf serum) the cells were added to 96 well, round bottom microtiter plates at 10$^4$ cells per well. NRX451 antibody produced in CHO cells (mammalian), produced in corn, and the deglycosylated mutant also produced in corn was added in log 10 dilutions starting at 5 ug/ml. In addition, human serum was added as a source of complement at a final dilution of 10%. The volumes of the wells were brought to 200 $\mu$l. After a 3.5 hour incubation period at 37° C., the plates were centrifuged and 100 $\mu$l volumes were collected from each well and counted in a Packard Gamma counter. In addition to specific release induced by the antibody and complement, spontaneous release of $^{51}$Cr was determined by collecting supernatants from wells containing cells alone. Total release was determined by adding 0.1% of NP40 to the wells and collecting 100 ul volumes as above. Specific release was calculated by subtracting spontaneous release from each test sample and the total releasable and dividing the adjusted test release by the adjusted total release (percent cytotoxicity). All samples were collected in triplicate and the data presented as the mean and standard deviation of these values.

In the case of ADCC analysis, the same procedures were used as described for C'MC except that in place of 10% human serum, human peripheral blood lymphocyte effector cells were added at an effector to target cell ratio of 25:1. The plate was centrifuged prior to the 3.5 hour incubation assay to facilitate effector and target cell binding.

Figure 18:
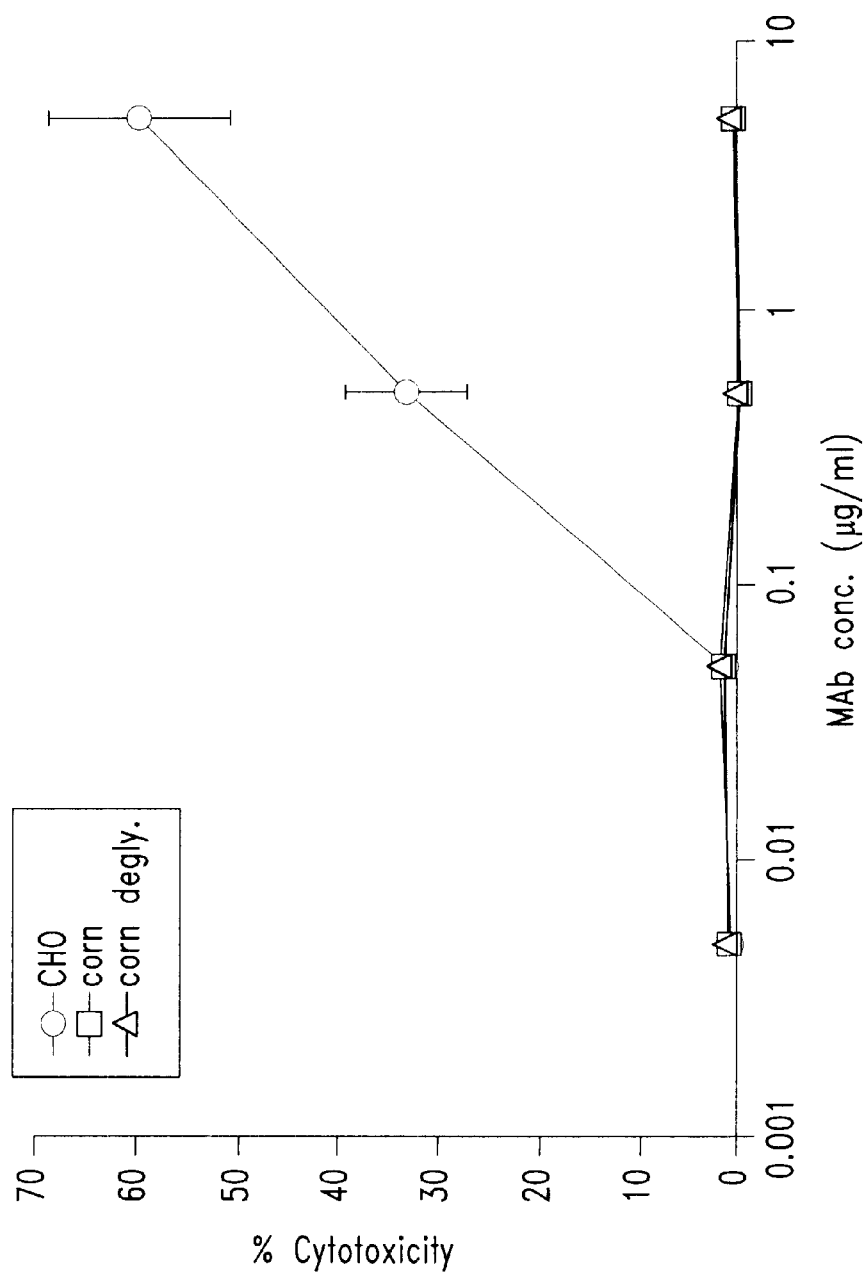
FIG. 18 depicts complement-mediated cytotoxicity of MCF-7 cells exposed to log 10 dilutions of CHO expressed NRX451 (-○-), corn expressed NRX451 (-□-) and the corn expressed Asn to Gln mutant of NRX451 (-Δ-). Human serum at a final dilution of 10% was the source of complement. Results are expressed as percent cytotoxicity.
Figure 19:
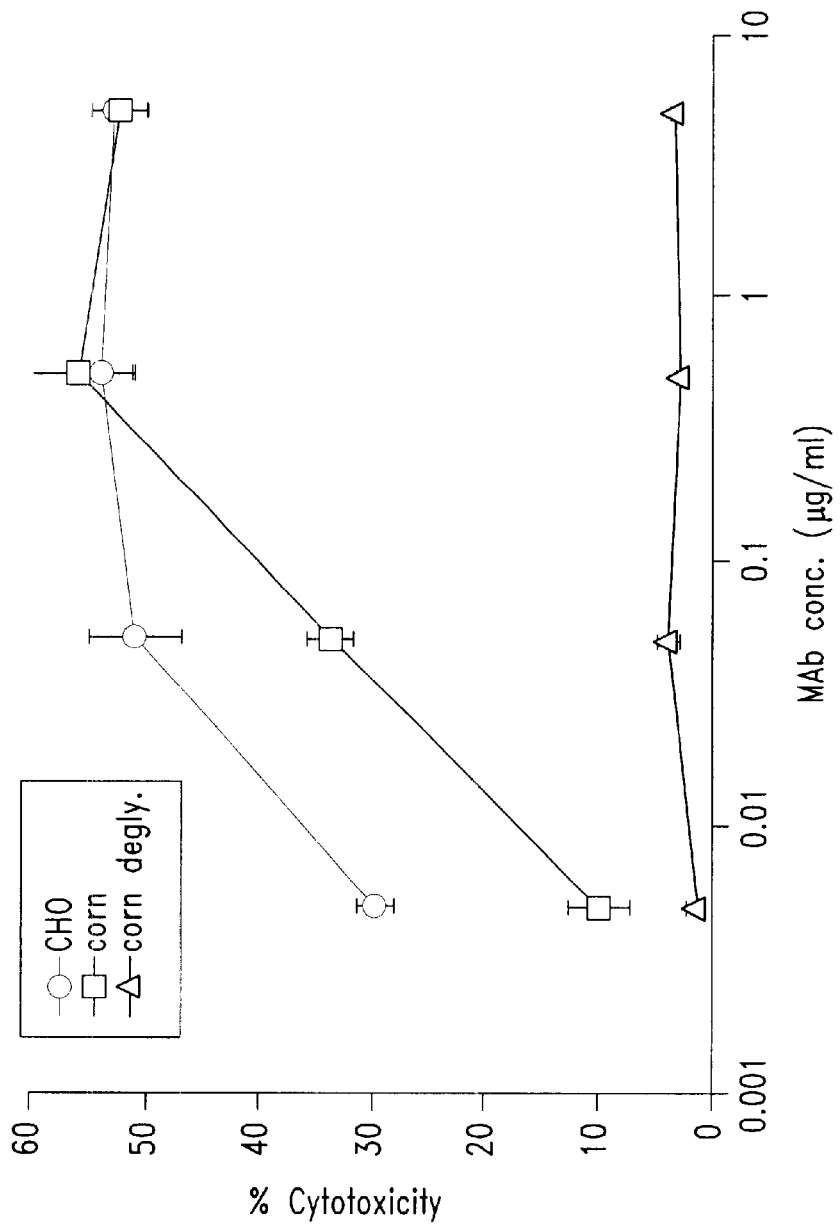
FIG. 19 depicts MCF-7 cells exposed to log 10 dilutions of CHO expressed NRX451 (-○-), corn expressed NRX451 (-□-) and the corn expressed Asn to Gln mutant of NRX451 (-Δ-). Human peripheral blood mononuclear cells were also added at an effector to target cell ratio of 25:1. The results are expressed as percent cytotoxicity.

The results show in FIGS. 18 and 19 that the NRX451 antibody produced in CHO cells efficiently mediates C'MC and ADCC. In addition, NRX451 produced in corn cells mediates ADCC but not C'MC. Finally, the Asn to Gln mutant produced in corn cells was completely ineffective in mediating either C'MC or ADCC.

These results indicate that one skilled in the art can produce IgG1 humanized antibodies that are unable to mediate C'MC because of post translational modification differences between plant and mammalian cell expression. In addition, a mutation of an Asn to Gln results in elimination of ADCC through disruption of a glycosylation site. Together these data indicate that one can tailor-make an antibody for effector function based on the selection of the expression system or a combination of a single site mutation for N-linked glycosylation and selection of a plant expression system.

EXAMPLE 8

SITE SPECIFIC MUTAGENESIS OF NRX 451

The N-glycosylation site in the $CH_2$-domain of the human immunoglobulin heavy chain was site specific mutagenized by polymerase chain reaction (PCR). Oligonucleotides NX156 (5' AGCAGTAC CAA AGC ACG TAC CGG GTG 3') (SEQ ID NO:10) and NX157 (5' TACGTGCTTTG GTA CTG CTC CTC 3') (SEQ ID NO:11) were synthesized (DNAgency, Malvern, PA) to anneal to the coding (NX156) and noncoding (NX157) strands of the human heavy chain gene over the region containing the N-glycosylation site (Asn-Ser-Thr). Both oligonucleotides contained a two-base mismatch designed to mutate a codon from, A., Caspgaragine) to CAA (glutamine). In the first round of PCR, NX156 was paired with a downstream primer NX113 (5' GCTGACGGAT CCTCATTTAC CCGGAGACAG GGAG 3') (SEQ ID NO:12) and NX157 was paired with an upstream primer NX110 (5' CCGTCTATTA CTGT-TCTAGA GAGGTC 3') (SEQ ID NO:13) in separate reactions using plasmid PNRX451 as a template and Ultma DNA polymerase according to the manufacturer's specifications (Perkin Elmer, Branchburg, N.J.). The resulting PCR products were 476 base pairs for the NX110/NX157 primers and 634 base pairs for the NX156/NX 113 primer pair; and comprised portions of the heavy chain extending upstream and downstream from the mutation, respectively. These PCR products were purified from agarose gels via Geneclean (Biolol, Vista, Calif.) and combined into a contiguous fragment in a second PCR using primers NX110 and NX113. The resulting PCR product was 1190 base pairs and contained the desired mutation. The product was digested with restriction enzymes SstII and BamHi to generate a 471 base pair fragment which was cloned into the expression vector pNRX451, replacing the N-glycosylation site containing wildtype gene fragment.

EXAMPLE 9

IN VIVO EVALUATION OF NRX451 WHOLE ANTIBODY PRODUCED IN CORN SEED

Purified NRX451 whole antibody from corn seed was radiolabeled with $^{125}I$ and compared with the CHO cell produced murine NR-LU-10 whole antibody radiolabeled with $^{131}I$. An equimolar mixture of the two antibodies (25 µg/25 µg) was injected intravenously into nude mice (20–25 g) bearing sub-cutaneous SW-1222 colon carcinoma xenografts, and blood clearance was assessed following i.v. injection of the same mixture into non-tumored mice.

Study#1:

T=0, i.v. injection of a mixture of 25µg $^{131}I$-murine NR-LU-10 whole antibody (muLU-10) and 25 µg $^{125}I$-corn-produced NRX451 whole antibody into nude mice (20–25 g) bearing subcutaneous SW-1222 colon carcinoma xenografts. Animals were sacrificed at 4, 24, 48, 120, and 168 hours after administration and dissected. Tumor and non-target tissues were weighed and counted for detection of $^{131}I$ and $^{125}I$. A separate group of non-tumored, Balblc mice were injected with the same mixture, and serial blood samples were taken to compare the rate of disappearance of radioactivity from blood.

Figure 20:
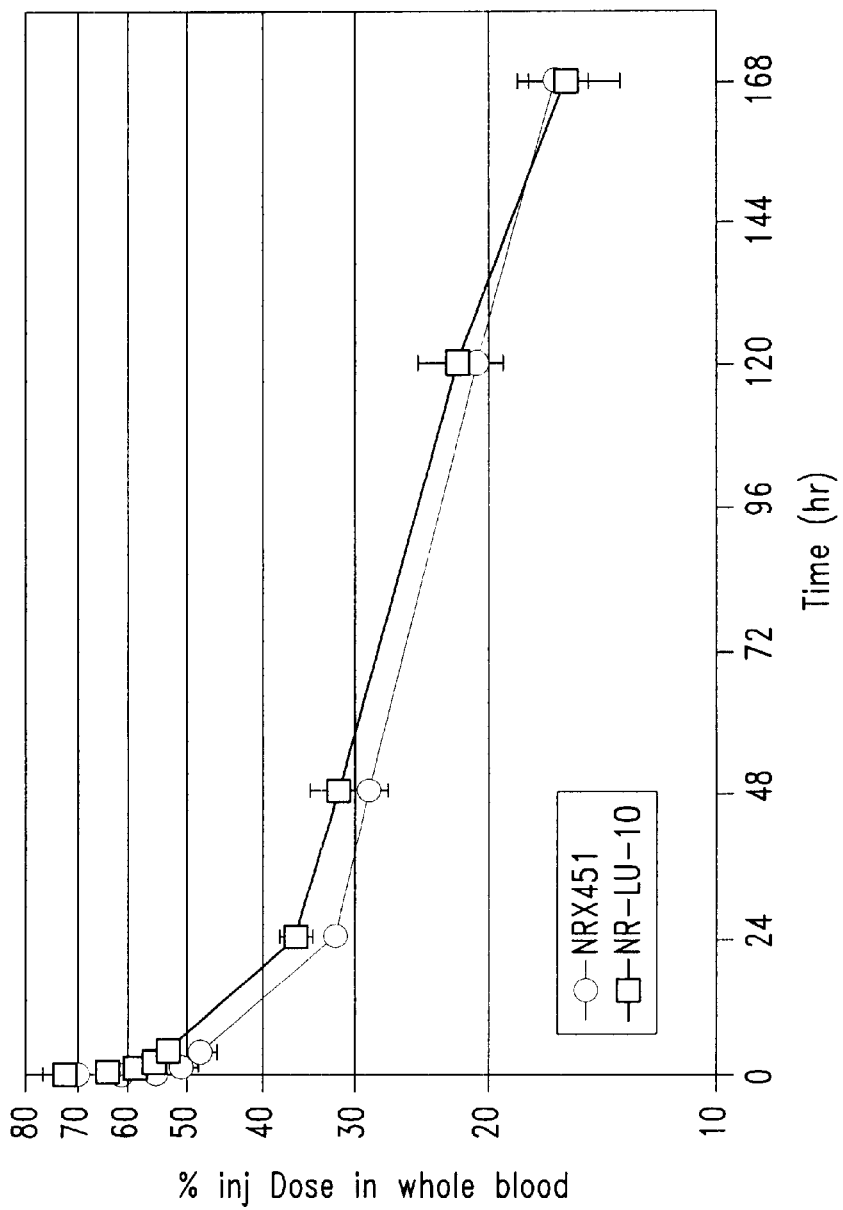
FIG. 20 compares the blood disappearance of NRX451 and the murine IgG analog, NR-LU-10, in mice.

Results:

As shown in FIG. 20, both isotopes were eliminated from the blood at nearly identical rates, both in the early (α-phase) distribution, and later elimination-dominated (β-phase) phase. Elimination half-lives were calculated to be 77.0 hr for the humanized NR-LU-13 antibody (huILu-13) versus 74.3 for the co-injected murine form. In terms of blood residence time, there is no appreciable difference between NRX451 whole antibody and murine NR-LU-10.

Figure 21A:
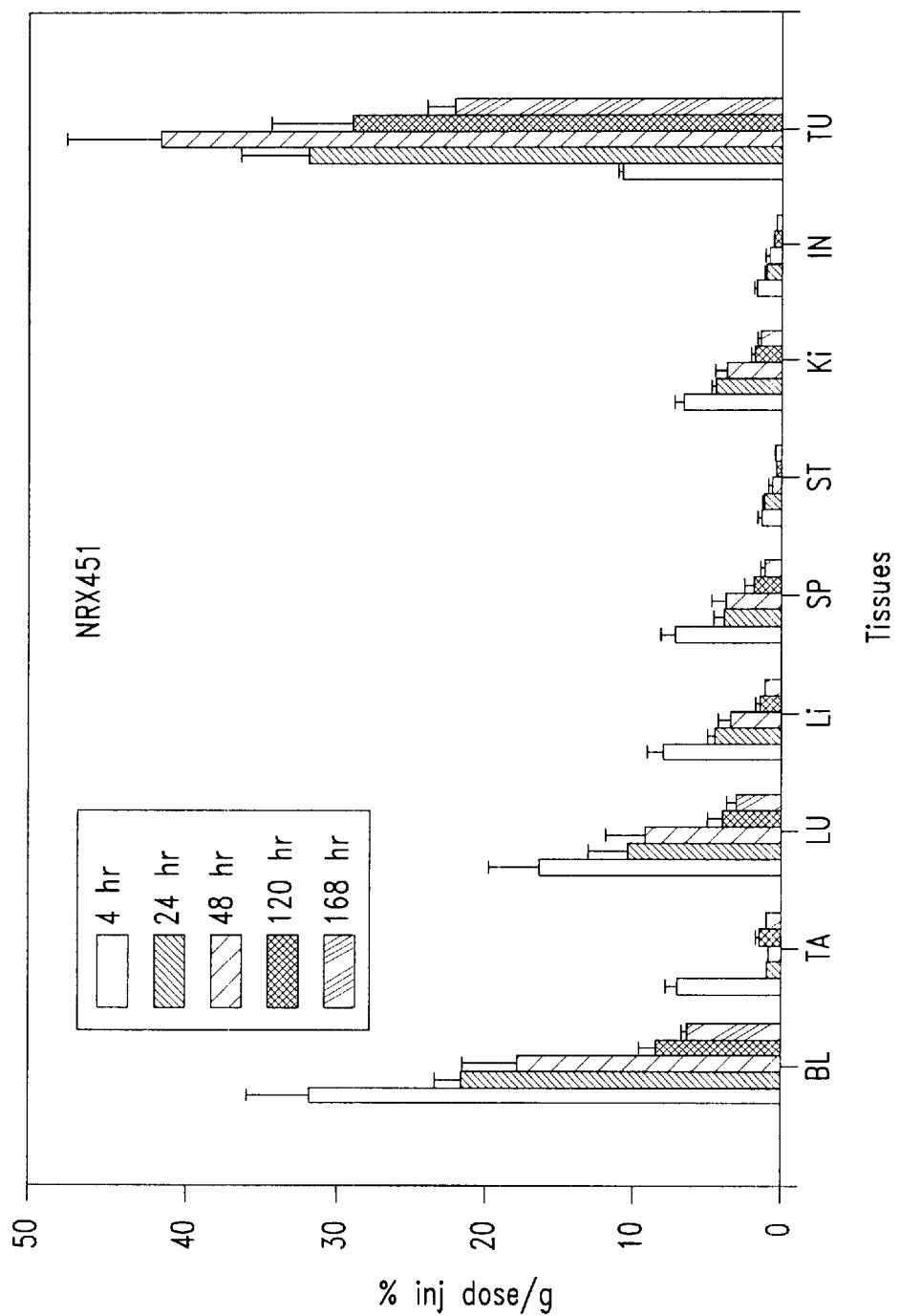
FIGS. 21a–21b compare the biodistribution in tumored athymic mice of NRX451 and the murine IgG analog, NR-LU-10.
Figure 21B:
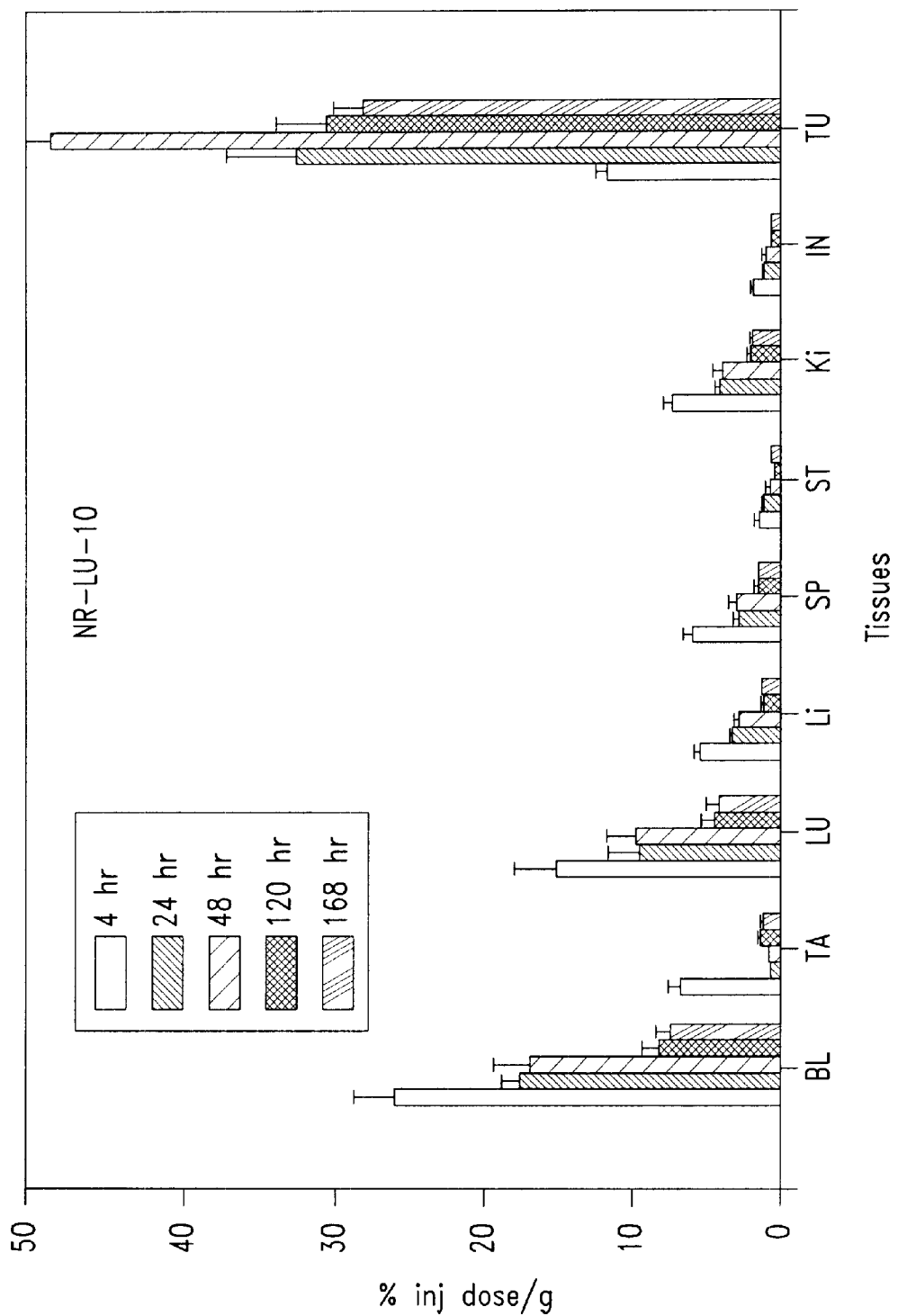

Biodistribution of the co-injected constructs were very similar, as well. Shown in FIGS. 21A and 21B are the blood, soft tissue and tumor concentrations of radioactivity in tumored nude mice at progressive time after administration. Both constructs show similar declining concentrations in all soft tissues, which follows the time-course of elimination from blood. There is little evidence of non-specific retention of radioactivity in any tissue, save tumor. The tumor uptake profile shows an increase in concentration of radioactivity out to 48 hours, with the % i.d./g values at 120 hours being diminished due to continued tumor growth (the actual amount, % i.d., of both isotopes in tumor at 120 hours is almost double that of any prior timepoints). Both the murine and humanized antibodies show quantitatively similar tumor uptake profiles, in terms of rate, extent, and retention of uptake. In the in vivo evaluation of each whole antibody, there is no appreciable difference between huNR-LU-13 whole antibody (expressed in corn seed) and the murine form (hybridoma cells).

Study #2:

Design:

T=0, i.v. injection of 50 µg $^{125}I$-NRX451 chemically conjugated to streptavidin (NRX451/SA) into nude mice (20–25 g) bearing subcutaneous SW-1222 colon carcinoma xenografts. Animals were sacrificed at 4, 24, 48, 120 and 168 hours after administration and dissected. Tumor and non-target tissues were weighed and counted for detection of $^{125}I$.

Figure 22:
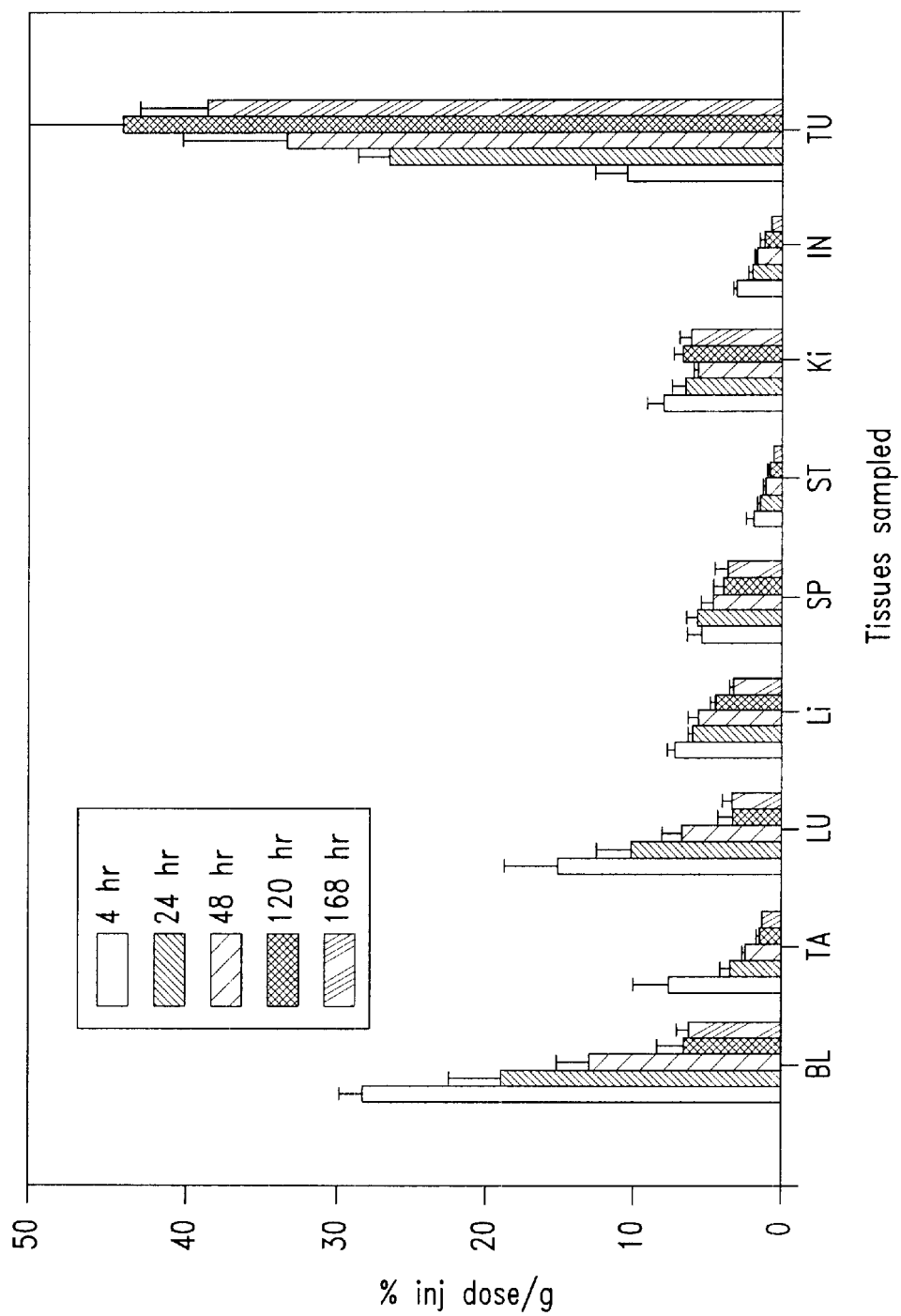
FIG. 22 depicts the biodistribution in tumored athymic mice of the N-linked glycosylated mutant NRX451 chemically conjugated to streptavidin (SA), expressed in corn seed.

Results:

Evaluation of the purified NRX451 whole antibody from corn seed continued with the chemical conjugation of this material to streptavidin, and subsequent utilization in pre-targeted tumor delivery. First, however, an evaluation of the streptavidin conjugate alone was done. Shown in FIG. 22 are the blood, soft tissue and tumor concentrations of radioactivity in tumored nude mice at progressive time after administration. There is little evidence of non-specific retention of radioactivity in any tissue, save tumor. The tumor uptake profile shows an increase in concentration of radioactivity out to 120 hours. The overall pattern shows a consistent declining concentration of antibody in blood and all soft tissues at successive timepoints. In vivo immunoreactivity is demonstrated by the positive ratio of tumor to blood concentrations at all timepoints from 24–168 hours, and by the increase in tumor localization over the 0–48 hour period. Tumor uptake peaking at 40–50% ID/g is similar to that observed with muNR-LU-10/SA, as well as the with the unconjugated antibodies described above. Tumor retention over time is similar to historical controls of muNR-LU-10/SA. Little significant non-target retention of radiolabel is evident beyond the blood pool activity in each organ at the timepoints 24–168 hours. High values in all well-perfused tissues at 4 hours may be related to high blood pool activity at this timepoint.

Study #2 (cont'd):

Design:

T=0, i.v. injection of 400 μg $^{125}$I-NRX451 whole antibody (corn seed) chemically conjugated to streptavidin (NRX451/SA) into nude mice (20–25 g) bearing subcutaneous SW-1222 colon carcinoma xenografts. t=20 hours, i.v. injection of 100 μg of synthetic clearing agent (GN16LCBT). t=26 hours, i.v. injection of 1.0 μg $^{111}$In-DOTA-biotin. Animals were sacrificed at 2, 24, 48, and 120 hours after administration of $^{111}$In-DOTA-biotin (28, 50, 74, and 144 hours from t=0) and dissected. Tumor and non-target tissues were weighed and counted for detection of $^{125}$I and $^{111}$In. Separate groups of non-tumored, Balb/c mice were injected with 400 μg $^{125}$I-NRX451/SA, followed at 24 hours with saline or 100 μg of synthetic clearing agent (GN16LCBT), and serial blood samples were taken to compare the rate of disappearance of radioactivity from blood.

Figure 23:
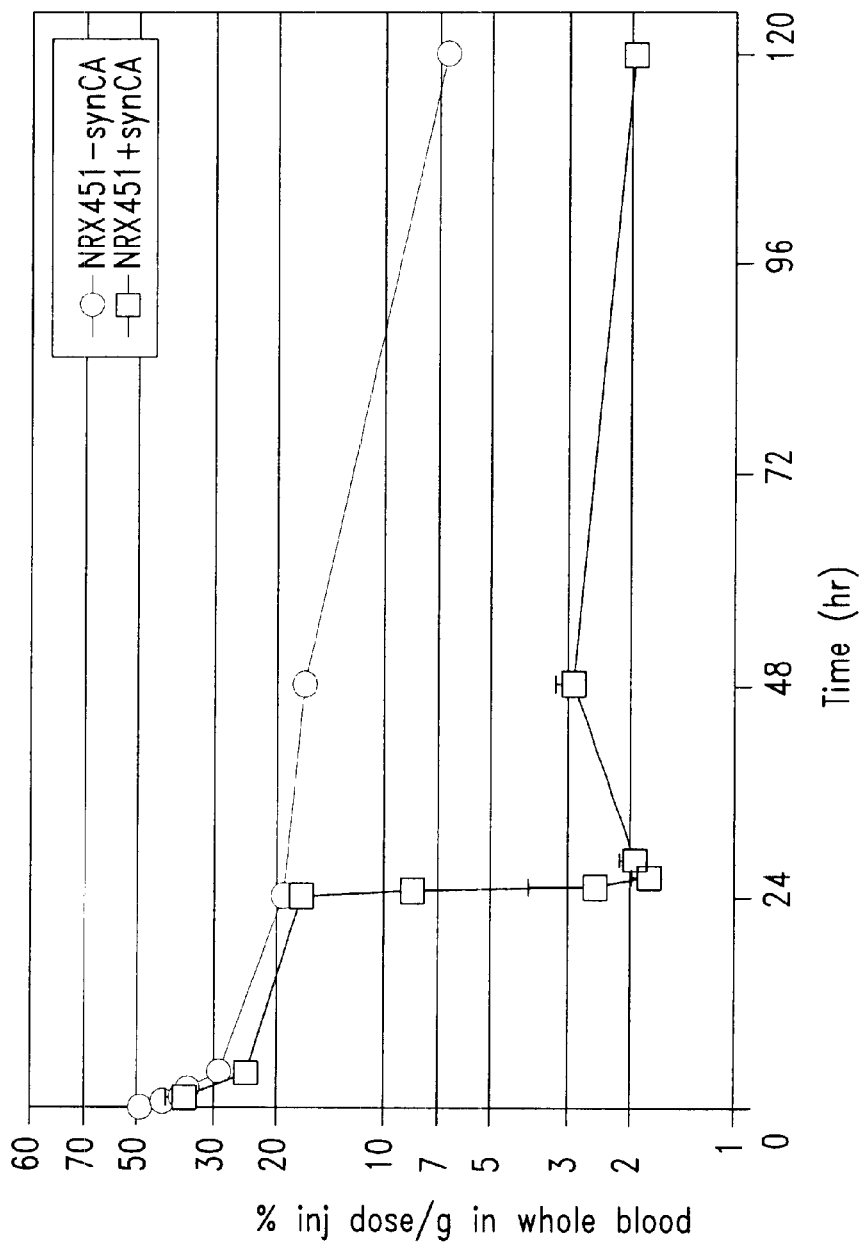
FIG. 23 contains results of the blood disappearance of the radiolabeled corn expressed N-linked glycosylated mutant NRX451/SA conjugate with and without the use of a synthetic clearing agent in mice.

Results:

As shown in FIG. 23, radioactivity was slowly eliminated from the blood in a manner similar to the unconjugated antibody, both in the early (α-phase) distribution, and later elimination-dominated (β-phase) phase. Injection of synthetic clearing agent at 24 hours produced a rapid decline of blood radioactivity to levels <10% of the original concentration. A slight rebound in blood radioactivity concentration (<1%) is seen from 24–48 hours, consistent with historical results achieved with the muLU-10/SA conjugate. The nadir in serum concentration was sufficient to produce a reduced background for pretargeting experimentation.

Figure 24A:
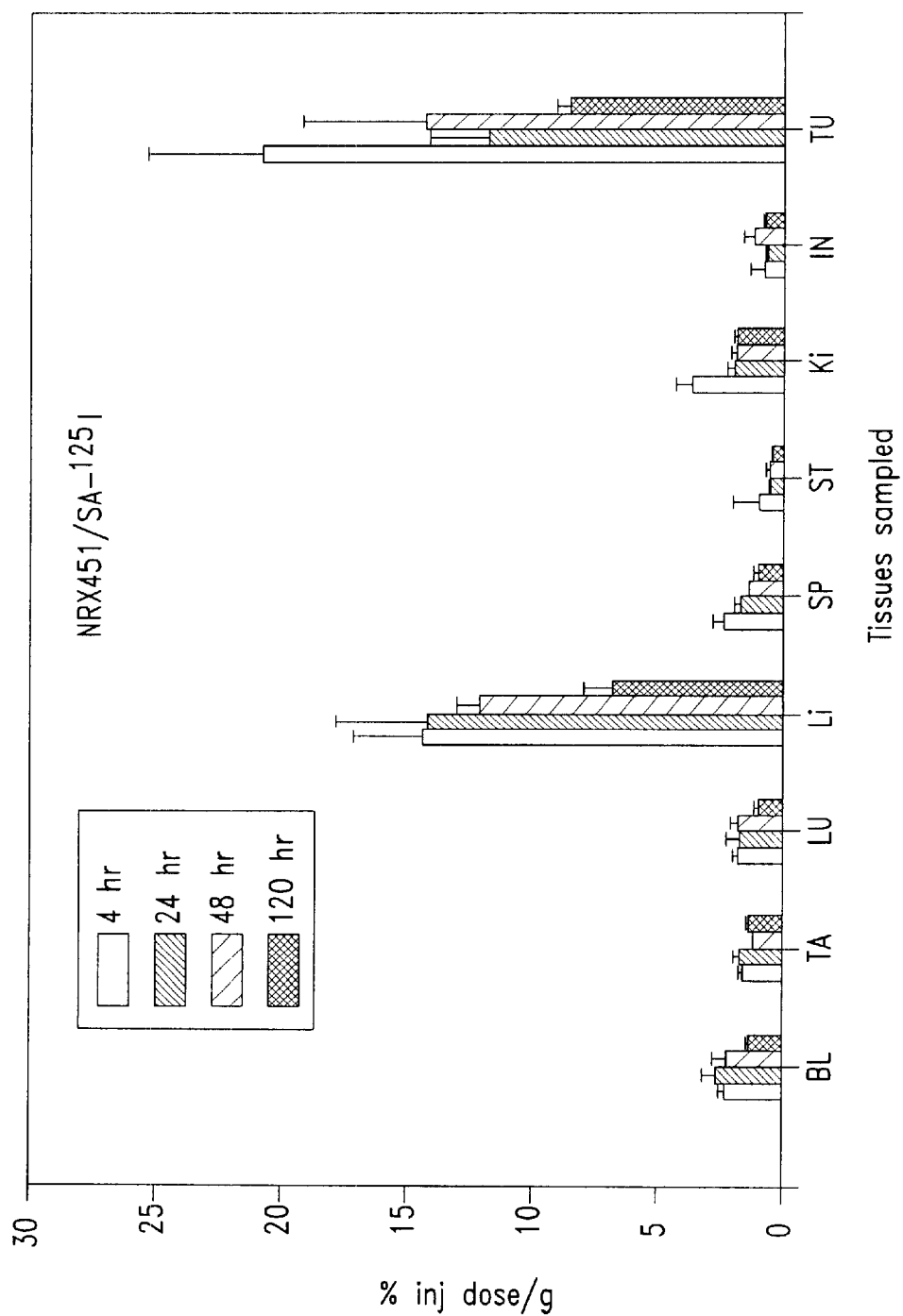
FIGS. 24a–24b contain the biodistribution in tumored athymic mice of the radiolabeled corn expressed N-linked glycosylated mutant NRX451/SA conjugate and subsequently administered $^{111}$I-DOTA-biotin using pretargeting methods.

Evaluation of NRX451/SA in the full pretargeting mode was achieved by following the dosing schedule listed above. Shown in FIG. 24A are the blood, soft tissue and tumor concentrations of $^{125}$I radioactivity associated with the NRX451/SA conjugate at the time points following clearing agent and DOTA-biotin administration. Blood levels are quite low, consistent with the results of the studies in non-tumored mice, and the radioactivity usually present in the blood has been localized to liver, consistent with the receptor-mediated clearance associated with use of the GN16LCBT clearing agent. Tumor uptake, while apparently lower than that in FIG. 22, is actually greater in stoichiometric amounts of NRX451/SA, considering that the data in FIG. 22 resulted from administration of 50 μg of NRX451/SA versus 400 μg of NRX451/SA in the FIG. 24A data. Tumor retention over time is similar to historical controls of muNR-LU-10/SA used in the same dosing format. Little significant non-target retention of radiolabel is evident beyond the blood pool activity in each organ and the material being processed by the liver.

Figure 24B:
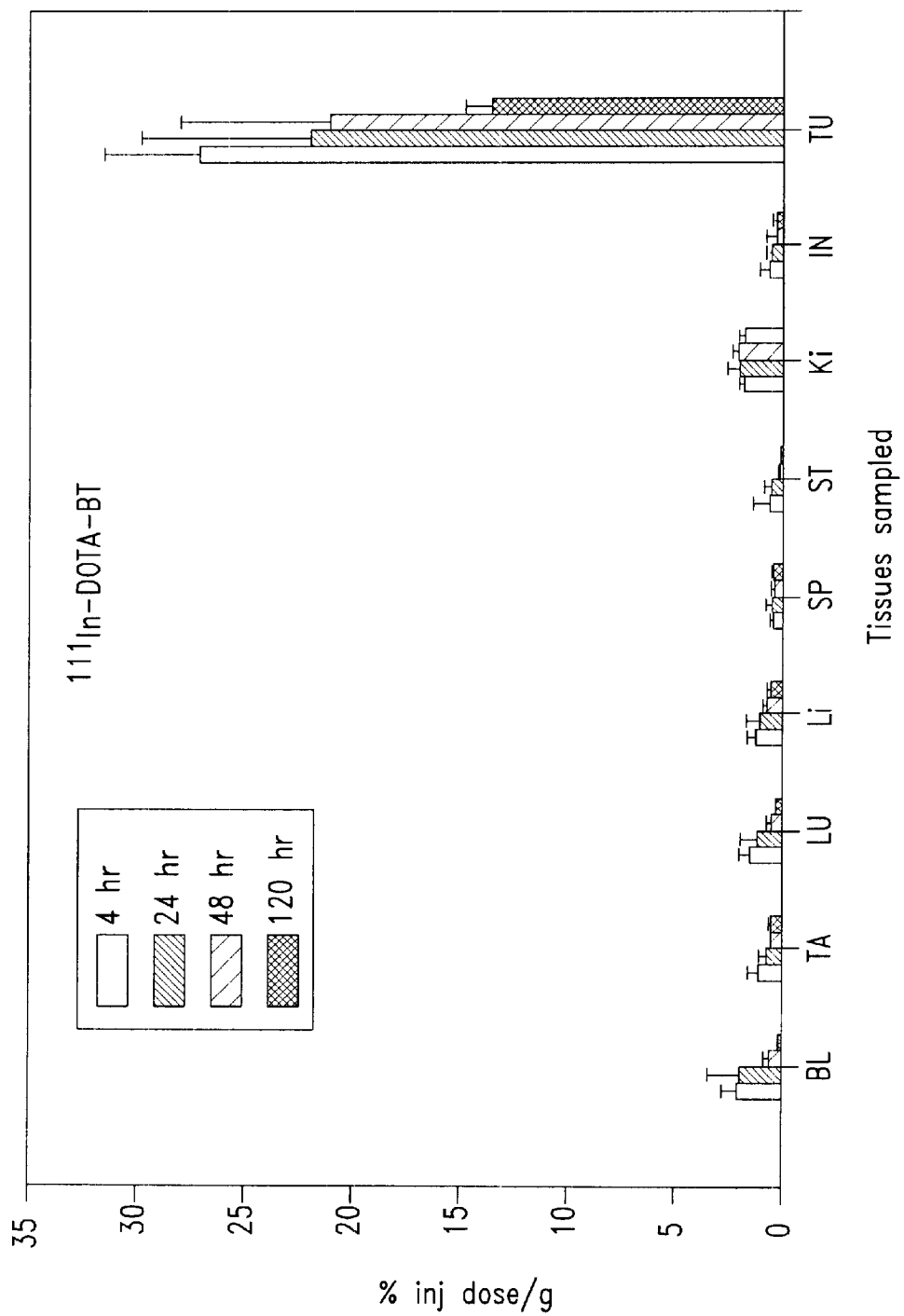

FIG. 24B shows the corresponding blood, soft tissue and tumor concentrations of $^{111}$In radioactivity associated with the DOTA-biotin administration. Low concentrations in all tissues except tumor are seen, with the rate, extent, and retention of tumor-associated radioactivity at all time points being consistent with those observed using the muLU-10/SA as a targeting agent. In the fall pretargeting application, utilizing chemical conjugates to streptavidin, there are no appreciable differences between NRX451 whole antibody (expressed in corn seed) and the murine form (hybridoma expressed).

From the foregoing, it will be evident that, although specific embodiments of the invention have been described herein for purposes of illustration, various modifications may be made without deviating from the spirit and scope of the invention.

What is claimed is:

1. The humanized antibody NRX 451 or an antigen-binding fragment thereof, wherein the murine parent antibody has ATCC Accession No: CRL-12360, and wherein the light chain variable region thereof comprises SEQ ID NO:18 and the heavy chain variable region thereof comprises SEQ ID NO:19.

2. The antibody or antibody fragment of claim 1 wherein said antibody or said antibody fragment either does not possess N-linked glycosylation or its N-linked glycosylation has been modified post expression to reduce immunogenicity or toxicity, and wherein said antibody or antibody fragment specifically binds to the antigen bound by antibody NR-LU-13(ATCC ACCESSION NO:CRL-12360).

3. The antibody or antibody fragment of claim 2 wherein the N-linked glycosylation has been modified chemically.

4. The antibody or antibody fragment of claim 3 wherein the N-linked glycosylation has been modified by oxidation followed by stabilization of the aldehydes generated by oxidation.

5. The antibody or antibody fragment of claim 4 wherein the N-linked glycosylation has been modified by oxidation followed by reduction.

6. The antibody or antibody fragment of any one of claims 1–5 wherein the polynucleotides encoding said antibody or said antibody fragment have been substituted or deleted in the glycosylation motif Asn-Xaa-Ser(Thr) of the $C_H2$ domain to prevent N-linked glycosylation in the $C_H2$ domain, wherein Xaa is any amino acid and Ser and Thr are interchangeable.

7. A composition comprising an antibody or antibody fragment according to claim 6 in combination with a pharmaceutically acceptable carrier or diluent.

* * * * *

UNITED STATES PATENT AND TRADEMARK OFFICE
CERTIFICATE OF CORRECTION

PATENT NO.    : 6,358,710 B1
DATED         : March 19, 2002
INVENTOR(S)   : Scott S. Graves et al.

It is certified that error appears in the above-identified patent and that said Letters Patent is hereby corrected as shown below:

<u>Title page,</u>
Item [56], References Cited, FOREIGN PATENT DOCUMENTS, should include the following reference:

-- WO     WO 89/01036     10/19/89 --.

Signed and Sealed this

Twenty-fourth Day of December, 2002

JAMES E. ROGAN
*Director of the United States Patent and Trademark Office*

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (xi) SEQUENCE DESCRIPTION: SEQ ID NO:1:

CCTGACGAAT TCGTTGACAT TGATTATTGA C                  31

(2) INFORMATION FOR SEQ ID NO:2:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (xi) SEQUENCE DESCRIPTION: SEQ ID NO:2:

CCTGACGCGG CCGCTTCGAT AAGCCAGTAA GC                          32

(2) INFORMATION FOR SEQ ID NO:3:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:3:

GTTCGGCTCG AGCACAGCTA GCATTATCTG GGATAAGCAT GCTG              44

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:4:

GTTACGGGGC CCCTAACACT CTCCCCTGTT GAAG                         34

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:5:

GTACGCGGAT CCCAGACACT GGACGCTG                                28

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:6:

CATTCGGAAT TCGAACCATC ACAGTCTCGC                              30

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:7:

GCTGACGAAT TCTCATTTAC CCGGAGACAG GGAG                         34

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:8:

CCGTCTATTA CTGTTCTAGA GAGGTC                                              26

(2) INFORMATION FOR SEQ ID NO:9:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:9:

CAGCGTGCGG CCGCACCATG GACATCAGGG CTCCTGCTCA G                              41

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:10:

AGCAGTACCA AAGCACGTAC CGGGTG                                              26

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:11:

TACGTGCTTT GGTACTGCTC CTC                                                 23

(2) INFORMATION FOR SEQ ID NO:12:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:12:

GCTGACGGAT CCTCATTTAC CCGGAGACAG GGAG                                     34

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:13:

CCGTCTATTA CTGTTCTAGA GAGGTC                                              26

(2) INFORMATION FOR SEQ ID NO:14:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ix) FEATURE:

(A) NAME/KEY: CDS
              (B) LOCATION: 1..360

(xi) SEQUENCE DESCRIPTION: SEQ ID NO:14:

GAG GTT CAG CTG CAG CAG TCT GGG GCA GAG CTT GTG AAG CCA GGG GCC        48
Glu Val Gln Leu Gln Gln Ser Gly Ala Glu Leu Val Lys Pro Gly Ala
  1               5                  10                  15

TCA GTC AGG TTG TCC TGC ACA GCT TCT GGC TTC AAC ATT AAA GAC ACC        96
Ser Val Arg Leu Ser Cys Thr Ala Ser Gly Phe Asn Ile Lys Asp Thr
             20                  25                  30

TAT ATG CAC TGG GTG ATA GAG AGG CCT GAA CAG GGC CTG GAG TGG ATT       144
Tyr Met His Trp Val Ile Glu Arg Pro Glu Gln Gly Leu Glu Trp Ile
         35                  40                  45

GGA AGG ATT GAT CCT GCG AAT GGT AAT ACT AAA TGT GAC CCG AAG TTC       192
Gly Arg Ile Asp Pro Ala Asn Gly Asn Thr Lys Cys Asp Pro Lys Phe
     50                  55                  60

CAG GGC AAG GCC ACT ATA ACA GCA GAC ACA TCC TCC AAC ACA GCC TAC       240
Gln Gly Lys Ala Thr Ile Thr Ala Asp Thr Ser Ser Asn Thr Ala Tyr
 65                  70                  75                  80

CTG CAG CTC AGC AGC CTG ACA TCT GAG GAC ACT GCC GTC TAT TAC TGT       288
Leu Gln Leu Ser Ser Leu Thr Ser Glu Asp Thr Ala Val Tyr Tyr Cys
                 85                  90                  95

TCT AGA GAG GTC CTA ACT GGG ACG TGG TCT TTG GAC TAC TGG GGT CAA       336
Ser Arg Glu Val Leu Thr Gly Thr Trp Ser Leu Asp Tyr Trp Gly Gln
            100                 105                 110

GGA ACC TCA GTC ACC GTC TCC TCA                                       360
Gly Thr Ser Val Thr Val Ser Ser
            115                 120

(2) INFORMATION FOR SEQ ID NO:15:

(i) SEQUENCE CHARACTERISTICS:
         (A) LENGTH: 120 amino acids
         (B) TYPE: amino acid
         (D) TOPOLOGY: linear (ii) MOLECULE TYPE: protein (xi) SEQUENCE DESCRIPTION: SEQ ID NO:15:

Glu Val Gln Leu Gln Gln Ser Gly Ala Glu Leu Val Lys Pro Gly Ala
  1               5                  10                  15

Ser Val Arg Leu Ser Cys Thr Ala Ser Gly Phe Asn Ile Lys Asp Thr
             20                  25                  30

Tyr Met His Trp Val Ile Glu Arg Pro Glu Gln Gly Leu Glu Trp Ile
         35                  40                  45

Gly Arg Ile Asp Pro Ala Asn Gly Asn Thr Lys Cys Asp Pro Lys Phe
     50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Ser Arg Glu Val Leu Thr Gly Thr Trp Ser Leu Asp Tyr Trp Gly Gln
            100                 105                 110

Gly Thr Ser Val Thr Val Ser Ser
            115                 120

(2) INFORMATION FOR SEQ ID NO:16:

(i) SEQUENCE CHARACTERISTICS:
         (A) LENGTH: 321 base pairs
         (B) TYPE: nucleic acid (C) STRANDEDNESS: single
        (D) TOPOLOGY: linear (ix) FEATURE:
        (A) NAME/KEY: CDS
        (B) LOCATION: 1..321

(xi) SEQUENCE DESCRIPTION: SEQ ID NO:16:

```
GAC ATC CAG ATG ATT CAG TCT CCA TCG TCC ATG TTT GCC TCT CTG GGA        48
Asp Ile Gln Met Ile Gln Ser Pro Ser Ser Met Phe Ala Ser Leu Gly
 1               5                  10                  15

GAC AGA GTC AGT CTC TCT TGT CGG GCT AGT CAG GGC ATT AGA GGT AAT        96
Asp Arg Val Ser Leu Ser Cys Arg Ala Ser Gln Gly Ile Arg Gly Asn
             20                  25                  30

TTA GAC TGG TAT CAG CAG AAA CCA GGT GGA ACT ATT AAA CTC CTG ATC       144
Leu Asp Trp Tyr Gln Gln Lys Pro Gly Gly Thr Ile Lys Leu Leu Ile
         35                  40                  45

TAC TCC ACA TCC AAT TTA AAT TCT GGT GTC CCA TCA AGG TTC AGT GGC       192
Tyr Ser Thr Ser Asn Leu Asn Ser Gly Val Pro Ser Arg Phe Ser Gly
 50                  55                  60

AGT GGG TCT GGG TCA GAT TAT TCT CTC ACC ATC AGC AGC CTA GAC TCT       240
Ser Gly Ser Gly Ser Asp Tyr Ser Leu Thr Ile Ser Ser Leu Asp Ser
 65                  70                  75                  80

GAA GAT TTT GCA GAC TAT TAC TGT CTA CAG CGT AAT GCG TAT CCG TAC       288
Glu Asp Phe Ala Asp Tyr Tyr Cys Leu Gln Arg Asn Ala Tyr Pro Tyr
                 85                  90                  95

ACG TTC GGA GGG GGG ACC AAG CTG GAA ATA AAA                           321
Thr Phe Gly Gly Gly Thr Lys Leu Glu Ile Lys
                100                 105
```

(2) INFORMATION FOR SEQ ID NO:17:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO:17:

```
Asp Ile Gln Met Ile Gln Ser Pro Ser Ser Met Phe Ala Ser Leu Gly
 1               5                  10                  15

Asp Arg Val Ser Leu Ser Cys Arg Ala Ser Gln Gly Ile Arg Gly Asn
             20                  25                  30

Leu Asp Trp Tyr Gln Gln Lys Pro Gly Gly Thr Ile Lys Leu Leu Ile
         35                  40                  45

Tyr Ser Thr Ser Asn Leu Asn Ser Gly Val Pro Ser Arg Phe Ser Gly
 50                  55                  60

Ser Gly Ser Gly Ser Asp Tyr Ser Leu Thr Ile Ser Ser Leu Asp Ser
 65                  70                  75                  80

Glu Asp Phe Ala Asp Tyr Tyr Cys Leu Gln Arg Asn Ala Tyr Pro Tyr
                 85                  90                  95

Thr Phe Gly Gly Gly Thr Lys Leu Glu Ile Lys
                100                 105
```

(2) INFORMATION FOR SEQ ID NO:18:

(i) SEQUENCE CHARACTERISTICS:
        (A) LENGTH: 107 amino acids
        (B) TYPE: amino acid
        (C) STRANDEDNESS:
        (D) TOPOLOGY: linear (xi) SEQUENCE DESCRIPTION: SEQ ID NO:18:

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Gly Asn
            20                  25                  30
Leu Asp Trp Tyr Gln Gln Lys Pro Gly Lys Gly Pro Lys Leu Leu Ile
            35                  40                  45
Tyr Ser Thr Ser Asn Leu Asn Ser Gly Val Pro Ser Arg Phe Ser Gly
        50                  55                  60
Ser Gly Ser Gly Ser Asp Tyr Thr Leu Thr Ile Ser Ser Leu Gln Pro
65                  70                  75                  80
Glu Asp Phe Ala Thr Tyr Tyr Cys Leu Gln Arg Asn Ala Tyr Pro Tyr
                85                  90                  95
Thr Phe Gly Gln Gly Thr Lys Leu Glu Ile Lys
                100                 105
```

(2) INFORMATION FOR SEQ ID NO:19:

(i) SEQUENCE CHARACTERISTICS:
        (A) LENGTH: 120 amino acids
        (B) TYPE: amino acid
        (C) STRANDEDNESS:
        (D) TOPOLOGY: linear (xi) SEQUENCE DESCRIPTION: SEQ ID NO:19:

```
Gln Val Gln Leu Val Gln Ser Gly Ala Glu Val Lys Lys Pro Gly Ala
1               5                   10                  15
Ser Val Lys Val Ser Cys Lys Ala Ser Gly Phe Asn Ile Lys Asp Thr
            20                  25                  30
Tyr Met His Trp Val Arg Gln Ala Pro Gly Gln Gly Leu Gln Trp Met
            35                  40                  45
Gly Arg Ile Asp Pro Ala Asn Gly Asn Thr Lys Cys Asp Leu Ser Phe
        50                  55                  60
Gln Gly Arg Val Thr Ile Thr Ala Asp Thr Ser Ile Asn Thr Ala Tyr
65                  70                  75                  80
Met Glu Leu Ser Ser Leu Arg Ser Asp Asp Thr Ala Val Tyr Tyr Cys
                85                  90                  95
Ser Arg Glu Val Leu Thr Gly Thr Trp Ser Leu Asp Tyr Trp Gly Gln
                100                 105                 110
Gly Thr Leu Val Thr Val Ser Ser
                115                 120
```